(12) United States Patent
Hirsch et al.

(10) Patent No.: US 11,471,251 B2
(45) Date of Patent: Oct. 18, 2022

(54) AUTOMATIC CREATION OF A VIRTUAL MODEL AND AN ORTHODONTIC TREATMENT PLAN

(71) Applicant: Hirsch Dynamics Holding AG, Wollerau (CH)

(72) Inventors: Markus Hirsch, Wollerau (CH); Konstantin Oppl, Purkersdorf (AT)

(73) Assignee: Hirsch Dynamics Holding AG, Wollerau (CH)

( * ) Notice: Subject to any disclaimer, the term of this patent is extended or adjusted under 35 U.S.C. 154(b) by 0 days.

(21) Appl. No.: 17/557,308

(22) Filed: Dec. 21, 2021

(65) Prior Publication Data

US 2022/0223285 A1  Jul. 14, 2022

(30) Foreign Application Priority Data

Dec. 23, 2020 (WO) ................ PCT/EP2020/087806

(51) Int. Cl.

| | |
|---|---|
| *A61C 7/00* | (2006.01) |
| *G16H 30/20* | (2018.01) |
| *G16H 50/20* | (2018.01) |
| *G06T 15/00* | (2011.01) |
| *G06T 19/00* | (2011.01) |

(Continued)

(52) U.S. Cl.
CPC ............ *A61C 7/002* (2013.01); *G06T 7/0012* (2013.01); *G06T 15/00* (2013.01); *G06T 17/00* (2013.01); *G06T 19/00* (2013.01); *G16H 30/20* (2018.01); *G16H 50/20* (2018.01)

(58) Field of Classification Search
CPC ....... A61C 13/0013; A61C 7/002; A61C 7/08; A61C 7/146; A61C 9/0006; A61C 9/0046; A61C 13/0004; A61C 13/34; G06K 9/6269; G06K 9/6273; G06K 9/6277; G06N 20/10; G06N 3/0454; G06N 3/0472; G06N 3/0481; G06N 3/08; G06V 10/82; G06V 20/41; G06V 20/46; G06V 40/15;

(Continued)

(56) References Cited

U.S. PATENT DOCUMENTS

| | | |
|---|---|---|
| 8,856,053 B2 | 10/2014 | Mah |
| 10,792,127 B2 | 10/2020 | Kopelman et al. |

(Continued)

FOREIGN PATENT DOCUMENTS

| | | |
|---|---|---|
| EP | 2 258 303 B1 | 9/2013 |
| EP | 1 723 589 B1 | 3/2020 |

(Continued)

OTHER PUBLICATIONS

Extended European Search Report in European Application No. 21216518.7-1207 dated May 12, 2022.

(Continued)

*Primary Examiner* — Manuchehr Rahmjoo
(74) *Attorney, Agent, or Firm* — Collard & Roe, P.C.

(57) ABSTRACT

A system and a computer-implemented method are provided to create a virtual model representing at least the individual visible teeth parts and gingiva of at least part of a dentition of a patient in segmented form out of a 3d model representing that part of the dentition in unsegmented form. At least one treatment plan is created and a process is provided for obtaining at least one appliance based on the at least one treatment plan.

12 Claims, 66 Drawing Sheets

(51) Int. Cl.
*G06T 7/00* (2017.01)
*G06T 17/00* (2006.01)

(58) Field of Classification Search
CPC .... G06V 40/161; G06V 40/169; G06V 40/40; G06V 40/45; G16H 50/50
See application file for complete search history.

(56) References Cited

U.S. PATENT DOCUMENTS

| | | | |
|---|---|---|---|
| 2018/0303581 A1* | 10/2018 | Martz | A61C 9/0006 |
| 2019/0192258 A1 | 6/2019 | Kang et al. | |
| 2019/0243795 A1 | 8/2019 | Oppl | |
| 2019/0357997 A1 | 11/2019 | Shi et al. | |
| 2020/0000555 A1 | 1/2020 | Yuryev et al. | |
| 2020/0015936 A1 | 1/2020 | Ye et al. | |

FOREIGN PATENT DOCUMENTS

| | | |
|---|---|---|
| EP | 3 359 080 B1 | 6/2020 |
| WO | 2018/101923 A1 | 6/2018 |
| WO | 2020/127824 A1 | 6/2020 |

OTHER PUBLICATIONS

Robert Goldblatt, Topoi,"The Categorial Analysis of Logic," revised edition, 2006 Dover Publications, total of 706 pages.
International Search Report and Written Opinion of the International Searching Authority in PCT/EP2020/087806, dated Nov. 12, 2021.
Khanagar SB et al., Scope and performance of artificial intelligence technology in orthodontic diagnosis, treatment planning, and clinical decision-making—A systematic review. Journal of Dental Sciences, https://doi.org/10.1016/j.ids.2020.05.22.
Asiri SN et al., Applications of artificial intelligence and machine learning in orthodontics. APOS Trends Orthod 2020, 10(1):17-24.
Torsdagli N et al., Deep Geodesic Learning for Segmentation and Anatomical Landmarking. IEEE Trans Med Imaging.
Hwang, Jae-Joon et al., An overview. Of deep learning in the field of dentistry. Imaging Sci Dent 2019, 49:1-7.
Li Peilin et al: Orthodontic Treatment Planning based on Artificial Neural Networks, Scientific Reports, vol. 9, No. 1, Dec. 1, 2019, p. 2037, XP 055856733.
Saunders Mac Lane, Categories for the Working Mathematician, Second Edition, 1998 Springer.
David I. Spivak, Category Theory for the Sciences, 2014 The MIT Press.
Tian Sukun et al: Automatic Classification and Segmentation of Teeth on 3D Dental Model Using Hierarchical Deep Learning Networks, IEEE Access, vol. 7, Jul. 15, 2019, pp. 84817-84828, XP011734278.
Kiaojie Xu et al: 3D Tooth Segmentation and Labeling using Deep Convolutional Neural Networks, IEEE Transactions on Visualization and Computer Graphics., May 22, 2018, pp. 1-13, XP055516965.
Wei Guodong et al: TANet: Towards Fully Automatic Tooth Arrangement: 16th European Conference, Glasgow, UK, Aug. 23-28, 2020, Proceedings, Part XV. Intelligent Robotics and Applications, Aug. 23, 2020, Springer International Publishing, Cham 032528, XP 055856708.

\* cited by examiner

Fig. 6
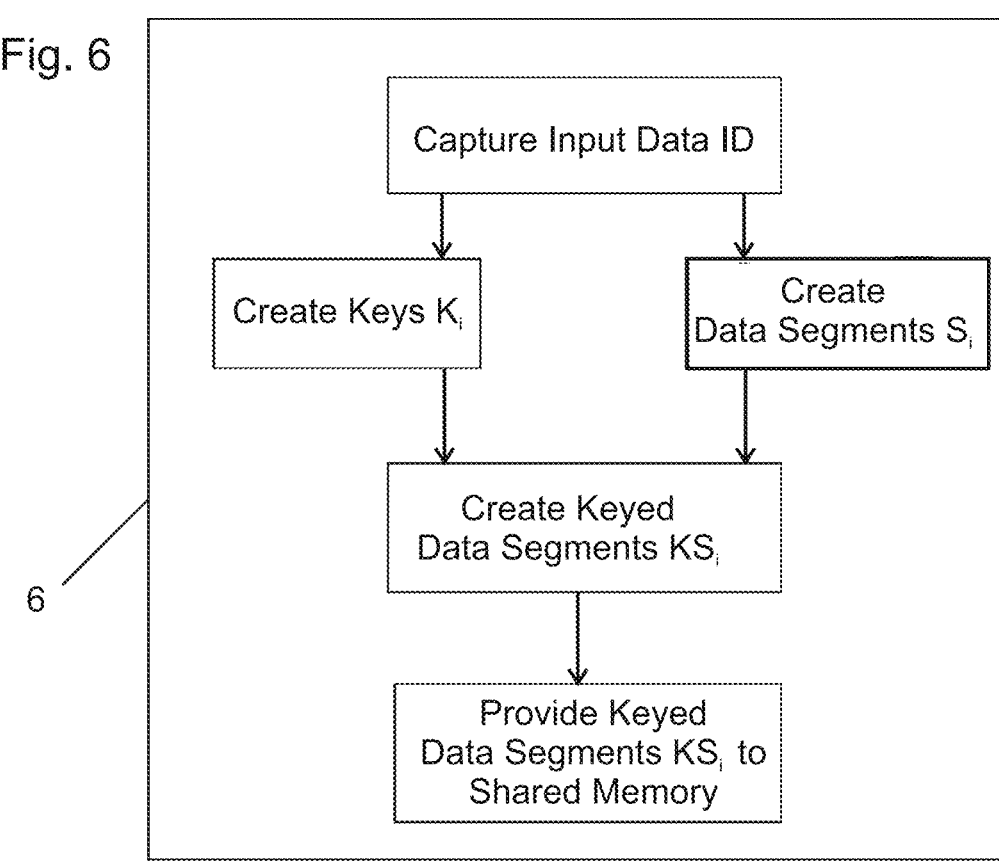
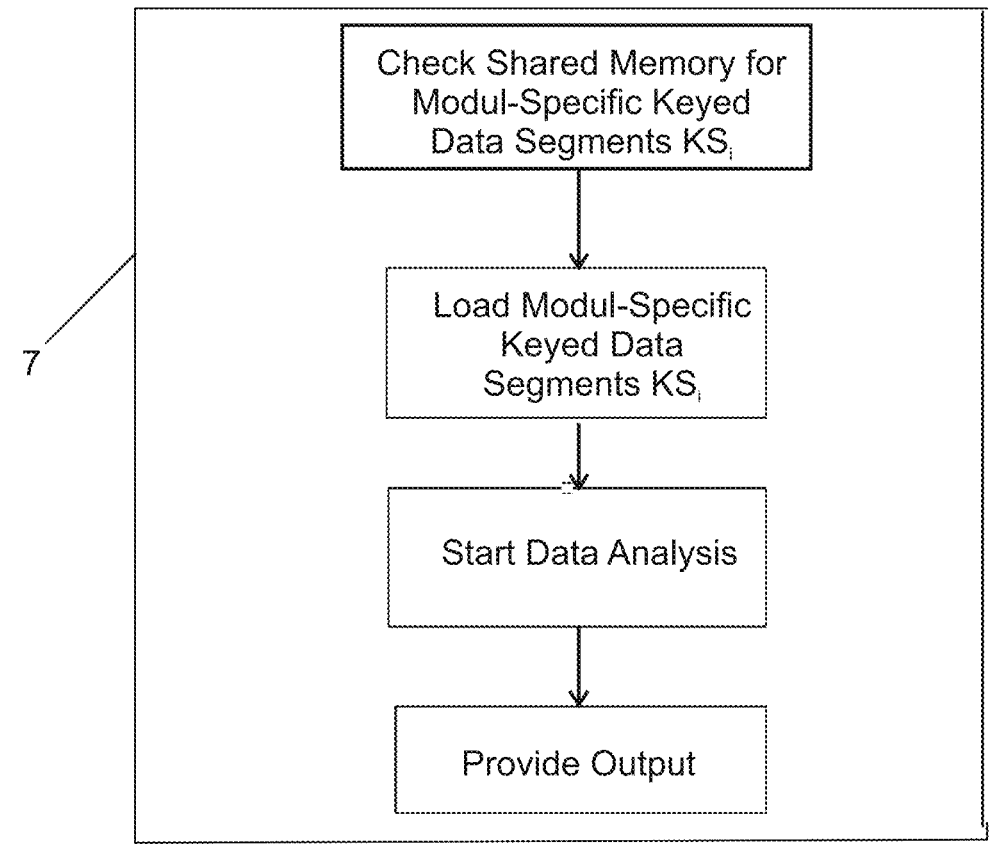

Fig. 8A
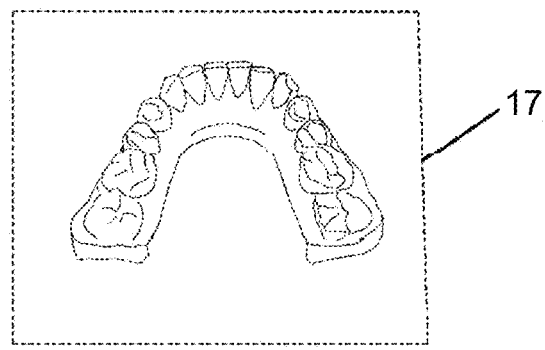
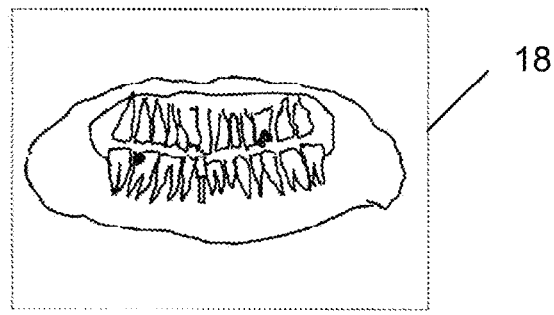
Fig. 8B
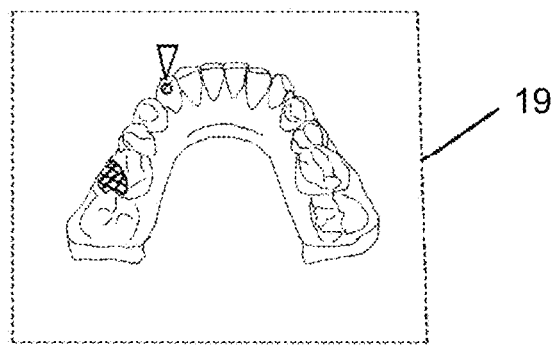

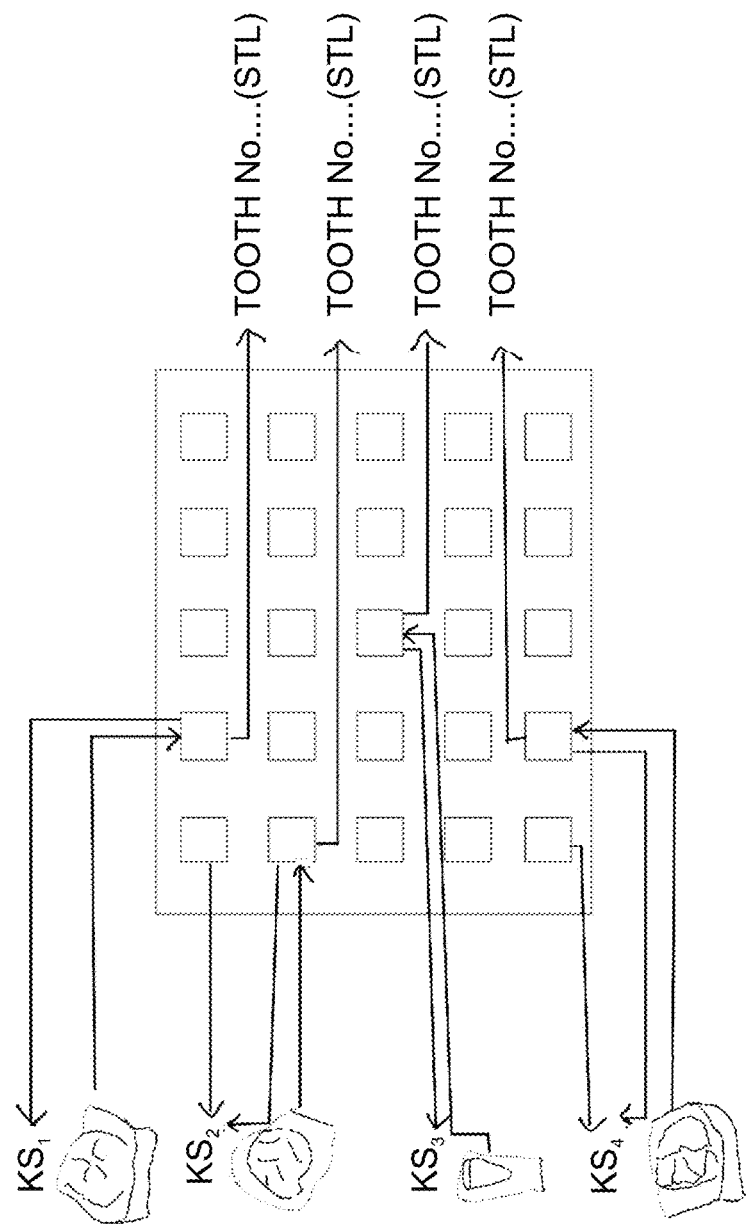

Fig. 25A 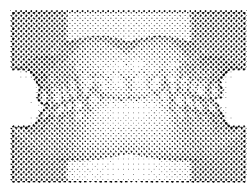 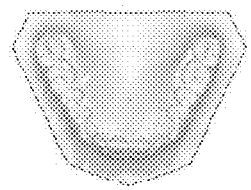 Fig. 25B
Fig. 26A 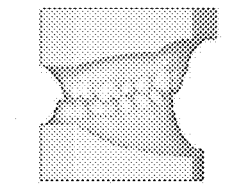 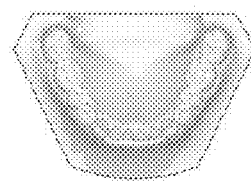 Fig. 26B
Fig. 27A 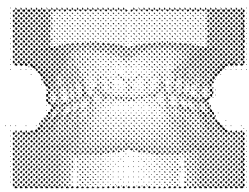 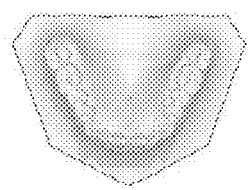 Fig. 27B
Fig. 28A 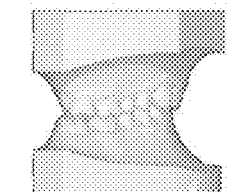 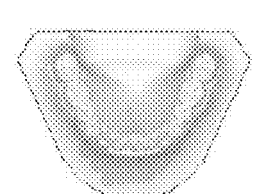 Fig. 28B
Fig. 29A 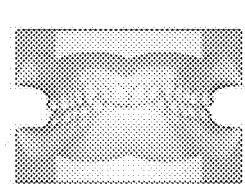 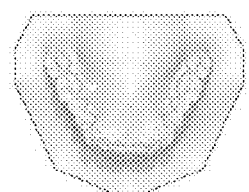 Fig. 29B
Fig. 30A 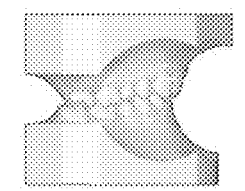 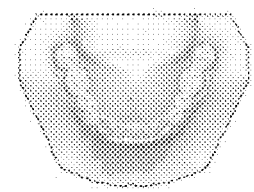 Fig. 30B

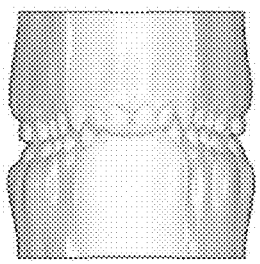 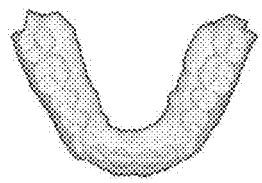
Fig. 37A         Fig. 37B
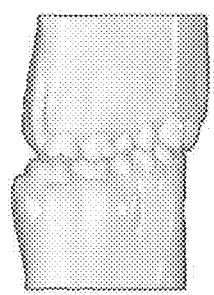 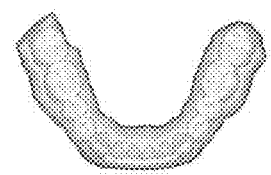
Fig. 38A         Fig. 38B
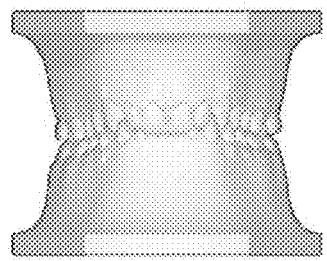 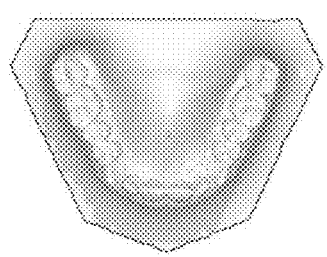
Fig. 39A         Fig. 39B
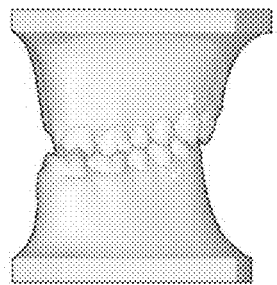 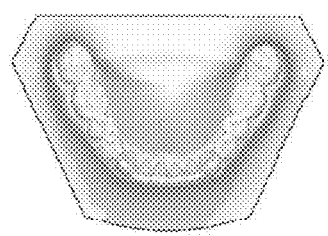
Fig. 40A         Fig. 40B

| Maxilla [mm] | 18d | 18m | 17d | 17m | 16d | 16m | 15d | 15m | 14d | 14m | 13d | 13m | 12d | 12m | 11d | 11m | 21d | 21m | 22d | 22m | 23d | 23m | 24d | 24m | 25d | 25m | 26d | 26m | 27d | 27m | 28d | 28m |
|---|---|---|---|---|---|---|---|---|---|---|---|---|---|---|---|---|---|---|---|---|---|---|---|---|---|---|---|---|---|---|---|---|
| Before Step 0 | | | | | | | | | | | | | | | | | | | | | | | | | | | | | | | | |
| Before Step 1 | | | | | | | | 0,3 | 0,2 | 0,2 | 0,2 | | | | | | | | | | | | | | | | | | | | | |
| Before Step 2 | | | | | | | | | | | | | | | 0,2 | 0,2 | | | | | | | | | | | | | | | | |
| Before Step 3 | | | | | | | | | | | | | | | | | | | | | 0,3 | | 0,2 | 0,2 | 0,3 | | | | | | | |
| Before Step 4 | | | | | | | | | | | | | | | | | | | | | | | | | | | | | | | | |
| Before Step 5 | | | | | | | | | | | | | | | | | | | | | | | | | | | | | | | | |
| Before Step 6 | | | | | | | | | | | | | | | | | | | | | | | | | | | | | | | | |
| Before Step 7 | | | | | | | | | | | | | | | | | | | | | | | | | | | | | | | | |
| Before Step 8 | | | | | | | | | | | | | | | | | | | | | | | | | | | | | | | | |
| Before Step 9 | | | | | | | | | | | | | | | | | | | | | | | | | | | | | | | | |
| Before Step 10 | | | | | | | | | | | | | | | | | | | | | | | | | | | | | | | | |
| Before Step 11 | | | | | | | | | | | | | | | | | | | | | | | | | | | | | | | | |
| Before Step 12 | | | | | | | | | | | | | | | | | | | | | | | | | | | | | | | | |
| Total | | | | | | | | 0,3 | 0,2 | 0,2 | 0,2 | | | | 0,2 | 0,2 | | | | | 0,3 | | 0,2 | 0,2 | 0,3 | | | | | | | |

| Mandible [mm] | 48d | 48m | 47d | 47m | 46d | 46m | 45d | 45m | 44d | 44m | 43d | 43m | 42d | 42m | 41d | 41m | 31d | 31m | 32d | 32m | 33d | 33m | 34d | 34m | 35d | 35m | 36d | 36m | 37d | 37m | 38d | 38m |
|---|---|---|---|---|---|---|---|---|---|---|---|---|---|---|---|---|---|---|---|---|---|---|---|---|---|---|---|---|---|---|---|---|
| Before Step 0 | | | | | | | | | | | | | | | | | | | | | | | | | | | | | | | | |
| Before Step 1 | | | | | | | | 0,3 | 0,2 | 0,2 | 0,2 | | | | | | | | | | | | | | | | | | | | | |
| Before Step 2 | | | | | | | | | | | | | | | 0,2 | 0,2 | | | | | | | | | | | | | | | | |
| Before Step 3 | | | | | | | | | | | | | | | | | | | | | 0,3 | | 0,2 | 0,2 | 0,3 | | | | | | | |
| Before Step 4 | | | | | | | | | | | | | | | | | | | | | | | | | | | | | | | | |
| Before Step 5 | | | | | | | | | | | | | | | | | | | | | | | | | | | | | | | | |
| Before Step 6 | | | | | | | | | | | | | | | | | | | | | | | | | | | | | | | | |
| Before Step 7 | | | | | | | | | | | | | | | | | | | | | | | | | | | | | | | | |
| Before Step 8 | | | | | | | | | | | | | | | | | | | | | | | | | | | | | | | | |
| Before Step 9 | | | | | | | | | | | | | | | | | | | | | | | | | | | | | | | | |
| Before Step 10 | | | | | | | | | | | | | | | | | | | | | | | | | | | | | | | | |
| Before Step 11 | | | | | | | | | | | | | | | | | | | | | | | | | | | | | | | | |
| Before Step 12 | | | | | | | | | | | | | | | | | | | | | | | | | | | | | | | | |
| Total | | | | | | | | | | | | | | | | | | | | | | | | | | | | | | | | |

Fig. 44B

| Maxilla | | | | | | | | |
|---|---|---|---|---|---|---|---|---|
| Tooth | 18 | 17 | 16 | 15 | 14 | 13 | 12 | 11 |
| Strip Mesial [mm] | | | | 0,3 | 0,2 | 0,2 | | 0,2 |
| Strip Distal [mm] | | | | | 0,2 | | | |
| Inclination [°] | | 8 | -10,8 | -1,5 | -14,3 | -10,8 | -11,9 | -19,9 |
| Inclination +/- [°] | | | | | | 0,1 | 0,6 | 1,4 |
| Angulation [°] | | -7,2 | 1,4 | 10,7 | 7,3 | 14,2 | 7,1 | -3,9 |
| Angulation +/- [°] | | | | | | -0,2 | | |
| Rotation +/- [°] | | | | | 0,1 | -0,8 | -1,3 | -0,1 |
| Mesial +/- [mm] | | | | | -0,04 | -0,08 | | 0,3 |
| Vestibular +/- [mm] | | | | | 0,01 | -0,02 | 0,01 | 0,12 |
| Occlusal +/- [mm] | | | | | -0,01 | -0,05 | 0,06 | 0,01 |

| Maxilla | | | | | | | | |
|---|---|---|---|---|---|---|---|---|
| Tooth | 21 | 22 | 23 | 24 | 25 | 26 | 27 | 28 |
| Strip Mesial [mm] | 0,2 | | | 0,2 | 0,3 | | | |
| Strip Distal [mm] | | | 0,3 | 0,2 | | | | |
| Inclination [°] | -16,1 | -12,4 | -13,6 | -17,1 | -8,4 | -14,3 | 7,8 | |
| Inclination +/- [°] | 1,5 | 1 | 0,4 | | | | | |
| Angulation [°] | -3,3 | 0 | 14,5 | 8,1 | 11 | 2,4 | -4 | |
| Angulation +/- [°] | 0,2 | 0,1 | -0,2 | | | | | |
| Rotation +/- [°] | -0,1 | -1,5 | -1,4 | | | | | |
| Mesial +/- [mm] | 0,03 | 0,02 | -0,05 | -0,03 | | | | |
| Vestibular +/- [mm] | 0,13 | 0,07 | -0,04 | 0,01 | | | | |
| Occlusal +/- [mm] | | 0,03 | -0,04 | | | | | |

Fig. 44B continued

| Mandible | | | | | | | | |
|---|---|---|---|---|---|---|---|---|
| Tooth | 48 | 47 | 46 | 45 | 44 | 43 | 42 | 41 |
| Strip Mesial [mm] | | | | | | | | |
| Strip Distal [mm] | | | | | | | | |
| Inclination [°] | | -31,1 | -30,8 | -25,1 | -16,1 | -3,8 | 14,5 | 11,8 |
| Inclination +/- [°] | | | | | | -0,2 | -0,6 | -0,3 |
| Angulation [°] | | 6,5 | 14,9 | 7,6 | 4,3 | 3,2 | -2,9 | -1,5 |
| Angulation +/- [°] | | | | | | 0,1 | 0,1 | |
| Rotation +/- [°] | | | | | | 0,3 | 0,3 | -0,1 |
| Mesial +/- [mm] | | | | | | | | 0,01 |
| Vestibular +/- [mm] | | | | | | 0,05 | 0,01 | 0,06 |
| Occlusal +/- [mm] | | -0,03 | -0,04 | | | -0,04 | -0,02 | |

| Mandible | | | | | | | | |
|---|---|---|---|---|---|---|---|---|
| Tooth | 31 | 32 | 33 | 34 | 35 | 36 | 37 | 38 |
| Strip Mesial [mm] | | | | | | | | |
| Strip Distal [mm] | | | | | | | | |
| Inclination [°] | 13 | 12,1 | -6,8 | -14,1 | -21,2 | -32,8 | -25,5 | |
| Inclination +/- | -0,2 | -0,3 | | | | | | |
| Angulation [°] | 2 | -2,3 | 10,2 | 12,2 | 3,5 | 17,9 | 5,5 | |
| Angulation +/- [°] | | | | | | | | |
| Rotation +/- [°] | | 0,1 | | | | | | |
| Mesial +/- [mm] | | | | | | | | |
| Vestibular +/- [mm] | 0,04 | 0,02 | 0,04 | | | | | |
| Occlusal +/- [mm] | | | -0,04 | | | | | |

Fig. 44C

| Maxilla | | | | | | | | |
|---|---|---|---|---|---|---|---|---|
| Tooth | 18 | 17 | 16 | 15 | 14 | 13 | 12 | 11 |
| Strip Mesial [mm] | | | | 0,3 | 0,2 | | | 0,2 |
| Strip Distal [mm] | | | | | 0,2 | 0,2 | | |
| Inclination [°] | | 8 | -10,8 | -1,5 | -14,3 | -10,7 | -11,4 | -18,7 |
| Inclination +/- [°] | | | | | | 0,1 | 0,5 | 1,2 |
| Angulation [°] | | -7,2 | 1,4 | 10,7 | 7,3 | 14 | 7,1 | -4 |
| Angulation +/- [°] | | | | | | | | |
| Rotation +/- [°] | | | | | | -0,2 | -1,1 | 0,2 |
| Mesial +/- [mm] | | | | | -0,03 | -0,07 | | |
| Vestibular +/- [mm] | | | | | 0,01 | -0,02 | 0,06 | 0,11 |
| Occlusal +/- [mm] | | | | | -0,01 | -0,04 | | |

| Maxilla | | | | | | | | |
|---|---|---|---|---|---|---|---|---|
| Tooth | 21 | 22 | 23 | 24 | 25 | 26 | 27 | 28 |
| Strip Mesial [mm] | 0,2 | | | 0,2 | 0,3 | | | |
| Strip Distal [mm] | | | 0,3 | 0,2 | | | | |
| Inclination [°] | -14,8 | -11,6 | -13,2 | -17,1 | -8,4 | -14,3 | 7,8 | |
| Inclination +/- [°] | 1,3 | 0,8 | 0,4 | | | | | |
| Angulation [°] | -3,2 | 0,1 | 14,3 | 8,1 | 11 | 2,4 | -4 | |
| Angulation +/- [°] | 0,1 | 0,1 | -0,2 | | | | | |
| Rotation +/- [°] | -0,1 | -1,3 | -1,2 | | | | | |
| Mesial +/- [mm] | 0,03 | 0,02 | -0,04 | -0,03 | | | | |
| Vestibular +/- [mm] | 0,11 | 0,06 | -0,04 | 0,01 | | | | |
| Occlusal +/- [mm] | | 0,03 | -0,03 | | | | | |

Fig. 44C continued

| Mandible | | | | | | | | |
|---|---|---|---|---|---|---|---|---|
| Tooth | 48 | 47 | 46 | 45 | 44 | 43 | 42 | 41 |
| Strip Mesial [mm] | | | | | | | | |
| Strip Distal [mm] | | | | | | | | |
| Inclination [°] | | -31,1 | -30,8 | -25,1 | -16,1 | -4 | 14,1 | 11,6 |
| Inclination +/- [°] | | -0,2 | | | | -0,2 | -0,5 | -0,2 |
| Angulation [°] | | 6,5 | 14,9 | 7,6 | 4,3 | 3,2 | -2,8 | -1,5 |
| Angulation +/- [°] | | | | | | 0,1 | 0,1 | |
| Rotation +/- [°] | | | | | | 0,3 | 0,2 | -0,1 |
| Mesial +/- [mm] | | | | | | | | 0,01 |
| Vestibular +/- [mm] | | | | | | 0,04 | 0,01 | 0,05 |
| Occlusal +/- [mm] | | | | | | -0,03 | -0,02 | |

| Mandible | | | | | | | | |
|---|---|---|---|---|---|---|---|---|
| Tooth | 31 | 32 | 33 | 34 | 35 | 36 | 37 | 38 |
| Strip Mesial [mm] | | | | | | | | |
| Strip Distal [mm] | | | | | | | | |
| Inclination [°] | 12,8 | 11,9 | -6,8 | -14,1 | -21,2 | -32,8 | -25,5 | |
| Inclination +/- | -0,2 | -0,2 | | | | | | |
| Angulation [°] | 2 | -2,3 | 10,2 | 12,2 | 3,5 | 17,9 | 5,5 | |
| Angulation +/- [°] | | | | | | | | |
| Rotation +/- [°] | | 0,1 | | | | | | |
| Mesial +/- [mm] | | | | | | | | |
| Vestibular +/- | 0,03 | 0,01 | 0,03 | | | | | |
| Occlusal +/- [mm] | | -0,02 | -0,04 | | | | | |

Fig. 44D

| Maxilla | | | | | | | | |
|---|---|---|---|---|---|---|---|---|
| Tooth | 18 | 17 | 16 | 15 | 14 | 13 | 12 | 11 |
| Strip Mesial [mm] | | | | 0,3 | 0,2 | 0,2 | | 0,2 |
| Strip Distal [mm] | | | | | 0,2 | | | |
| Inclination [°] | | 8 | -10,8 | -1,5 | -14,3 | -10,6 | -10,8 | -17,1 |
| Inclination +/- [°] | 1,7 | | | | | 0,1 | 0,7 | 1,6 |
| Angulation [°] | -3 | -7,2 | 1,4 | 10,7 | 7,3 | 13,7 | 7 | -4 |
| Angulation +/- [°] | 0,2 | | | | | -0,3 | | |
| Rotation +/- [°] | -0,1 | | | | 0,1 | -0,9 | -1,4 | 0,3 |
| Mesial +/- [mm] | 0,04 | | -0,05 | | -0,04 | -0,08 | | |
| Vestibular +/- [mm] | 0,15 | 0,08 | -0,05 | 0,01 | 0,01 | -0,03 | 0,07 | 0,14 |
| Occlusal +/- [mm] | -0,01 | 0,04 | -0,04 | -0,01 | -0,01 | -0,05 | | |

| Maxilla | | | | | | | | |
|---|---|---|---|---|---|---|---|---|
| Tooth | 21 | 22 | 23 | 24 | 25 | 26 | 27 | 28 |
| Strip Mesial [mm] | 0,2 | | | 0,2 | 0,3 | | | |
| Strip Distal [mm] | | | 0,3 | 0,2 | | | | |
| Inclination [°] | -13,1 | -10,5 | -12,7 | -17,1 | -8,4 | -14,3 | 7,8 | |
| Inclination +/- [°] | 1,7 | 1,1 | 0,5 | | | | | |
| Angulation [°] | -3 | 0,2 | 14 | 8,1 | 11 | 2,4 | -4 | |
| Angulation +/- [°] | 0,2 | 0,1 | -0,3 | | | | | |
| Rotation +/- [°] | -0,1 | -1,7 | -1,6 | 0,1 | | | | |
| Mesial +/- [mm] | 0,04 | 0,03 | -0,05 | -0,04 | | | | |
| Vestibular +/- [mm] | 0,15 | 0,08 | -0,05 | 0,01 | | | | |
| Occlusal +/- [mm] | -0,01 | 0,04 | -0,04 | -0,01 | | | | |

Fig. 44D continued

| Mandible | | | | | | | | |
|---|---|---|---|---|---|---|---|---|
| Tooth | 48 | 47 | 46 | 45 | 44 | 43 | 42 | 41 |
| Strip Mesial [mm] | | | | | | | | |
| Strip Distal [mm] | | | | | | | | |
| Inclination [°] | | -31,1 | -30,8 | -25,1 | -16,1 | -4,2 | 13,4 | 11,3 |
| Inclination +/- [°] | | | | | | -0,2 | -0,6 | -0,3 |
| Angulation [°] | | 6,5 | 14,9 | 7,6 | 4,3 | 3,3 | -2,7 | -1,4 |
| Angulation +/- [°] | | | | | | 0,1 | 0,1 | |
| Rotation +/- [°] | | | | | | 0,4 | 0,3 | -0,1 |
| Mesial +/- [mm] | | | | | | | | 0,01 |
| Vestibular +/- [mm] | | | | | | 0,06 | 0,01 | 0,07 |
| Occlusal +/- [mm] | | | | | | -0,04 | -0,03 | |

| Mandible | | | | | | | | |
|---|---|---|---|---|---|---|---|---|
| Tooth | 31 | 32 | 33 | 34 | 35 | 36 | 37 | 38 |
| Strip Mesial [mm] | | | | | | | | |
| Strip Distal [mm] | | | | | | | | |
| Inclination [°] | 12,6 | 11,6 | -6,8 | -14,1 | -21,2 | -32,8 | -25,5 | |
| Inclination +/- | -0,3 | -0,3 | | | | | | |
| Angulation [°] | 1,9 | -2,3 | 10,2 | 12,2 | 3,5 | 17,9 | 5,5 | |
| Angulation +/- [°] | | | | | | | | |
| Rotation +/- [°] | | 0,1 | | | | | | |
| Mesial +/- [mm] | | | | | | | | |
| Vestibular +/- [mm] | 0,04 | 0,02 | 0,04 | | | | | |
| Occlusal +/- [mm] | | -0,03 | -0,04 | | | | | |

Fig. 44E

| Maxilla | | | | | | | | |
|---|---|---|---|---|---|---|---|---|
| Tooth | 18 | 17 | 16 | 15 | 14 | 13 | 12 | 11 |
| Strip Mesial [mm] | 0,2 | | | 0,3 | 0,2 | 0,2 | | 0,2 |
| Strip Distal [mm] | | | | | 0,2 | | | |
| Inclination [°] | -11,8 | 8 | -10,8 | -1,5 | -14,3 | -10,5 | -10,3 | -15,8 |
| Inclination +/- [°] | 1,4 | | | | | 0,1 | 0,5 | 1,3 |
| Angulation [°] | -2,9 | -7,2 | 1,4 | 10,7 | 7,3 | 13,5 | 7 | -4 |
| Angulation +/- [°] | 0,1 | | | | | -0,2 | | |
| Rotation +/- [°] | -0,1 | | -1,3 | | | -0,8 | -1,1 | |
| Mesial +/- [mm] | 0,04 | 0,03 | -0,05 | | -0,03 | -0,05 | 0,01 | 0,01 |
| Vestibular +/- [mm] | 0,12 | 0,07 | -0,04 | 0,01 | 0,01 | -0,02 | 0,06 | 0,11 |
| Occlusal +/- [mm] | -0,01 | 0,03 | -0,04 | | -0,01 | -0,04 | | |

| Maxilla | | | | | | | | |
|---|---|---|---|---|---|---|---|---|
| Tooth | 21 | 22 | 23 | 24 | 25 | 26 | 27 | 28 |
| Strip Mesial [mm] | 0,2 | | 0,3 | 0,2 | 0,3 | | | |
| Strip Distal [mm] | | | | 0,2 | | | | |
| Inclination [°] | -11,8 | -9,6 | -12,3 | -17,1 | -8,4 | -14,3 | 7,8 | |
| Inclination +/- [°] | 1,4 | 0,9 | 0,4 | | | | | |
| Angulation [°] | -2,9 | 0,2 | 13,8 | 8,1 | 11 | 2,4 | -4 | |
| Angulation +/- [°] | 0,1 | | -0,2 | | | | | |
| Rotation +/- [°] | -0,1 | -1,4 | -1,3 | | | | | |
| Mesial +/- [mm] | 0,04 | 0,03 | -0,05 | -0,03 | | | | |
| Vestibular +/- [mm] | 0,12 | 0,07 | -0,04 | 0,01 | | | | |
| Occlusal +/- [mm] | -0,01 | 0,03 | -0,04 | | | | | |

Fig. 44E continued

| Mandible | | | | | | | | |
|---|---|---|---|---|---|---|---|---|
| Tooth | 48 | 47 | 46 | 45 | 44 | 43 | 42 | 41 |
| Strip Mesial [mm] | | | | | | | | |
| Strip Distal [mm] | | | | | | | | |
| Inclination [°] | | -31,1 | -30,8 | -25,1 | -16,1 | -4,3 | 12,9 | 11,1 |
| Inclination +/- [°] | | | | | | -0,2 | -0,5 | -0,2 |
| Angulation [°] | | 6,5 | 14,9 | 7,6 | 4,3 | 3,4 | -2,6 | -1,4 |
| Angulation +/- [°] | | | | | | 0,1 | 0,1 | |
| Rotation +/- [°] | | | | | | 0,3 | 0,2 | -0,1 |
| Mesial +/- [mm] | | | | | | | | 0,01 |
| Vestibular +/- [mm] | 0,03 | 0,02 | 0,03 | | | 0,05 | 0,03 | 0,06 |
| Occlusal +/- [mm] | | -0,02 | -0,04 | | | -0,04 | -0,02 | |

| Mandible | | | | | | | | |
|---|---|---|---|---|---|---|---|---|
| Tooth | 31 | 32 | 33 | 34 | 35 | 36 | 37 | 38 |
| Strip Mesial [mm] | | | | | | | | |
| Strip Distal [mm] | | | | | | | | |
| Inclination [°] | 12,3 | 11,4 | -6,8 | -14,1 | -21,2 | -32,8 | -25,5 | |
| Inclination +/- | -0,2 | -0,2 | | | | | | |
| Angulation [°] | 1,9 | -2,3 | 10,2 | 12,2 | 3,5 | 17,9 | 5,5 | |
| Angulation +/- [°] | | | | | | | | |
| Rotation +/- [°] | | 0,1 | | | | | | |
| Mesial +/- [mm] | | | | | | | | |
| Vestibular +/- [mm] | 0,03 | 0,02 | 0,03 | | | | | |
| Occlusal +/- [mm] | | -0,02 | -0,04 | | | | | |

Fig. 44F

| Maxilla | | | | | | | | |
|---|---|---|---|---|---|---|---|---|
| Tooth | 18 | 17 | 16 | 15 | 14 | 13 | 12 | 11 |
| Strip Mesial [mm] | 0,2 | | | 0,3 | 0,2 | 0,2 | | 0,2 |
| Strip Distal [mm] | | | | | 0,2 | | | |
| Inclination [°] | -10,1 | 8 | -10,8 | -1,5 | -14,3 | -10,4 | -9,6 | -14,3 |
| Inclination +/- [°] | 1,6 | | 0,4 | | | 0,1 | 0,6 | 1,5 |
| Angulation [°] | -2,8 | -7,2 | 1,4 | 10,7 | 7,3 | 13,2 | 6,9 | -4,1 |
| Angulation +/- [°] | 0,2 | | -0,3 | | | -0,3 | -0,1 | |
| Rotation +/- [°] | -0,1 | | | | 0,1 | -0,9 | -1,3 | 0,3 |
| Mesial +/- [mm] | 0,04 | | -0,05 | | -0,04 | -0,06 | 0,01 | 0,01 |
| Vestibular +/- [mm] | 0,14 | 0,08 | -0,04 | 0,01 | 0,01 | -0,03 | 0,07 | 0,13 |
| Occlusal +/- [mm] | -0,02 | 0,03 | -0,04 | -0,01 | -0,01 | -0,04 | | -0,01 |

| Maxilla | | | | | | | | |
|---|---|---|---|---|---|---|---|---|
| Tooth | 21 | 22 | 23 | 24 | 25 | 26 | 27 | 28 |
| Strip Mesial [mm] | 0,2 | | 0,3 | 0,2 | 0,3 | | | |
| Strip Distal [mm] | | | | 0,2 | | | | |
| Inclination [°] | -10,1 | -8,6 | -11,9 | -17,1 | -8,4 | -14,3 | | |
| Inclination +/- [°] | 1,6 | 1 | 0,4 | | | | 7,8 | |
| Angulation [°] | -2,8 | 0,2 | 13,5 | 8,1 | 11 | 2,4 | -4 | |
| Angulation +/- [°] | 0,2 | | -0,3 | | | | | |
| Rotation +/- [°] | -0,1 | -1,6 | -1,5 | 0,1 | | | | |
| Mesial +/- [mm] | 0,04 | 0,04 | -0,05 | -0,04 | | | | |
| Vestibular +/- [mm] | 0,14 | 0,08 | -0,04 | 0,01 | | | | |
| Occlusal +/- [mm] | -0,02 | 0,03 | -0,04 | -0,01 | | | | |

Fig. 44F continued

| Mandible | | | | | | | | |
|---|---|---|---|---|---|---|---|---|
| Tooth | 48 | 47 | 46 | 45 | 44 | 43 | 42 | 41 |
| Strip Mesial [mm] | | | | | | | | |
| Strip Distal [mm] | | | | | | | | |
| Inclination [°] | | -31,1 | -30,8 | -25,1 | -16,1 | -4,5 | 12,3 | 10,8 |
| Inclination +/- [°] | | | | | | -0,2 | -0,6 | -0,3 |
| Angulation [°] | | 6,5 | 14,9 | 7,6 | 4,3 | 3,4 | -2,5 | -1,4 |
| Angulation +/- [°] | | | | | | 0,1 | 0,1 | |
| Rotation +/- [°] | | | | | | 0,4 | 0,3 | -0,1 |
| Mesial +/- [mm] | | | | | | | | 0,01 |
| Vestibular +/- [mm] | | | | | | 0,05 | 0,04 | 0,07 |
| Occlusal +/- [mm] | | | -0,04 | | | -0,04 | -0,03 | |

| Mandible | | | | | | | | |
|---|---|---|---|---|---|---|---|---|
| Tooth | 31 | 32 | 33 | 34 | 35 | 36 | 37 | 38 |
| Strip Mesial [mm] | | | | | | | | |
| Strip Distal [mm] | | | | | | | | |
| Inclination [°] | 12,1 | 11,1 | -6,8 | -14,1 | -21,2 | -32,8 | -25,5 | |
| Inclination +/- | -0,3 | -0,3 | | | | | | |
| Angulation [°] | 1,8 | -2,3 | 10,2 | 12,2 | 3,5 | 17,9 | 5,5 | |
| Angulation +/- [°] | | 0,1 | | | | | | |
| Rotation +/- [°] | | | | | | | | |
| Mesial +/- [mm] | | | | | | | | |
| Vestibular +/- [mm] | 0,04 | 0,02 | 0,04 | | | | | |
| Occlusal +/- [mm] | | -0,03 | -0,04 | | | | | |

Fig. 44G

| Maxilla | | | | | | | | |
|---|---|---|---|---|---|---|---|---|
| Tooth | 18 | 17 | 16 | 15 | 14 | 13 | 12 | 11 |
| Strip Mesial [mm] | 0,2 | | | 0,3 | 0,2 | 0,2 | | 0,2 |
| Strip Distal [mm] | | | | | 0,2 | | | |
| Inclination [°] | -8,5 | 8 | -10,8 | -1,5 | -14,3 | -10,3 | -9 | -12,8 |
| Inclination +/- [°] | 1,6 | | 0,4 | | | 0,1 | 0,6 | 1,5 |
| Angulation [°] | -2,6 | -7,2 | 13,2 | 10,7 | 7,3 | 13 | 6,8 | -4,1 |
| Angulation +/- [°] | 0,1 | | -0,3 | | | -0,3 | -0,1 | |
| Rotation +/- [°] | -0,1 | | -1,5 | | 0,1 | -0,9 | -1,3 | 0,3 |
| Mesial +/- [mm] | 0,03 | 0,04 | -0,04 | | -0,04 | -0,03 | 0,02 | 0,01 |
| Vestibular +/- [mm] | 0,14 | 0,08 | -0,05 | 0,01 | 0,01 | -0,03 | 0,06 | 0,13 |
| Occlusal +/- [mm] | -0,02 | 0,03 | -0,04 | | -0,01 | -0,04 | | -0,01 |

| Maxilla | | | | | | | | |
|---|---|---|---|---|---|---|---|---|
| Tooth | 21 | 22 | 23 | 24 | 25 | 26 | 27 | 28 |
| Strip Mesial [mm] | 0,2 | | 0,3 | 0,2 | 0,3 | | | |
| Strip Distal [mm] | | | 0,3 | 0,2 | | | | |
| Inclination [°] | -8,5 | -7,6 | -11,5 | -17,1 | -8,4 | -14,3 | 7,8 | |
| Inclination +/- | 1,6 | 1 | 0,4 | | | | | |
| Angulation [°] | -2,6 | 0,2 | 13,2 | 8,1 | 11 | 2,4 | -4 | |
| Angulation +/- | 0,1 | | -0,3 | | | | | |
| Rotation +/- [°] | -0,1 | -1,6 | -1,5 | 0,1 | | | | |
| Mesial +/- [mm] | 0,03 | 0,04 | -0,04 | -0,04 | | | | |
| Vestibular +/- | 0,14 | 0,08 | -0,05 | 0,01 | | | | |
| Occlusal +/- [mm] | -0,02 | 0,03 | -0,04 | | | | | |

Fig. 44G continued

| Mandible | | | | | | | | |
|---|---|---|---|---|---|---|---|---|
| Tooth | 48 | 47 | 46 | 45 | 44 | 43 | 42 | 41 |
| Strip Mesial [mm] | | | | | | | | |
| Strip Distal [mm] | | | | | | | | |
| Inclination [°] | | -31,1 | -30,8 | -25,1 | -16,1 | -4,7 | 11,7 | 10,6 |
| Inclination +/- [°] | | | | | | -0,2 | -0,6 | -0,3 |
| Angulation [°] | | 6,5 | 14,9 | 7,6 | 4,3 | 3,5 | -2,4 | -1,4 |
| Angulation +/- [°] | | | | | | 0,1 | 0,1 | |
| Rotation +/- [°] | | | | | | 0,3 | 0,3 | -0,1 |
| Mesial +/- [mm] | | | | | | | | 0,01 |
| Vestibular +/- [mm] | | | | | | 0,05 | | 0,07 |
| Occlusal +/- [mm] | | | | | | -0,04 | -0,03 | |

| Mandible | | | | | | | | |
|---|---|---|---|---|---|---|---|---|
| Tooth | 31 | 32 | 33 | 34 | 35 | 36 | 37 | 38 |
| Strip Mesial [mm] | | | | | | | | |
| Strip Distal [mm] | | | | | | | | |
| Inclination [°] | 11,8 | 10,9 | -6,8 | -14,1 | -21,2 | -32,8 | -25,5 | |
| Inclination +/- | -0,3 | -0,3 | | | | | | |
| Angulation [°] | 1,8 | -2,3 | 10,2 | 12,2 | 3,5 | 17,9 | 5,5 | |
| Angulation +/- [°] | | | | | | | | |
| Rotation +/- [°] | | 0,1 | | | | | | |
| Mesial +/- [mm] | | | | | | | | |
| Vestibular +/- [mm] | 0,04 | 0,02 | 0,04 | | | | | |
| Occlusal +/- [mm] | | -0,03 | -0,04 | | | | | |

Fig. 44H

| Maxilla | | | | | | | | |
|---|---|---|---|---|---|---|---|---|
| Tooth | 18 | 17 | 16 | 15 | 14 | 13 | 12 | 11 |
| Strip Mesial [mm] | 0,2 | | | 0,3 | 0,2 | 0,2 | | 0,2 |
| Strip Distal [mm] | | | | | 0,2 | 0,2 | | |
| Inclination [°] | -7,2 | 8 | -10,8 | -1,5 | -14,3 | -10,2 | -8,5 | -11,4 |
| Inclination +/- [°] | 1,4 | | | | | 0,1 | 0,5 | 1,3 |
| Angulation [°] | -2,5 | -7,2 | 1,4 | 10,7 | 7,3 | 12,7 | 6,7 | -4,1 |
| Angulation +/- [°] | 0,1 | | -0,3 | | | -0,2 | -0,1 | |
| Rotation +/- [°] | -0,1 | | -1,3 | | | -0,8 | -1,1 | 0,3 |
| Mesial +/- [mm] | 0,03 | 0,03 | -0,03 | | -0,03 | -0,03 | 0,02 | 0,01 |
| Vestibular +/- [mm] | 0,12 | 0,07 | -0,04 | | 0,01 | -0,02 | 0,06 | 0,11 |
| Occlusal +/- [mm] | -0,02 | 0,02 | -0,04 | | -0,01 | -0,03 | | -0,01 |

| Maxilla | | | | | | | | |
|---|---|---|---|---|---|---|---|---|
| Tooth | 21 | 22 | 23 | 24 | 25 | 26 | 27 | 28 |
| Strip Mesial [ | 0,2 | | 0,3 | 0,2 | 0,3 | | | |
| Strip Distal [mm] | | | | 0,2 | | | | |
| Inclination [°] | -7,2 | -6,7 | -11,1 | -17,1 | -8,4 | -14,3 | 7,8 | |
| Inclination +/- | 1,4 | 0,9 | 0,4 | | | | | |
| Angulation [°] | -2,5 | 0,2 | 12,9 | 8,1 | 11 | 2,4 | -4 | |
| Angulation +/- | 0,1 | | -0,3 | | | | | |
| Rotation +/- [° | -0,1 | -1,4 | -1,3 | | | | | |
| Mesial +/- [m | 0,03 | 0,03 | -0,03 | -0,03 | | | | |
| Vestibular +/- [ | 0,12 | 0,07 | -0,04 | 0,01 | | | | |
| Occlusal +/- [r | -0,02 | 0,02 | -0,04 | | | | | |

Fig. 44H continued

| Mandible | | | | | | | | |
|---|---|---|---|---|---|---|---|---|
| Tooth | 48 | 47 | 46 | 45 | 44 | 43 | 42 | 41 |
| Strip Mesial [mm] | | | | | | | | |
| Strip Distal [mm] | | | | | | | | |
| Inclination [°] | | -31,1 | -30,8 | -25,1 | -16,1 | -4,9 | 11,2 | 10,3 |
| Inclination +/- [°] | | | | | | -0,2 | -0,5 | -0,2 |
| Angulation [°] | | 6,5 | 14,9 | 7,6 | 4,3 | 3,5 | -2,3 | -1,3 |
| Angulation +/- [°] | | | | | | | 0,1 | |
| Rotation +/- [°] | | | | | | 0,3 | 0,2 | -0,1 |
| Mesial +/- [mm] | | | | | | | | 0,01 |
| Vestibular +/- [mm] | | | | | | 0,05 | | 0,06 |
| Occlusal +/- [mm] | | | -0,04 | | | -0,04 | -0,03 | |

| Mandible | | | | | | | | |
|---|---|---|---|---|---|---|---|---|
| Tooth | 31 | 32 | 33 | 34 | 35 | 36 | 37 | 38 |
| Strip Mesial [mm] | | | | | | | | |
| Strip Distal [mm] | | | | | | | | |
| Inclination [°] | 11,6 | 10,6 | -6,8 | -14,1 | -21,2 | -32,8 | -25,5 | |
| Inclination +/- | -0,2 | -0,2 | | | | | | |
| Angulation [°] | 1,8 | -2,3 | 10,2 | 12,2 | 3,5 | 17,9 | 5,5 | |
| Angulation +/- [°] | | | | | | | | |
| Rotation +/- [°] | | 0,1 | | | | | | |
| Mesial +/- [mm] | | | | | | | | |
| Vestibular +/- [mm] | 0,04 | 0,02 | 0,03 | | | | | |
| Occlusal +/- [mm] | | -0,03 | -0,04 | | | | | |

Fig. 44I

| Maxilla | | | | | | | | |
|---|---|---|---|---|---|---|---|---|
| Tooth | 18 | 17 | 16 | 15 | 14 | 13 | 12 | 11 |
| Strip Mesial [mm] | 0,2 | | | 0,3 | 0,2 | 0,2 | | |
| Strip Distal [mm] | | | | | 0,2 | | | 0,2 |
| Inclination [°] | -5,6 | 8 | -10,8 | -1,5 | -14,3 | -10,1 | -7,9 | -10 |
| Inclination +/- [°] | 1,6 | | 0,4 | | | 0,1 | 0,6 | 1,5 |
| Angulation [°] | -2,3 | -7,2 | 1,4 | 10,7 | 7,3 | 12,5 | 6,6 | -4,1 |
| Angulation +/- [°] | 0,1 | | -0,3 | | | -0,3 | -0,1 | |
| Rotation +/- [°] | -0,1 | | -1,4 | | 0,1 | -0,8 | -1,3 | 0,3 |
| Mesial +/- [mm] | 0,04 | 0,05 | -0,05 | | -0,04 | -0,05 | | |
| Vestibular +/- [mm] | 0,14 | 0,07 | -0,05 | -0,03 | 0,01 | -0,03 | 0,07 | 0,13 |
| Occlusal +/- [mm] | -0,03 | 0,03 | -0,04 | 0,01 | -0,01 | -0,04 | | -0,02 |

| Maxilla | | | | | | | | |
|---|---|---|---|---|---|---|---|---|
| Tooth | 21 | 22 | 23 | 24 | 25 | 26 | 27 | 28 |
| Strip Mesial [mm] | 0,2 | | 0,3 | 0,2 | 0,3 | | | |
| Strip Distal [mm] | | | | 0,2 | | | | |
| Inclination [°] | -5,6 | -5,7 | -10,7 | -17,1 | -8,4 | -14,3 | 7,8 | |
| Inclination +/- [°] | 1,6 | 1 | 0,4 | | | | | |
| Angulation [°] | -2,3 | 0,1 | 12,6 | 8,1 | 11 | 2,4 | -4 | |
| Angulation +/- [°] | 0,1 | -0,1 | -0,3 | | | | | |
| Rotation +/- [°] | -0,1 | -1,6 | -1,4 | | | | | |
| Mesial +/- [mm] | 0,04 | 0,05 | -0,05 | -0,03 | | | | |
| Vestibular +/- [mm] | 0,14 | 0,07 | -0,05 | 0,01 | | | | |
| Occlusal +/- [mm] | -0,03 | 0,03 | -0,04 | | | | | |

Fig. 44I continued

| Mandible | | | | | | | | |
|---|---|---|---|---|---|---|---|---|
| Tooth | 48 | 47 | 46 | 45 | 44 | 43 | 42 | 41 |
| Strip Mesial [mm] | | | | | | | | |
| Strip Distal [mm] | | | | | | | | |
| Inclination [°] | | -31,1 | -30,8 | -25,1 | -16,1 | -5,1 | 10,6 | 10,1 |
| Inclination +/- [°] | | | | | | -0,2 | -0,6 | -0,3 |
| Angulation [°] | | 6,5 | 14,9 | 7,6 | 4,3 | 3,6 | -2,2 | -1,3 |
| Angulation +/- [°] | | | | | | 0,1 | 0,1 | |
| Rotation +/- [mm] | | | | | | 0,3 | 0,3 | -0,1 |
| Mesial +/- [mm] | | | | | | | | 0,01 |
| Vestibular +/- [mm] | | | | | | 0,05 | | 0,06 |
| Occlusal +/- [mm] | | | 0,04 | | | -0,04 | -0,03 | |

| Mandible | | | | | | | | |
|---|---|---|---|---|---|---|---|---|
| Tooth | 31 | 32 | 33 | 34 | 35 | 36 | 37 | 38 |
| Strip Mesial [mm] | | | | | | | | |
| Strip Distal [mm] | | | | | | | | |
| Inclination [°] | 11,4 | 10,4 | -6,8 | -14,1 | -21,2 | -32,8 | -25,5 | |
| Inclination +/- | -0,2 | -0,3 | | | | | | |
| Angulation [°] | 1,7 | -2,3 | 10,2 | 12,2 | 3,5 | 17,9 | 5,5 | |
| Angulation +/- [°] | | | | | | | | |
| Rotation +/- [°] | | 0,1 | | | | | | |
| Mesial +/- [mm] | | | | | | | | |
| Vestibular +/- [mm] | 0,04 | 0,02 | 0,04 | | | | | |
| Occlusal +/- [mm] | | -0,03 | -0,04 | | | | | |

Fig. 44J

| Maxilla | | | | | | | | |
|---|---|---|---|---|---|---|---|---|
| Tooth | 18 | 17 | 16 | 15 | 14 | 13 | 12 | 11 |
| Strip Mesial [mm] | 0,2 | | | 0,3 | 0,2 | 0,2 | | 0,2 |
| Strip Distal [mm] | | | | | 0,2 | | | |
| Inclination [°] | -4,2 | 8 | -10,8 | -1,5 | -14,3 | -10,1 | -7,3 | -8,6 |
| Inclination +/- [°] | 1,4 | | | | | 0,1 | 0,5 | 1,4 |
| Angulation [°] | -2,2 | -7,2 | 1,4 | 10,7 | 7,3 | 12,2 | 6,5 | -4,1 |
| Angulation +/- [°] | 0,1 | | -0,3 | | | -0,2 | -0,1 | |
| Rotation +/- [°] | -0,1 | | -1,3 | | 0,1 | -0,8 | -1,2 | 0,3 |
| Mesial +/- [mm] | 0,04 | 0,05 | -0,05 | | -0,04 | -0,05 | | |
| Vestibular +/- [mm] | 0,13 | 0,07 | -0,04 | 0,01 | 0,01 | -0,03 | 0,06 | 0,12 |
| Occlusal +/- [mm] | -0,03 | 0,02 | -0,04 | -0,01 | -0,01 | -0,04 | | -0,02 |

| Maxilla | | | | | | | | |
|---|---|---|---|---|---|---|---|---|
| Tooth | 21 | 22 | 23 | 24 | 25 | 26 | 27 | 28 |
| Strip Mesial [mm] | 0,2 | | | 0,2 | 0,3 | | | |
| Strip Distal [mm] | | | 0,3 | 0,2 | | | | |
| Inclination [°] | -4,2 | -4,8 | -10,3 | -17,1 | -8,4 | -14,3 | 7,8 | |
| Inclination +/- [°] | 1,4 | 0,9 | 0,4 | | | | | |
| Angulation [°] | -2,2 | 0 | 12,4 | 8,1 | 11 | 2,4 | -4 | |
| Angulation +/- [°] | 0,1 | -0,1 | -0,3 | | | | | |
| Rotation +/- [°] | -0,1 | -1,5 | -1,3 | | | | | |
| Mesial +/- [mm] | 0,04 | 0,05 | -0,05 | -0,03 | | | | |
| Vestibular +/- [mm] | 0,13 | 0,07 | -0,04 | 0,01 | | | | |
| Occlusal +/- [mm] | -0,03 | 0,02 | -0,04 | -0,01 | | | | |

Fig. 44J continued

| Mandible | | | | | | | | |
|---|---|---|---|---|---|---|---|---|
| Tooth | 48 | 47 | 46 | 45 | 44 | 43 | 42 | 41 |
| Strip Mesial [mm] | | | | | | | | |
| Strip Distal [mm] | | | | | | | | |
| Inclination [°] | | -31,1 | -30,8 | -25,1 | -16,1 | -5,3 | 10,1 | 9,9 |
| Inclination +/- [°] | | | | | | -0,2 | -0,5 | -0,2 |
| Angulation [°] | | 6,5 | 14,9 | 7,6 | 4,3 | 3,6 | -2,1 | -1,3 |
| Angulation +/- [°] | | | | | | | 0,1 | |
| Rotation +/- [°] | | | | | | 0,3 | 0,2 | -0,1 |
| Mesial +/- [mm] | | | | | | | | 0,01 |
| Vestibular +/- [mm] | | | | | | 0,05 | | 0,06 |
| Occlusal +/- [mm] | | | -0,04 | | | -0,04 | -0,03 | |

| Mandible | | | | | | | | |
|---|---|---|---|---|---|---|---|---|
| Tooth | 31 | 32 | 33 | 34 | 35 | 36 | 37 | 38 |
| Strip Mesial [mm] | | | | | | | | |
| Strip Distal [mm] | | | | | | | | |
| Inclination [°] | 11,1 | 10,2 | -6,8 | -14,1 | -21,2 | -32,8 | -25,5 | |
| Inclination +/- | -0,2 | -0,2 | | | | | | |
| Angulation [°] | 1,7 | -2,3 | 10,2 | 12,2 | 3,5 | 17,9 | 5,5 | |
| Angulation +/- [°] | | | | | | | | |
| Rotation +/- [°] | | 0,1 | | | | | | |
| Mesial +/- [mm] | | | | | | | | |
| Vestibular +/- [mm] | 0,04 | 0,02 | 0,03 | | | | | |
| Occlusal +/- [mm] | | -0,03 | -0,04 | | | | | |

Fig. 44K

| Maxilla | | | | | | | | |
|---|---|---|---|---|---|---|---|---|
| Tooth | 18 | 17 | 16 | 15 | 14 | 13 | 12 | 11 |
| Strip Mesial [mm] | 0,2 | | | 0,3 | 0,2 | 0,2 | | 0,2 |
| Strip Distal [mm] | | | | | 0,2 | | | |
| Inclination [°] | -2,6 | 8 | -10,8 | -1,5 | -14,3 | -10 | -6,8 | -7,2 |
| Inclination +/- [°] | 1,5 | | | | | 0,1 | 0,6 | 1,4 |
| Angulation [°] | -2,1 | -7,2 | 1,4 | 10,7 | 7,3 | 12 | 6,4 | -4,1 |
| Angulation +/- [°] | 0,1 | | | | | -0,3 | -0,1 | |
| Rotation +/- [°] | -0,1 | | | | 0,1 | -0,8 | -1,2 | 0,3 |
| Mesial +/- [mm] | 0,03 | | -0,02 | | -0,04 | -0,02 | | -0,01 |
| Vestibular +/- [mm] | 0,13 | 0,07 | -0,03 | 0,01 | 0,01 | -0,03 | 0,07 | 0,13 |
| Occlusal +/- [mm] | -0,03 | 0,02 | -0,04 | -0,01 | -0,01 | -0,03 | | -0,02 |

| Maxilla | | | | | | | | |
|---|---|---|---|---|---|---|---|---|
| Tooth | 21 | 22 | 23 | 24 | 25 | 26 | 27 | 28 |
| Strip Mesial [r | 0,2 | | 0,3 | 0,2 | 0,3 | | | |
| Strip Distal [mm] | | | 0,3 | 0,2 | | | | |
| Inclination [°] | -2,6 | -3,9 | -9,9 | -17,1 | -8,4 | -14,3 | 7,8 | |
| Inclination +/- | 1,5 | 1 | 0,4 | | | 0,1 | | |
| Angulation [°] | -2,1 | -0,1 | 12 | 8,1 | 11 | 2,4 | -4 | |
| Angulation +/- | 0,1 | -0,1 | -0,3 | | | | | |
| Rotation +/- [° | -0,1 | -1,5 | -1,4 | | | | | |
| Mesial +/- [m | 0,03 | 0,04 | -0,02 | -0,03 | | | | |
| Vestibular +/- | 0,13 | 0,07 | -0,03 | 0,01 | | | | |
| Occlusal +/- [r | -0,03 | 0,02 | -0,04 | -0,01 | | | | |

Fig. 44K continued

| Mandible | | | | | | | | |
|---|---|---|---|---|---|---|---|---|
| Tooth | 48 | 47 | 46 | 45 | 44 | 43 | 42 | 41 |
| Strip Mesial [mm] | | | | | | | | |
| Strip Distal [mm] | | | | | | | | |
| Inclination [°] | | -31,1 | -30,8 | -25,1 | -16,1 | -5,5 | 9,5 | 9,6 |
| Inclination +/- [°] | | | | | | -0,2 | -0,6 | -0,3 |
| Angulation [°] | | 6,5 | 14,9 | 7,6 | 4,3 | 3,7 | -2 | -1,2 |
| Angulation +/- [°] | | | | | | 0,1 | 0,1 | |
| Rotation +/- [°] | | | | | | 0,3 | 0,3 | -0,1 |
| Mesial +/- [mm] | | | | | | | | 0,01 |
| Vestibular +/- [mm] | | | | | | 0,05 | | 0,06 |
| Occlusal +/- [mm] | | -0,03 | -0,04 | | | -0,04 | -0,03 | |

| Mandible | | | | | | | | |
|---|---|---|---|---|---|---|---|---|
| Tooth | 31 | 32 | 33 | 34 | 35 | 36 | 37 | 38 |
| Strip Mesial [mm] | | | | | | | | |
| Strip Distal [mm] | | | | | | | | |
| Inclination [°] | 10,9 | 9,9 | -6,8 | -14,1 | -21,2 | -32,8 | -25,5 | |
| Inclination +/- | -0,2 | -0,3 | | | | | | |
| Angulation [°] | 1,6 | -2,3 | 10,2 | 12,2 | 3,5 | 17,9 | 5,5 | |
| Angulation +/- [°] | | | | | | | | |
| Rotation +/- [°] | | 0,1 | | | | | | |
| Mesial +/- [mm] | | | | | | | | |
| Vestibular +/- [mm] | 0,04 | 0,02 | 0,04 | | | | | |
| Occlusal +/- [mm] | | -0,03 | -0,04 | | | | | |

Fig. 44L

| Maxilla | | | | | | | | |
|---|---|---|---|---|---|---|---|---|
| Tooth | 18 | 17 | 16 | 15 | 14 | 13 | 12 | 11 |
| Strip Mesial [mm] | 0,2 | | | 0,3 | 0,2 | 0,2 | | 0,2 |
| Strip Distal [mm] | | | | | 0,2 | | | |
| Inclination [°] | -1,2 | 8 | -10,8 | -1,5 | -14,2 | -9,9 | -6,2 | -5,8 |
| Inclination +/- [°] | 1,5 | | | | | 0,1 | 0,6 | 1,4 |
| Angulation [°] | -2 | -7,2 | 1,4 | 10,7 | 7,3 | 11,7 | 6,2 | -4,1 |
| Angulation +/- [°] | 0,1 | | | | | -0,2 | -0,1 | |
| Rotation +/- [°] | -0,1 | | | | 0,1 | -0,8 | -1,2 | 0,3 |
| Mesial +/- [mm] | 0,03 | | -0,02 | | -0,04 | -0,02 | | -0,01 |
| Vestibular +/- [mm] | 0,13 | | -0,02 | | 0,01 | -0,03 | 0,06 | 0,12 |
| Occlusal +/- [mm] | -0,03 | | -0,04 | | -0,01 | -0,03 | | -0,02 |

| Maxilla | | | | | | | | |
|---|---|---|---|---|---|---|---|---|
| Tooth | 21 | 22 | 23 | 24 | 25 | 26 | 27 | 28 |
| Strip Mesial [mm] | 0,2 | | | 0,2 | 0,3 | | | |
| Strip Distal [mm] | | | 0,3 | 0,2 | | | | |
| Inclination [°] | -1,2 | -2,9 | -9,6 | -17,1 | -8,4 | -14,3 | 7,8 | |
| Inclination +/- [°] | 1,5 | 0,9 | 0,4 | | | | | |
| Angulation [°] | -2 | -0,2 | 11,7 | 8,1 | 11 | 2,4 | -4 | |
| Angulation +/- [°] | 0,1 | -0,1 | -0,3 | | | | | |
| Rotation +/- [°] | -0,1 | -1,5 | -1,3 | | | | | |
| Mesial +/- [mm] | 0,03 | 0,04 | -0,02 | -0,03 | | | | |
| Vestibular +/- [mm] | 0,13 | 0,07 | -0,02 | 0,01 | | | | |
| Occlusal +/- [mm] | -0,03 | 0,02 | -0,04 | -0,01 | | | | |

Fig. 44L continued

| Mandible | | | | | | | | |
|---|---|---|---|---|---|---|---|---|
| Tooth | 48 | 47 | 46 | 45 | 44 | 43 | 42 | 41 |
| Strip Mesial [mm] | | | | | | | | |
| Strip Distal [mm] | | | | | | | | |
| Inclination [°] | | -31,1 | -30,8 | -25,1 | -16,1 | -5,7 | 9 | 9,4 |
| Inclination +/- [°] | | | | | | -0,2 | -0,5 | -0,2 |
| Angulation [°] | | 6,5 | 14,9 | 7,6 | 4,3 | 3,7 | -1,9 | -1,2 |
| Angulation +/- [°] | | | | | | | 0,1 | |
| Rotation +/- [°] | | | | | | 0,3 | 0,3 | -0,1 |
| Mesial +/- [mm] | | | | | | | | 0,01 |
| Vestibular +/- [mm] | | | | | | 0,05 | | 0,06 |
| Occlusal +/- [mm] | | | | | | -0,04 | -0,03 | |

| Mandible | | | | | | | | |
|---|---|---|---|---|---|---|---|---|
| Tooth | 31 | 32 | 33 | 34 | 35 | 36 | 37 | 38 |
| Strip Mesial [mm] | | | | | | | | |
| Strip Distal [mm] | | | | | | | | |
| Inclination [°] | 10,6 | 9,7 | -6,8 | -14,1 | -21,2 | -32,8 | -25,5 | |
| Inclination +/- | -0,2 | -0,2 | | | | | | |
| Angulation [°] | 1,6 | -2,4 | 10,2 | 12,2 | 3,5 | 17,9 | 5,5 | |
| Angulation +/- [°] | | | | | | | | |
| Rotation +/- [°] | | 0,1 | | | | | | |
| Mesial +/- [mm] | | | | | | | | |
| Vestibular +/- [mm] | 0,04 | 0,02 | 0,04 | | | | | |
| Occlusal +/- [mm] | | -0,03 | -0,04 | | | | | |

Fig. 44M

| Maxilla | | | | | | | | |
|---|---|---|---|---|---|---|---|---|
| Tooth | 18 | 17 | 16 | 15 | 14 | 13 | 12 | 11 |
| Strip Mesial [mm] | 0,2 | | | 0,3 | 0,2 | 0,2 | | 0,2 |
| Strip Distal [mm] | | | | | 0,2 | 0,2 | | |
| Inclination [°] | 1 | 8 | -10,8 | -1,5 | -14,2 | -9,8 | -5,4 | -3,8 |
| Inclination +/- [°] | 2,2 | | 0,5 | | | 0,1 | 0,8 | 2 |
| Angulation [°] | -1,8 | -7,2 | 1,4 | 10,7 | 7,3 | 11,4 | 6 | -4 |
| Angulation +/- [°] | 0,2 | | -0,5 | | | -0,4 | -0,2 | |
| Rotation +/- [°] | -0,2 | | -2 | | 0,1 | -1,2 | -1,8 | 0,4 |
| Mesial +/- [mm] | 0,04 | 0,06 | -0,02 | -0,05 | -0,05 | -0,04 | | -0,02 |
| Vestibular +/- [mm] | 0,2 | 0,1 | -0,12 | 0,02 | 0,01 | -0,04 | 0,09 | 0,18 |
| Occlusal +/- [mm] | -0,06 | 0,03 | -0,05 | -0,01 | -0,01 | -0,05 | -0,01 | -0,04 |

| Maxilla | | | | | | | | |
|---|---|---|---|---|---|---|---|---|
| Tooth | 21 | 22 | 23 | 24 | 25 | 26 | 27 | 28 |
| Strip Mesial [mm] | 0,2 | | 0,3 | 0,2 | 0,3 | | | |
| Strip Distal [mm] | | | | 0,2 | | | | |
| Inclination [°] | 1 | -1,6 | -9 | -17,1 | -8,4 | -14,3 | 7,8 | |
| Inclination +/- [°] | 2,2 | 1,4 | 0,5 | | | | | |
| Angulation [°] | -1,8 | -0,5 | 11,3 | 8,1 | 11 | 2,4 | -4 | |
| Angulation +/- [°] | 0,2 | -0,2 | -0,5 | | | | | |
| Rotation +/- [°] | -0,2 | -2,2 | -2 | 0,1 | | | | |
| Mesial +/- [mm] | 0,04 | 0,06 | -0,02 | -0,05 | | | | |
| Vestibular +/- [mm] | 0,2 | 0,1 | -0,12 | 0,02 | | | | |
| Occlusal +/- [mm] | -0,06 | 0,03 | -0,05 | -0,01 | | | | |

Fig. 44M continued

| Mandible | | | | | | | | |
|---|---|---|---|---|---|---|---|---|
| Tooth | 48 | 47 | 46 | 45 | 44 | 43 | 42 | 41 |
| Strip Mesial [mm] | | | | | | | | |
| Strip Distal [mm] | | | | | | | | |
| Inclination [°] | | -31,1 | -30,8 | -25,1 | -16,1 | -5,9 | 8,2 | 9 |
| Inclination +/- [°] | | | | | | -0,3 | -0,8 | -0,4 |
| Angulation [°] | | 6,5 | 14,9 | 7,6 | 4,3 | 3,8 | -1,8 | -1,2 |
| Angulation +/- [°] | | | | | | 0,1 | 0,1 | |
| Rotation +/- [°] | | | | | | 0,5 | 0,4 | -0,1 |
| Mesial +/- [mm] | | | | | | 0,01 | 0,01 | 0,01 |
| Vestibular +/- [mm] | | | | | | 0,07 | | 0,09 |
| Occlusal +/- [mm] | | | | | | -0,06 | -0,05 | -0,01 |

| Mandible | | | | | | | | |
|---|---|---|---|---|---|---|---|---|
| Tooth | 31 | 32 | 33 | 34 | 35 | 36 | 37 | 38 |
| Strip Mesial [mm] | | | | | | | | |
| Strip Distal [mm] | | | | | | | | |
| Inclination [°] | 10,3 | 9,3 | -6,8 | -14,1 | -21,2 | -32,8 | -25,5 | |
| Inclination +/- | -0,3 | -0,4 | | | | | | |
| Angulation [°] | 1,5 | -2,4 | 10,2 | 12,2 | 3,5 | 17,9 | 5,5 | |
| Angulation +/- | -0,1 | | | | | | | |
| Rotation +/- [°] | | 0,1 | | | | | | |
| Mesial +/- [mm] | | | 0,01 | | | | | |
| Vestibular +/- [mm] | 0,06 | 0,02 | 0,05 | | | | | |
| Occlusal +/- [r | -0,01 | -0,04 | -0,06 | | | | | |

Fig. 44N

| Maxilla | | | | | | | | |
|---|---|---|---|---|---|---|---|---|
| Tooth | 18 | 17 | 16 | 15 | 14 | 13 | 12 | 11 |
| Strip Mesial [mm] | 0,2 | | | 0,3 | 0,2 | 0,2 | | 0,2 |
| Strip Distal [mm] | | | | | 0,2 | | | |
| Inclination [°] | | 8 | -10,8 | -1,5 | -14,2 | -9,8 | -5,4 | -3,8 |
| Inclination +/- [°] | 18,7 | | 5 | | 0,1 | 1,1 | 7,1 | 17,6 |
| Angulation [°] | -1,8 | -7,2 | 1,4 | 10,7 | 7,3 | 11,4 | 6 | -4 |
| Angulation +/- [°] | 1,7 | | -3,5 | | | -3,1 | -1,1 | -0,1 |
| Rotation +/- [°] | -1,6 | | -17,1 | | 0,7 | -10,2 | -15,3 | 3,3 |
| Mesial +/- [mm] | 0,43 | 0,57 | -0,54 | -0,41 | -0,47 | -0,62 | 0,17 | -0,03 |
| Vestibular +/- [mm] | 1,55 | 0,81 | -0,51 | 0,15 | 0,09 | -0,28 | 0,77 | 1,48 |
| Occlusal +/- [mm] | -0,5 | 0,24 | -0,48 | -0,07 | -0,08 | -0,48 | -0,05 | -0,35 |

| Maxilla | | | | | | | | |
|---|---|---|---|---|---|---|---|---|
| Tooth | 21 | 22 | 23 | 24 | 25 | 26 | 27 | 28 |
| Strip Mesial [mm] | 0,2 | | | 0,2 | 0,3 | | | |
| Strip Distal [mm] | | | 0,3 | 0,2 | | | | |
| Inclination [°] | 1 | -1,6 | -9 | -17,1 | -8,4 | -14,3 | 7,8 | |
| Inclination +/- [°] | 18,7 | 11,7 | 5 | | | | | |
| Angulation [°] | -1,8 | -0,5 | 11,3 | 8,1 | 11 | 2,4 | -4 | |
| Angulation +/- [°] | 1,7 | -0,4 | -3,5 | | | | | |
| Rotation +/- [°] | -1,6 | -18,9 | -17,1 | 0,6 | | | | |
| Mesial +/- [mm] | 0,43 | 0,57 | -0,54 | -0,41 | | | | |
| Vestibular +/- [mm] | 1,55 | 0,81 | -0,51 | 0,15 | | | | |
| Occlusal +/- [mm] | -0,5 | 0,24 | -0,48 | -0,07 | | | | |

Fig. 44N continued

| Mandible | | | | | | | | |
|---|---|---|---|---|---|---|---|---|
| Tooth | 48 | 47 | 46 | 45 | 44 | 43 | 42 | 41 |
| Strip Mesial [mm] | | | | | | | | |
| Strip Distal [mm] | | | | | | | | |
| Inclination [°] | | -31,1 | -30,8 | -25,1 | -16,1 | -5,9 | 8,2 | 9 |
| Inclination +/- [°] | | | | | | -2,3 | -6,9 | -3,1 |
| Angulation [°] | | 6,5 | 14,9 | 7,6 | 4,3 | 3,8 | -1,8 | -1,2 |
| Angulation +/- [°] | | | | | | 0,7 | 1,2 | 0,4 |
| Rotation +/- [°] | | | | | | 4,1 | 3,2 | -1 |
| Mesial +/- [mm] | | | -0,1 | | | | 0,01 | 0,1 |
| Vestibular +/- [mm] | | | 0,05 | | | 0,63 | 0,15 | 0,78 |
| Occlusal +/- [mm] | | | -0,49 | | | -0,48 | -0,35 | |

| Mandible | | | | | | | | |
|---|---|---|---|---|---|---|---|---|
| Tooth | 31 | 32 | 33 | 34 | 35 | 36 | 37 | 38 |
| Strip Mesial [mm] | | | | | | | | |
| Strip Distal [mm] | | | | | | | | |
| Inclination [°] | 10,3 | 9,3 | -6,8 | -14,1 | -21,2 | -32,8 | -25,5 | |
| Inclination +/- | -3 | -3,1 | | | | | | |
| Angulation [°] | 1,5 | -2,4 | 10,2 | 12,2 | 3,5 | 17,9 | 5,5 | |
| Angulation +/- [°] | -0,5 | -0,1 | | | | | | |
| Rotation +/- [°] | 0,3 | 0,9 | -0,1 | | | | | |
| Mesial +/- [mm] | | | 0,05 | | | | | |
| Vestibular +/- [mm] | 0,48 | 0,22 | 0,44 | | | | | |
| Occlusal +/- [r | -0,02 | -0,34 | -0,49 | | | | | |

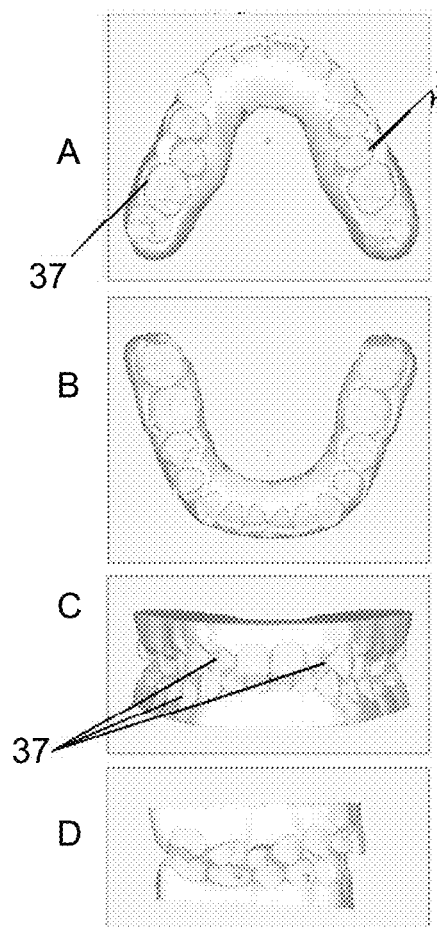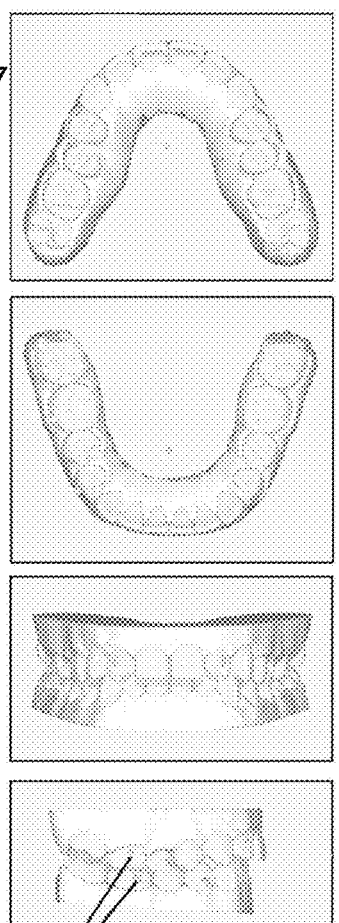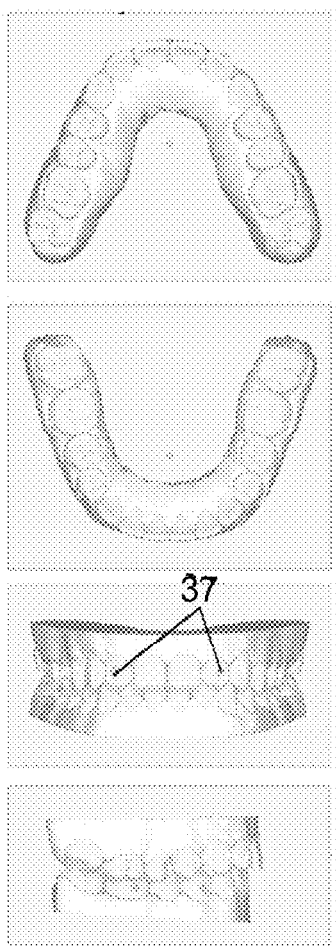

Fig. 49　　　　Fig. 50　　　　Fig. 51
A 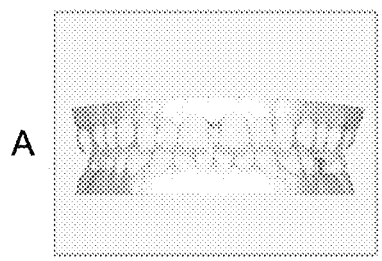 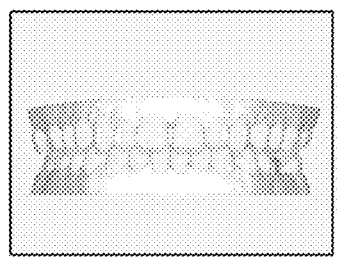 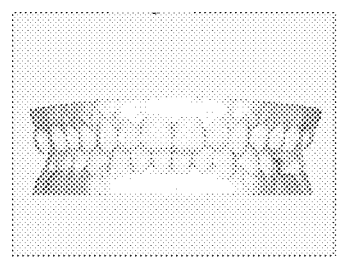
B 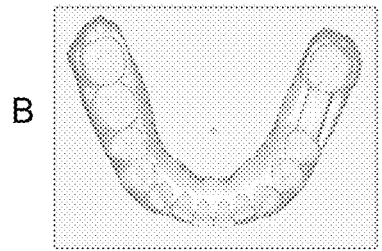 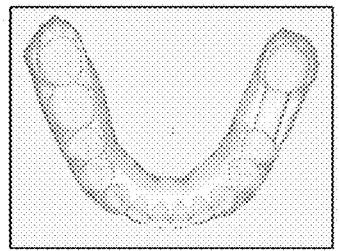 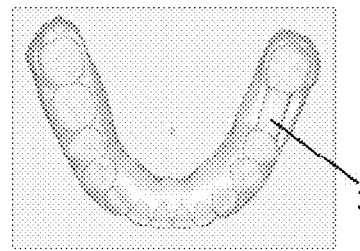 34
C 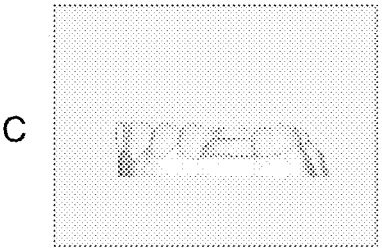 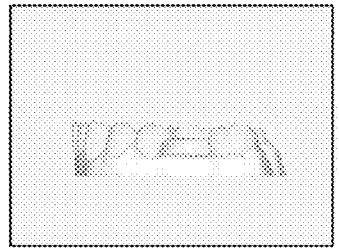 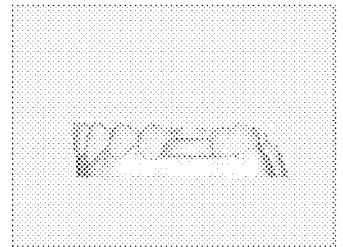
D 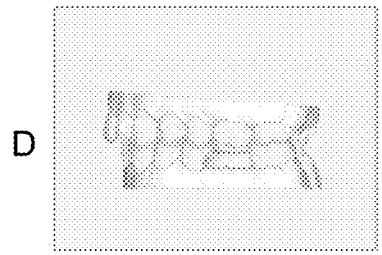 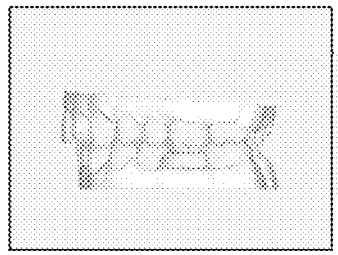 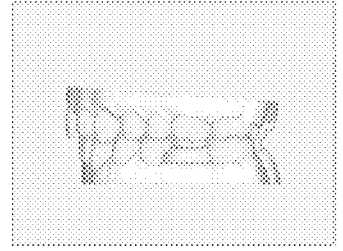
↑　　　　↑　　　　↑
8　　　　8　　　　8

AUTOMATIC CREATION OF A VIRTUAL MODEL AND AN ORTHODONTIC TREATMENT PLAN

CROSS REFERENCE TO RELATED APPLICATIONS

Applicant claims priority under 35 U.S.C. § 119 of PCT/EP2020/087806 filed Dec. 23, 2020, the disclosure of which is incorporated by reference.

TECHNICAL FIELD

In one aspect, the present invention relates to a system and a (computer-implemented) method for creating a virtual model of at least part of a dentition of a patient. In another aspect, the present invention relates to a system and a (computer-implemented) method for creating an orthodontic treatment plan.

BACKGROUND

A dentition of a patient is the arrangement of teeth on the lower jaw (mandible) or the upper jaw (maxilla). An occlusal state (or bite pattern) is defined by a given dentition on the mandible, a given dentition on the maxilla and the relative arrangement of mandible and maxilla (jaw alignment). Abnormal arrangement of teeth in a dentition can lead to misaligned occlusal states (malocclusion or misalignment). The presence of a misaligned state is also called an orthodontic condition.

Treating a certain orthodontic condition via an alignment of a malocclusion and/or a misalignment, respectively, by transferring a first occlusal state into a second occlusal state (that in general differs from the first occlusal state and can be called target state) can be of medical and/or aesthetic interest. It is possible to balance out jaw misalignments and/or malocclusions for a specific orthodontic condition with respect to medical reasons and/or realign an occlusal state for the sake of—particularly subjective—optical advantages with respect to a patient's cosmetic correction (generated, e.g., by an orthodontic appliance like an aligner). In general, an aesthetic dental condition can be seen as an orthodontic condition, even if there is no medical necessity present. It can also be desired to maintain a specific occlusal state, e.g., via a permanent or removable lingual retainer.

A virtual model of at least part of a dentition of a patient is a prerequisite for being able to treat a dental and/or orthodontic condition. Such a virtual model is created based on a digital data record representing a three dimensional (3d) model in the way of a 3d surface of at least part of a dentition of a patient. Usually, the digital data record is obtained by an intraoral scan or a scan of a model of the dentition (e.g., obtained by creating an impression of the dentition). In the 3d model, the visible parts of the teeth and the gingiva is encoded by way of a single of er surface without any information where the gingiva ends and a visible part of a tooth begins or information about the individual teeth in isolation. In order to enable a system or computer implemented method to understand a patient's dentition it is necessary to create a virtual model in which each visible part of a tooth is represented by its own 3d surface and the gingiva is represented by its own 3d surface (in other words, the visible parts of the teeth are separated from each other and from the gingiva). Sometimes, the process for arriving at such a virtual model from a 3d representation is called "segmentation". This term is not to be confused with the segmentation of data into data segments which will be described with respect to the invention. Therefore, in this disclosure the term "separation" will be used to avoid misunderstandings.

The set of transformations necessary to change a first dentition into a second dentition (also called target dentition), and thereby a first occlusal state into a second occlusal state, and/or to retain an occlusal state is called treatment plan.

In order to facilitate diagnosing and identifying a treatment plan for an orthodontic condition at the site of a practitioner it has been suggested to use a server configured to receive patent data through a website and to employ artificial intelligence (AI) to automatize diagnosing and identification of a treatment plan. By way of example, U.S. Pat. No. 8,856,053 B2 describes such a system. In order to be able to identify a diagnosis and a treatment plan a database has to be provided during inference operation of the system. The database comprises, or has access to, information derived from textbooks and scientific literature and dynamic results derived from ongoing and completed patient treatments.

Another system which needs a database during inference operation is described in EP 1 723 589 B1. The database comprises a compendium of data related to each of a plurality of dental patient treatment histories. A data mining technique is employed for interrogating the database to provide a treatment plan for a specific patient's malocclusion.

Yet another system using an artificial intelligence technique relying on a database is disclosed in US 2019/0192258 A1. Patient data obtained using an intraoral scanner is compared to different groups of grouped data of the database to determine to which group the scanned patient data belong. Based on the selected group of data of the database a treatment plan is created.

All systems in which artificial intelligence requires access to a database during inference operation (i.e., after an initial training phase has been completed) are relatively slow in creating a treatment plan after having been provided with patient data such that it would be unreasonable for a patient to wait at a user's (e.g., dentist's) office after scanning of the patient's data. Also, these systems are inflexible when it comes to interpreting patient data which is not closely related to data provided by the database. The implementation of a database is very hardware-intensive, at least for large databases, which are needed to store a reasonable amount of data to allow an artificial intelligence to create a treatment plan.

EP 2 258 303 B1 teaches a treatment planning system in which orthodontist-derived parameters for treatment of a malocclusion can be translated into a design of an orthodontic appliance, allegedly, while the patient is in the chair, i.e., allegedly in real time. The idea of this patent is to use virtual 3d models of template objects, each object corresponding to a tooth, which are superimposed on a virtual model of a patient's dentition. The virtual model of the dentition comprises teeth separated from each other and from the gingiva, such that they can be individually manipulated permitting individual, customized tooth positioning on a tooth-by-tooth basis. A target archform is calculated and can be shaped to meet anatomical constraints of the patient. After the initial archform is designed, the user can position the teeth on the archform as deemed appropriate on a tooth-by-tooth basis. The treatment planning software thus enables the movement of the virtual tooth objects onto an archform which may represent, at least in part, a proposed treatment objective for the patient. With respect to computing infrastructure, this patent proposes that a clinic has a back office server work station having its own user interface, including a monitor. The back office server executes an orthodontic treatment planning software program. The software obtains the 3d digital data of the patient's teeth from a scanning node and displays the model for the orthodontist. The treatment planning software includes features to enable the orthodontist to manipulate the model to plan treatment for the patient. For example, the orthodontist can select an archform for the teeth and manipulate individual tooth positions relative to the archform to arrive at a desired or target situation for the patient. The software moves the virtual teeth in accordance with the selections of the orthodontist. The software also allows the orthodontist to selectively place virtual brackets on the tooth models and to design a customized archwire for the patient given the selected bracket positions. When the orthodontist has finished designing the orthodontic appliance for the patient, digital information regarding the patient, the malocclusion, and a desired treatment plan for the patient are sent over a communications medium to an appliance service center. A customized orthodontic archwire and a device for placement of the brackets on the teeth at the selected location is manufactured at the service center and shipped to the clinic. The use of template objects makes it hard to adjust to the shape of teeth of a particular individual dentition. It is not possible to directly manufacture an appliance at the orthodontists site.

A system using an artificial intelligence technique employing a neuronal network is described in EP 3 359 080 B1. Tooth movement is decomposed into different types of movement, such as "tip", "rotation around long axis", "bodily movement", . . . . The neuronal network is trained using treated cases as a learning set. Employing a single neuronal network results in a very long time for processing and operation has to be stopped if the neuronal network becomes unstable.

Further examples of orthodontic treatment planning based on neuronal networks are given in:
"Khanagar S B et al., Scope and performance of artificial intelligence technology in orthodontic diagnosis, treatment planning, and clinical decision-making—A systematic review. Journal of Dental Sciences; https://doi.org/10.1016/j.jds.2020.05.022".
"Asiri S N et al., Applications of artificial intelligence and machine learning in orthodontics. APOS Trends Orthod 2020, 10(1):17-24".
"Torsdagli N et al., Deep Geodesic Learning for Segmentation and Anatomical Landmarking. IEEE Trans Med Imaging".
"Hwang, Jae-Joon et al., An overview of deep learning in the field of dentistry. Imaging Sci Dent 2019, 49:1-7".
"Li P et al., Orthodontic Treatment Planning based on Artificial Neural Networks. Sci Rep 9, 2037 (2019)." See also the supplemental information which is available for this report.

It can sometimes be necessary or simply desired that a user, e.g., a doctor, can edit or modify an automatically generated treatment plan. Such a system is disclosed in US 2020/0000555 A1.

Automatic separation, i.e., automatic identification and isolation of visible parts of a tooth from the gingiva has been a developing field (cf. the discussion of prior art in WO 2018/101923 A1 and document US 2019/0357997 A1).

WO 2020/127824 A1 shows a fixed lingual retainer.

What is needed is a system and method which do not require access to a database during inference operation, is faster creating a virtual model and, preferably, at least one treatment plan after having been provided with patient data and is more flexible when it comes to interpreting new patient data, a computer program to cause a computer to embody such a system or to carry out such a method and a process which is able to obtain an appliance faster than the systems and methods of the prior art as well as a computer-readable medium and a data carrier signal.

SUMMARY OF INVENTION

It is an object of the invention to provide a system and method which are faster when creating a virtual model and, preferably, at least one treatment plan after having been provided with patient data.

It is another object of the invention to provide a system and method which are more flexible when it comes to interpreting new patient data.

Still other objects and advantages of the invention will in part be obvious and will in part be apparent from the specification and drawings.

One object of the disclosure relates to a system and a method which are able to create a virtual model after having been provided with patient data faster than the systems and methods of the prior art, preferably in real time. Human input can be minimized during creation of the virtual model, ideally, no human input is necessary at all, which makes the system and method independent of the availability of trained human operators and reduces the time necessary for creating the virtual model.

Still another object of the disclosure relates to a computer program which, when the program is executed by a computer having at least:
at least one computing; device which is configured to execute in parallel a plurality of processes
at least one shared memory device which can be accessed by the at least one computing device
at least one first interface for receiving a digital data record and for storing the digital data record in the at least one shared memory device
at least one second interface for outputting data causes the computer to be configured as a system as described herein, or to carry out the method as described herein.

Still another object of the disclosure relates to a process which is able to obtain an appliance faster than the systems and methods of the prior art. Examples of appliances which can be obtained by such a process are an aligner, an orthodontic bracket and a fixed lingual retainer.

Still another object of the disclosure relates to a computer-readable medium comprising instructions which, when executed by a computer, cause the computer to be configured as a system as described herein or to carry out the method as described herein.

Still another object of the disclosure relates to a data carrier signal carrying:
the at least one virtual model created by a system as described herein and/or
the at least one treatment plan as described herein and/or
the computer program as described herein the at least one treatment plan as described herein or the computer program as described herein.

Structure of the following parts of the description (only the beginning paragraph of each part is referenced):
paragraph 28—terminology used in this disclosure
paragraph 48—configuration and structure of different embodiments of the system and method paragraph 108—operation of different embodiments of system and method
paragraph 152—use of categorical constructs
paragraph 190—training of the system and method
paragraph 228—figure description It is to be understood that the above-referenced sections are not meant to be read in isolation from each after but form a coherent part of the description of embodiments of the invention. Furthermore, the discussion of the background of the invention is understood to be part of the disclosure of the invention.

Embodiments of the invention are defined in the dependent claims.

DESCRIPTION OF EMBODIMENTS

Terminology:

A "dentition" of a patient is the arrangement of teeth on the lower jaw (mandible) and/or the upper jaw (maxilla).

An "occlusal state" (or bite pattern) is defined by a given dentition on the mandible, a given dentition on the maxilla, and the relative arrangement of mandible and maxilla (jaw alignment), in other words, it is the way the teeth meet when the mandible and maxilla come together.

A "three dimensional (3d) model" represented by a digital data record which is used as input for the system and method of the invention is understood to show at least part of a dentition of a patient in the way of a 3d surface of that part wherein the 3d surface encodes die visible parts of the teeth and the gingiva as a single surface without any information where the gingiva ends and a visible part of a tooth begins and without information about the individual teeth in isolation (unseparated 3d surface).

A "virtual model", as an output of a system and method according to the invention, encodes at least the visible parts of teeth (those parts of teeth which protrude from gingiva) such that the visible parts of teeth are separated from each other and the gingiva, i.e., they are represented by individual 3d surfaces. In some embodiments the virtual model might have defective areas where, e.g., information of the inputted 3d model is missing or is not of sufficient quality, in other words, a virtual model need not be a perfect representation of the teeth shown. In other embodiments the virtual model might encode more information about the teeth than was represented by the inputted 3d model if supplemental information is used by the system and method.

A "supplemental data record" represents information about at least part of the dentition which is represented by the 3d model which is not, or not completely, represented in the digital data record such as, e.g., parts of teeth covered by gingiva, or represents information which is represented in the digital data record in a different way, e.g., photos made with a camera to supplement the information provided by the scanner used to generate the 3d model. A supplemental data record can be provided, e.g., in the form of analog or digitalized photos made with an optical camera, X-ray images, CT scans, written description, . . . .

A "treatment plan" gives information about the transformations necessary to transfer a first occlusal state of an orthodontic condition (also called starting dentition) into a second occlusal state (that differs from the first occlusal state, resulting in a different orthodontic condition, also called target dentition) by way of a sequence of transformations (resulting in intermediary dentitions) and/or to retain an occlusal state of the orthodontic condition, due to medical and/or aesthetic interest. A treatment plan can provide the information necessary for a manufacturing device to directly produce the at least one appliance prescribed by the transformations listed in the treatment plan and/or for a human operator to use a manufacturing device to produce the at least one appliance prescribed by the transformations listed in the treatment plan. The treatment plan can, e.g., be provided as a binary file and/or an ASCII file.

An "anatomical sub-structure" is understood to encompass any structure that might be present in a 3d anatomical model or in supplemental information that refers to an anatomical representation. By way of example, in this disclosure, anatomical sub-structures are teeth, parts of teeth and gingiva, but can also mean artificial sub-structures that do not form a natural part of a dentition, such as dental fillings or implants.

The term "appliance" refers to any orthodontic device which is put in place by orthodontists to gradually reposition teeth to a desired alignment or to retain a desired alignment. There are "fixed appliances" (e.g., bands, wires, brackets, lingual retainers) that are bonded to the teeth and are not supposed to be removed by the patient, and "removable appliances" which can be removed by a patient (e.g., for cleaning), such as aligners.

The term "configurational state of an anatomical sub-structure" means a specific rotational state and/or a specific spatial position of that anatomical substructure.

The term "transformation" means any modification of the shape (e.g., interproximal reduction—IPR, an IPR is the practice of mechanically removing enamel from between teeth to achieve orthodontic ends, such as to correct crowding, or reshape the contact area between neighboring teeth) and/or change of configurational state of an anatomical sub-structure (e.g., torquing or shifting a tooth or a group of teeth).

The term "data analysis" is understood to encompass inspecting, transforming, modeling, interpreting, classifying, visualizing data for any kind of purpose.

The term "CPU" encompasses any processor which performs operations on data such as a central processing unit of a system, a co-processor, a Graphics Processing Unit, a Vision Processing Unit, a Tensor Processing Unit, an FPGA, an ASIC, a Neural Processing Unit, . . . .

The term "thread of execution" (sometimes simply referred to as "thread") is defined as the smallest sequence of programmed instructions that can be managed by a scheduler of an operating system. Another term for "thread" used in this disclosure is "sub-process". By way of example, each thread of execution can be executed by one processing entity of a CPU. A CPU can provide a number of processing entities to the operating system of the system.

The term "machine learning method" is meant to signify the ability of a system to achieve a desired performance, at least partially by exposure to data without the need to follow explicitly programmed instructions, e.g., relying on patterns and/or inference instead. Machine learning methods include the use of artificial neuronal networks (in short "ANNs", also called neuronal networks in this disclosure).

It is to be understood that in the context of this disclosure "different" neuronal networks can mean networks which differ in type (e.g., classical or Quantum CNNs, RNNs such as LSTMs, ARTs, . . . , and/or in the specific setup of the network (e.g., number of layers, types of layers, number of neurons per layer, connections between neurons, number of synaptic weights other parameters of the network, . . . ).

The term "random signal" means a signal that takes on random values at any given time instant and can only be modeled stochastically.

The term "real time" is defined pursuant to the norm DIN ISO/IEC 2382 as the operation of a computing system in which programs for processing data are always ready for operation in such a way that the processing results are available within a predetermined period of time. If a client-server architecture is present it is understood to mean that processing of digital information and/or transmitting digital information between at least one client program and at least one server does not include a lag that is induced by a preparation of the digital information within the at least one client program by the patient and/or technical staff for instance.

Those terms in the present disclosure which have not been explicitly defined are to be given their usual meaning in the art.

With respect to the mathematical language of category theory the usual terminology is applied. For a documentation of category theory, e.g., the following texts can be consulted:

Saunders Mac Lane, "Categories for the Working Mathematician", Second Edition, 1998 Springer Robert Goldblatt, "Topoi", revised edition, 2006 Dover Publications David I. Spivak, "Category Theory for the Sciences", 2014 The MIT Press Configuration and structure of system:

The system comprises:

at least one first interface for receiving a data record representing a 3d representation of an outer surface of at least part of a dentition of a patient at least one second interface for outputting output data at least one computing device which is configured to execute in parallel a plurality of processes and to which the at least one first interface and the at least one second interface are connected and which is configured to:

receive data from the at least one first interface send data to the at least one second interface at least one shared memory device into which data can be written and from which data can be read and which can be accessed by the at least one computing device The system and method is faster than the prior art which use databases, due to the plurality of parallelly executed processes comprising computation modules which is a faster process than executing complex database queries and a less hardware intensive process because big databases tend to be very hardware intensive and slow.

By way of example, the at least one first interface can be a data interface for receiving digital or analog data (e.g., a CAD file such as an object file and/or an STL file, and/or an image file and/or an analog image and/or an ASCII file). Alternatively or in addition, it can be configured to be connectable to a sensor for capturing data (e.g., an optical sensor like a camera, a scanning device, . . . ) or to comprise at least one such sensor. In addition or alternatively, the at least one first interface can be configured to receive pre-stored data or a data stream provided by other means, e.g., via a communication network such as the internet.

By way of example, the at least one second interface can be configured to be connectable to an output device for outputting data (e.g., a digital signal output, a display for displaying optical data, a loudspeaker for outputting sound, . . . ) or comprises at least one such output device. In addition or alternatively, the at least one second interface can be configured to provide output data to a storage device or as a data stream, e.g., via a communication network such as the internet. Regarding the contents of the output data, the output data can include, e.g., files, spoken language, pictorial or video data in clear format or encoded. In some embodiments command signals can be outputted, in addition or alternatively, which can be used to command actions by a device reading the output data, e.g., command signals for producing appliances. The output can comprise, e.g., a CAD file such as an object file and/or an STL file and/or an image file and/or an analog image and/or an ASCII file. The virtual model created by the system can be made available via the at least one second interface and/or can be used by the system for further purposes, e.g., for creating at least one treatment plan.

The at least one first and second interface can be realized by the same physical component or by physically different components.

The at least one shared memory device (in short: shared memory), into which data can be written and read from, can be any suitable computer memory. It is used whenever different processes or threads access the same data. In some embodiments all of the components of the system and method have access to the shared memory.

The at least one computing device of the system can comprise one or more CPUs wherein it should be understood that each CPU provides a number of processing entities to the operating system of the system.

The initial configuration of the system, i.e., providing all of the components with the described functionalities, could be done by providing a computer program (e.g., using configuration files) which, when executed on a system or by a method, configures the system in the desired manner or the configuration could be provided encoded in hardware, e.g., in the form of FPGA or ASICS. Of course, an approach in which some of the configuration is done by software and other parts are hardware encoded can also be envisioned.

Initial configuration of the system and method can include, e.g., configuring the number of computation modules, connections between them and, possibly, collecting the computation modules into groups according to their intended functionalities and/or into computational groups and/or meta-groups.

By way of example, the following groups could be configured:

a group called "REPRESENTATION STL" which is to be trained to represent different anatomical sub-structures that might appear in a 3d model (e.g., an STL-representation) of a human's dentition such as different teeth and gingiva a group called "REPRESENTATION XRAY" which is to be trained to represent different anatomical sub-structures that might appear in an X-ray-representation of a human's dentition such as different teeth and gingiva a group called "SEPARATION STL" which is to be trained to accomplish separation of the visible parts of teeth and gingiva in a 3d model (e.g., an STL-representation) of a human's dentition. The group marked "SEPARATION XRAY" is to be trained to accomplish separation of (possibly both, visible and invisible parts of) teeth and gingiva a group called "SUPPLEMENT" which is to be trained to supplement the information gained from the STL-representation with the information from the X-ray-representation, if provided a group called "VIRTUAL MODEL CREATION" which is to be trained to create the virtual model a group called "TARGET DENTITIONS" which is to be trained to represent different target dentitions a group called "TREATMENT PLAN CREATION" which is to be trained to determine the necessary transformations to transform a given dentition into a target dentition (treatment plan)

a group called "PRODUCTION FILES CREATION" which is to be trained to create production files for the production of orthodontic appliances to the treatment plan Alternatively, some or all of the above-mentioned groups could be created by the system itself during training instead of by initially configuring the system.

A possible hardware for implementation of the invention is taught in US 2019/243795 A1 the contents of which is hereby incorporated in its entirety by reference. Alternatively, other hardware known in the art can be used.

The at least one computing device is configured to execute in parallel a plurality of processes comprising at least a plurality of processes in the form of groups of computation modules (in the following in short: computation module(s)), each group comprising at least one computation module. Preferably there are at least more than ten, in particular more than a hundred or more than a thousand parallelly executed computation modules configured in the system and method. By way of example, a total number of about 200000 to about 1000000 computation modules could be configured which could be running in about 200000 threads to about 1000000 (only a few hundred of them will be active at any given time) in about 200 to 400 cores. In some embodiments, groups of computation modules can be grouped into computational groups, each computational group comprising a plurality of groups of computation modules, which can be grouped into meta-groups, each meta-group comprising a plurality of computational groups.

Data, analysis inside a computation module is executed using a machine learning method using at least one artificial neuronal network. Any kind of neuronal network known in the art might be configured in a given computation module and different computation modules can have different neuronal networks configured. Output of a specific computation module can be inputted to other computation modules and/or be sent to the shared memory and/or be sent to data hub process(es), if present. It is an advantage of the invention that, usually, the neuronal networks employed in the computation modules can be relatively shallow in the sense of comprising a small to moderate number of layers, e.g., 3 to 5 layers, and can comprise relatively few artificial neurons in total, e.g., 5 to 150 neurons per layer, in some embodiments up to 1000 neurons with a number of synaptic weights (e.g., of double format type) of about 1000, 10000-50000 or 100000.

It must be stressed that in the following description the language sometimes makes use of biological concepts. This, however, only serves to make description easier. In reality, all of the processes are configured as computer code for execution by at least one CPU and the concepts discussed in the following such as synapse, axon, neuron body, . . . could be, e.g., classes in an object-based programming language, such as C++ or Java.

A single computation module comprises at least one artificial neuronal network of any known type (such as a MfNN, RNN, LSTM, . . . ) which comprises a plurality of artificial neurons. Each artificial neuron (in the following in short: "neuron") has at least one (usually a plurality of) synapse for obtaining a signal and at least one axon for sending a signal (in some embodiments a single axon can have a plurality of breachings). Usually, each neuron obtains a plurality of signals from other neurons or from an input interface of the neuronal network via a plurality of synapses and sends a single signal to a plurality of other neurons or to an output interface of the neuronal network. A neuron body is arranged between the synapse(s) and the axon(s) and comprises at least an integration function (according to the art) for integrating the obtained signals and an activation function (according to the art) to decide whether a signal is to be sent by this neuron in reaction to the obtained signals. Any activation function of the art can be used such as a step-function, a sigmoid function, . . . .

As is known in the art, the signals obtained via the synapses can be weighted by weight factors (synaptic weights). Individual weight factors can be provided by a weight storage which might form part of a computation module or could be configured separately from the computation modules and, in the latter case, could provide individual weights to a plurality (or possibly all) of the neuronal networks of the computation modules, e.g., via the shared memory and/or a routing process. These weights can be determined as known in the art, e.g., during a training phase by modifying a pre-given set of weights such that a desired result is given by the neuronal network with a required accuracy. Other known techniques could be used.

As is known in the art, input signals and weights and output signals do not have to be in the format of scalars but can be defined as vectors or higher-dimensional tensors.

In some embodiments the neuron body can comprise a receptor for obtaining a random signal which is generated outside of the neuronal network (and, preferably, outside of the computation module). This random signal can be used in connection with the creation or new concepts which will be discussed in a later section of the present disclosure.

The neurons of a neuronal network can be arranged in layers (which are not to be confused with the vertical layers (cf. FIG. 3) of a computation module if the computation module has a hierarchical architecture).

In some embodiments, the layers of the neuronal network will not be fully connected while in other embodiments the layers of at least some of the neuronal networks of the computation modules can be fully connected.

In some embodiments, computational groups can be provided, wherein the computational groups themselves could be organized into meta-groups. In some embodiments there could be keys for the data segments which signify that these data segments are specific for a computational group or meta-group. Such keys can be provided in addition to keys which are specific for individual computation modules and/ or which are specific for individual computational groups.

Mathematically, groups of computation modules and computational groups (if provided) can be represented by tensorial products $\otimes_k \_\otimes_l C_{k,l}$ of a number n×m of computation modules $C_{k,l}$, wherein, e.g., a first computational group is given by k=1, . . . , n–p and l=1, . . . , m–q and another computational group is given by k=n–p+1, . . . , n and l=m–q+1, . . . , m. If the computational groups are organized into meta-groups, these meta-groups can also be mathematically represented by tensorial products.

Configuration of a computation module can be done, e.g., by choosing the type of neuronal network to be used (e.g., classical or Quantum general ANNs or more specific ANNs like MfNN—Multi-layer Feed-Forward NNs for pictorial— e.g., 3d model—or video data, RNNs such as LSTMs for analysis of sound data, . . . ) and/or the specific setup of the neuronal networks to be used (e.g., which training data a neuronal network is trained with, the number of layers in the neuronal network, the number of neurons, . . . ).

In some embodiments a computation module can have a hierarchical structure (forming a vertical type of organization) meaning that a computation module can have function-specific layers (which can be thought of to be vertically-stacked). It is possible that all computation module and/or that computation modules of a given computational group or meta-group have the same hierarchical structure and/or that the hierarchical structure varies from computational group to computational group and/or meta-group to meta-group.

By way of example, a first layer (counting from the top of the stack, figuratively speaking) of the hierarchical structure can be used to receive data and to process this data to prepare it for the machine learning method specific to the computation module. Another layer which is connected to the first layer (possibly by way of one or several intermediate layers such that it receives data from the first layer and, possibly, the intermediate layer(s)) can include at least one neuronal network which processes data provided by the first layer (and possibly intermediate layer(s)) and outputs the result of the executed machine learning method to the at least one shared memory device and/or at least one other computation module and/or to at least one data hub process and/or routing process. At least one wore layer can be provided after the layer containing the at least one neuronal network which can use machine learning methods (e.g., in the form of a neuronal network) to determine where data processed by the at least one neuronal network of the previous layer should be sent to.

In some embodiments the first layer can be used to process data by applying a topological down-transforming process. After initial configuration a neuronal network requires input data of constant size, e.g., an input vector of size 10000. In the prior art, if the input vector is larger it is cut-off, if it is smaller padding can be used. In contrast, topological down-transformation provides input with the correct size for a given neuronal network.

In some embodiments a computation module can have at least six layers I-VI having, e.g., the following functions regarding data analysis and interaction (nb., if categorical constructs are used, the layers can be connected together via morphisms):

Layer I is configured to process data, in particular module-specific keyed data segments, obtained from shared memory or a data hub process such as a target vector. This layer can prepare data to be better suited for processing by the at least one neuronal network, e.g., by topological down transformation. It can send this data to layers II and III.

Layers II and III can comprise at least one neuronal network each, each of which processes data obtained from layer I and, possibly, from other computation modules. These are the layers where machine learning can take place to process data during data analysis in a cognitive way for example recognition of structure in a 3d model or picture) using well-known backpropagating neuronal networks (synaptic weights are modified during training to learn pictures, words, . . . ) such as general ANNs or more specific ANNs like MfNNs LSTMs, . . . . In some embodiments, these layers can also receive information from at least one other computation module, e.g., from layers V or VI of the at least one other computation module. In some embodiments, layer III contains at least one neuronal network which receives random signals as described below.

Layer IV can comprise at least one neuronal network which, however, is not used for cognitive data processing but to transform data from a data hub process or shared memory such as an input vector, e.g., by topological down transformation. It can send this data to layers II and III.

In layers V and VI neuronal networks (e.g., of the general type present in layers II and III) can be present which can be used to learn whether information represented by data is better suited to be processed in a different computation module and can be used to send this data accordingly to a data hub process (if present) and/or the shared memory and/or routing processes (if present) and/or directly to another computation module, where this data can be inputted, e.g., in layers II or III.

The vertical organization of computation modules can be present together with a horizontal organization (i.e., organization into computational groups or meta-groups) or also if there is no horizontal organization present.

A computation module can consist of one or several sub-modules, at least on one of the possibly several layers or on all layers, in the sense that parallel computation can take place in a computation module. By way of example, one computation module could comprise more than one sub-module, wherein each sub-module contains a different neuronal network. The different sub-modules can be active in parallel or only one or more of the sub-modules might be active at a given time, e.g., if a module specific data segment calls for it.

It is to be understood that, from the viewpoint of a programmer, a computation module is a certain structure of the programming language the computer program is programmed in. By way of example, if C++ is used as language, a computation module could be a C++ class (not as a data container but encoding a process) having pointers to other C++ classes representing other computation modules, data hub processes, . . . . Each C++ class representing a computation module can comprise other C++ classes representing the components of the computation module such as the neuronal network(s) of the computation module. After starting the computer program the processes encoding the computation modules, the data hub process(es) (if present) and possible other components will usually run idly until input data is provided via the at least one first interface.

With respect to execution of the computation modules by the at least one computing device of the system it, can be provided, with respect to an embodiment, that each computation module forms one thread. With respect to a single computation module each computational entity of that computation module, such as a neuronal network, this entity can be executed by a single CPU or core of a CPU or by several CPUs or cores of one or several CPUs, depending on the complexity of the entity.

The system is configured with a given number of computation modules (usually in the amount of at least several hundred but preferably in the amount of several thousand, several ten-thousand, several hundred-thousand or even several million computation modules).

It is pre-determined, with respect to the computation modules, which horizontal computational groups and/or meta-groups and/or vertical logical layers, if any, will be present.

It is also pre-determined how many and which neuronal networks are present in which computation modules and how each neuronal network is built.

Furthermore, in some embodiments, a number of categorical constructs (such as commutative diagrams, functors, natural transformations, projective limits, . . . ) can be built using the computation modules to model the objects and morphisms of the categorical constructs (as explained below).

In some embodiments a random signal generator can be configured to provide random signals to at least some of the artificial neurons of at least some of the computation modules to enhance unsupervised learning capacity of the system and method.

In preferred embodiments, the plurality of parallelly executed processes comprises at least one data hub process. The at least one data hub process could be embodied by a at least one group of computation modules and/or by a separate process running in parallel with the computation modules.

In some embodiments, the at least one data, hub process has an important role with respect to the flow of data in the system and method. In the prior art it is common that input data is processed in a linear way, i.e., input data is inputted to a process which may include several parallel and sequential sub-processes and the output of the process can be used as input for other processes or can be outputted via an interface. A plurality of such linear processes might run parallel. It is to be understood that the different sub-processes (structures) of the data hub process can run completely independently from each other such that could also be viewed as processes in their own right instead of sub-processes of a bigger structure, i.e., of the data hub process.

In a system and method according to preferred embodiments of the invention, input data in the form of a digital data record is reviewed by the at least one data hub process and—if the input data is not already present in forum of data segments (e.g., if the digital data record represents an anatomical structure having a plurality of anatomical sub-structure such as a representation of a dental arch having a plurality of visible parts of teeth and gingiva, as opposed to a digital data record representing an anatomical sub-structure in isolation such as a visible part of a single tooth)—uses at least one segmentation sub-process to segment the input data into data segments, which are provided with keys by at least one keying sub-process creating keyed data segments. The keyed data segments are stored in the at least one shared memory device (at any given time there might be none or a single segmentation sub-process or keying sub-process or a plurality of segmentation sub-processes or keying sub-processes, a different number of segmentation or keying sub-processes might be present at different times).

Segmentation of the input data to create segmented input data, in case the input data is not already present in segmented form, can be done in different ways, e.g., using supervised learning of one or more neuronal networks. By way of example, segmentation could provide separation of a totality of anatomical sub-structures represented in a digital data record into the individual anatomical sub-structures such as parts of individual teeth, individual teeth and/or gingiva.

Generation of keys can be more or less specific:

By way of example, non-specific generation of keys could be done such that, depending on the number of computation modules and/or computational groups of computation modules present, one specific key is computed by the at least one data hub process for each computation module or computational group or meta-group and data segments are randomly provided with one of the keys. It can be readily understood that this is not the most efficient way to work but it might be sufficient for some embodiments.

By way of a preferred example, generation of keys is done in a more specific way, employing machine learning techniques such as neuronal networks in some embodiments. In these embodiments, during training, at least one data hub process is presented with training data in the form of different input data and learns different keys depending on the input data. In some embodiments the input data might be in the form of visual data (e.g., 3d models) representing different kinds of teeth such as "incisor", "molar", "canine", . . . in isolation and the at least one data hub process might compute an "incisor"-key, a "molar"-key, a "canine"-key, . . . In these embodiments, a first computation module or computational group or meta-group of computation modules would have been trained (in a supervised and/or unsupervised. way) to recognize an object in a first form (e.g., in the form of an "incisor"), a different computation module or computational group or meta-group of computation modules would have been trained (in a supervised and/or unsupervised way) to recognize an object in a second form (e.g., in the form of a "molar"), . . . In some embodiments one or more ART networks (adaptive resonance theory network) could be used as machine learning technique in the at least one data hub process.

The computation modules can learn to recognize module-specific keys by loading and working on training data segments keyed with different keys and by remembering with respect to which keys the training data segments were fitting, e.g., in the sense that a computation module was able to recognize an anatomical sub-structure it was trained to represent. If, e.g., that computation module had been trained to recognize a visible part of tooth 41 (first incisor on the lower right in the ISO 3950 notation) and has been presented with training data segments for the individual teeth present in a human dentition, it will have remembered the key with which the training data segment representing tooth 41 had been keyed.

Once a keyed data segment has been loaded by one or more computation modules it can be deleted from the shared memory device to save memory space. It has to be noted that even if a keyed data segment is deleted the data hub process can retain the information which keyed data segments were segmented from the same input data.

It should be noted that a key does not have to be present as distinctive code. A key might also be present in the data segment itself or be represented by the structure of the data segment or could be represented by morphisms between the input data and the individual data segment. Therefore, the term "keyed" data segment is to be understood to mean a data segment which can be recognized by at least one computation module as module-specific.

In some embodiments tolerance parameters can be given to determine when a key is at least approximately matching for a specific computation module and/or computational group and/or meta-group. In some embodiments these tolerance parameters can be provided by a routing process.

The at least one data hub process can keep information regarding which shared keyed data segments were segmented from the same input data (this can be done in different ways, e.g., by way of the keys or by separate identifiers or by use of categorical constructs such as a projective limit) if segmentation happened within the system. The keys themselves, if present as distinctive code, can be small (e.g., amounting to only a few bits., e.g., 30-40 bits). This can be used to reconstruct how anatomical sub-structures were arranged relative to each other in the digital data record.

In some embodiments at least one routing process is present (which can form part of the data hub process as a sub-process or can be provided separately from the data hub process, e.g., by at least one group of computation modules), which directs output provided by at least one of the computation modules (and/or computational groups and/or meta-groups) to at least one other computation module (and/or computational groups and/or meta-groups). In other words, the process output of a computation module (and/or computational groups and/or meta-groups) can be directed to that other computation module (and/or computational groups and/or meta-groups) which can best deal with this output. In terms of computer language, references between computation modules can, e.g., be modeled by way of pointers.

In some embodiments the routing process can be used to provide tolerance parameters to neuronal networks of computation modules.

In some embodiments the routing process can be used to repeatedly check the weights of synapses of neuronal networks of the computation modules to make sure that they do not diverge (e.g., whether they reside in an interval, e.g., [−1, 1], with a certain desired distribution or whether they diverge from that distribution). In case it finds divergence in one or more neuronal networks of a computation module (which could make this computation module problematic) it can transfer the processes being run by this computation module to a different computation module and can reset the weights of the computation iodine which showed divergence. For this it is useful if the routing process is provided with a real time clock. In some embodiments the checking of the weights of synapses could be performed by another component of the system or a dedicated weight analyzing device, preferably having access to a real time clock.

In preferred embodiments, the computation modules do not receive all of the input data indiscriminately but are configured such that they know to process only data keyed with a key which is specific to a given computation module (module-specific data segments). The computation modules check repeatedly (can be done in a synchronous or asynchronous way) whether there is any module-specific data segment stored in the shared memory device. If a data segment with a fitting key, i.e., a module-specific data segment, is detected, the computation module loads the module-specific keyed data segment and starts the data analysis process for which it is configured. In this way, although there is a plurality of threads or sub-processes running to check for module-specific data, computationally intensive tasks such as the computation processes of the neuronal networks are only started when module-specific data segments have been detected, otherwise a computation module can stay idle, smile embodiments, it is sufficient for a key to be only approximately fitting (e.g., to a pre-determined range) for the keyed data segment to be viewed as a module-specific data segment. Clearly, the broader a pre-determined range is chosen, the more data segment will be viewed as module-specific. An appropriate pre-determined range for a key can be found by trial-and-error.

By way of example it is possible that a computation module has identified that a data segment represents a molar, and knows that such data has to be mapped to a specific group of other computation modules. By way of another example, a computation module might have identified that a data segment represents an incisor and knows that such data is to be mapped to a specific group of other computation modules.

In some embodiments, sending data from one computation module to another computation module can be done directly via at least one of: connections between computation modules (these can be a simple signaling connection or can themselves comprise one or more computation modules), one of the data hub processes, a routing process, the shared memory. In an information-point-of-view the connection between different categories can be thought of by using the concept of a fibered category, i.e., a category connected to a base or index category. Two categories can be connected by connecting their base or index categories.

Operation of different embodiments of system and method:

It is a major concept of the present invention that different (groups of) computation modules represent different anatomical sub-structures (at least individual visible parts of teeth and gingiva) that might be present in a dentition of a patient, each anatomical sub-structure being represented in different configurational states, shapes and sizes (possibly also different colors). The phrase "a computation module represents an anatomical sub-structure" means that there is a computation module present in the system which recognizes this anatomical sub-structure. This representation is created during training in which the different groups of computation modules are presented with digital data representing the different anatomical sub-structures and learn, at least partially in one of the usual ways known in machine learning, to recognize the different anatomical sub-structures.

By way of example, the system and method are able to automatically rotate an anatomical sub-structure which is helpful if, e.g., identification of an anatomical sub-structure (such as separation of gingiva and teeth or separation of individual teeth from each other) has been trained with a certain angle of view, e.g., 0 degrees, and the 3d model provided as input has a different angle of view, e.g., 45 degrees.

In inference operation the different groups of computation modules apply the machine learning technique on that digital data record and, as a result, those anatomical sub-structure which are present in the digital data record are identified by the groups of computation modules representing these anatomical sub structures. These groups of computation modules output the result to at least one different group of computation modules and/or to the shared memory device and/or to the at least one second interface. As output of the system and method at least a virtual model is created based on the identified anatomical sub-structures and the virtual model is made available to the second interface, said virtual model representing at least the visible parts of teeth, the visible parts of teeth being separated from each other and the gingiva.

In other words, the system and method of the present disclosure, in inference operation are able to automatically understand (cognitively process data) the (at least part of a) person's dentition which is represented by a digital data record representing a 3d model of that part of dentition and, in some embodiments (see below), supplemental information regarding the (part of the) dentition concerning, e.g., the presence and position of dental implants and/or dental fillings, shape of non-visible parts (e.g., roots of teeth), . . . , By way of example, the 3d model of the at least part of the dentition can be given in the form of at least one CAD-file such as at least one scan file (e.g., STL file and/or at least one object file).

To automatically understand a persons dentition means that the system and method are able to identify the anatomical sub-structures present in a given dentition, such as gingiva, the visible parts of individual teeth, the border between gingiva and the visible parts of individual teeth, the borders between the visible parts of individual teeth and what type of teeth the individual teeth belong to. The system and method are also able to analyze the spatial information present in the 3d model, (e.g., the position and orientation of an anatomical sub-structure in a coordinate system of the 3d model).

Automatic separation of gingiva and visible parts of teeth can be done by the neuronal networks of the computation modules according to established methods, edge detection, after training in which a supervisor indicates to the system and method which parts of 3d models of training dentitions form part of gingiva and which parts are visible parts of teeth. In the same way automatic separation of teeth from each other can be trained. The trained system and method have a plurality of computation modules representing the gingiva and teeth in combination and gingiva and individual teeth separated from each other. As an output the system and method can provide a 3d curve representing the border line between teeth and gingiva.

In inference operation the system and method do not need constant access to a database as their operation is based on internal knowledge which is coded in the groups of computation modules and their connections.

If at least one data hub process is configured, in inference operation at least one, possibly each group of computation modules is preferably configured to:

check whether data segments provided with a specific key are present in the at least one shared memory device and/or are provided by at least one different group of computation modules, and to:

run idly if no data segment with the specific key is detected or provided if a data segment with the specific key is detected in the at least one shared memory device or provided by at least one different group of computation modules, apply the machine learning technique on that data segment and output the result to at least one different group of computation modules and/or to the shared memory device and/or to the at least one second interface In this way, hardware requirements can be reduced because only those groups of computation modules will be active at any given moment during inference operation which have loaded data, segments while those groups of computation modules which have not detected data, segments with specific keys stay idle (except, of course, for the checking for specific keys).

In some embodiments, at least one group of computation modules and/or the at least one data hub process can represent information about how the identified anatomical sub-structures are arranged relative to each other in the at least part of the dentition. If present, the information how the identified anatomical sub-structures are arranged relative to each other in the at least part of the dentition can also be used to create the virtual model. If this information is not present, computation modules can check where each identified anatomical sub-structure is present in the digital data record representing the 3d model showing all of the anatomical sub-structures.

In some embodiments said at least one digital data record can be provided as a scan file. It is preferably provided in the form of at least one of the following group:

CAD file, preferably STL file, and/or object file

CBCT file (e.g., DICOM file format)

picture file (such JPG, PING, GIF, . . . )

ASCII file (such as CSV, TXT, . . . )

object, file (such as OBJ, . . . )

In some embodiments at least one group of computation modules is configured to analyze the spatial information regarding the anatomical sub-structures contained in at least one digital data record which is provided in the form of at least one CAD file. By way of example, an STL, file is a type of CAD file in which surfaces are represented by a collection of triangles, each triangle being represented a unit normal and its three vertices. An STL file contains the number of triangles present in the file and, for each triangle, the normal vector and the three vertices in a given coordinate system. Once the system is configured to read an STL file it can make use of the spatial information given therein. The STL file can be provided in binary form or as an ASCII file e.g., a CSV file). An alternative file format is an object file (OBJ) which uses polygons.

This makes it easier for the system and method to understand which anatomical sub-structures are given in the at least one CAD file because the spatial information can be used to understand the orientations and relative positions of the anatomical sub-structures in the at least one CAD file. Based on this understanding the search for computation modules representing anatomical sub-structures which match with those shown in the at least one CAD file will achieve results faster because only those computation modules representing anatomical sub-structures the same or closely related orientations and/or relative positions need to be taken into account.

By way of example the at least one scan file, preferably STL file, can comprise at least one of the following scans (partial or complete): maxillary scan, mandibular scan, bite scan.

In some embodiments a supplemental data record representing supplemental information about at least part of a dentition of a patient which is not, or not completely, represented in the digital data record or is represented in a different way is provided to the system and method. In this case it can be provided that:

at least one group of computation modules analyzes the supplemental information represented in the supplemental data record at least one group of computation modules transforms the anatomical sub-structures identified in the digital data record until they fit to their representation in the supplemental data record, or vice-versa if supplemental information is present for at least one of the identified anatomical sub-structures in the virtual model, said supplemental information can be connected to (colloquially speaking, is pinned to) said at least one identified anatomical sub-structure in the virtual model By way of example, said supplemental information can comprise images of the patient's oral area by way of a photo, a CT-scan or an X-ray-image, or vice-versa. In addition or alternatively, said supplemental information can comprise a written description of at least part of the patient's dentition.

By way of example, if the supplemental information is a digital representation of an X-ray image of the at least part of dentition to which the 3d model represented in the digital data record refers to, a tooth which has been separated from the 3d model can be transformed (rotated, shifted and/or scaled) by the system and method until it can be found by the system and method in the X-ray image. In this way, tooth by tooth, the system and method can gather supplemental information from the X-ray image, e.g, shape of roots of the teeth, presence of a dental filling or a dental implant, presence of caries, brittleness, . . . .

If supplemental information is given, this supplemental information can be used to improve the understanding of the system and method by providing restrictions (boundary conditions) to possible transformations, e.g., the system and method have been trained to know that a dental implant must not be moved or a tooth provided with a dental filling must not be ground. The supplemental information can be given, e.g., in the form of a medical image (e.g., a photo, a tomographic scan, an X-ray picture, . . . ) and/or in the form of a description given in natural language by an operator such as a doctor. In addition or alternatively, the supplemental model can be used to create a virtual model of a complete tooth, i.e., showing the visible parts (above the gingiva) and the invisible parts (concealed by the gingiva), provided that the information regarding the invisible parts can be extracted from the supplemental information.

With respect to the system and method it is provided that:
different groups of computation modules represent at least parts of different dentitions which are cataloged as belonging to a catalog of target dentitions
different groups of computation modules represent at least parts of different dentitions which are cataloged as belonging to a catalog of starting dentitions
different groups of computation modules represent at least parts of different dentitions which are cataloged as belonging to a catalog of intermediary dentitions
for each starting dentition and for each target dentition, there are connections, preferably represented by different groups of computation modules, between a starting dentition, different intermediary dentitions and a target dentition, thereby establishing at least one sequence of intermediary dentitions leading from a starting dentition to a target dentition Once the system or method has identified that an inputted digital data record representing a (part of a) dentition (or the virtual model created based on the inputted digital data record) shows misalignment it can find, due to its training, at least one pre-trained (part of a) starting dentition identical to or at least similar to the dentition represented by the inputted digital data record and it will also know a plurality of (part of) intermediary dentitions with a lesser degree of misalignment and, therefore, it also knows a possible path from the starting dentition (which is identical to or at least similar to the dentition represented by the inputted digital data record) and, therefore, from the dentition represented by the inputted digital data record to a possible target dentition (with shows an acceptable degree of misalignment or no misalignment at all) via the intermediary dentitions which have a lesser degree of misalignment than the starting dentition. In other words, provided with a digital data record comprising a dentition showing misalignment (and/or the virtual model for that dentition), the system or method looks for (groups of) computation modules which represent at least one identical or at least similar starting dentition and can then follow an established sequence of intermediary dentitions (themselves being represented by, possibly groups of, computation modules) to arrive at a target dentition (being represented by, possibly groups of, computation modules) thereby establishing a treatment plan for the dentition represented by the inputted digital data record. This can be done with respect to different target dentitions and/or different sequences of intermediary dentitions to create more than one treatment plan for the same starting dentition.

Creation of the catalog of target dentitions, starting dentitions and intermediary dentitions and establishing the sequences of intermediary dentitions can be done during training of the system and method.

Alternatively, the system or method could directly apply any of the techniques known in the art of orthodontics to determine a sequence of transformations to reach the desired target dentition from the virtual model which was created based on the digital data record. In this case, the system and method inputs both, the virtual model and the desired target dentition, into an algorithm known in the prior art to calculate the necessary transformations.

It can be provided that:
a set of possible boundary conditions is provided
based on the virtual model, in particular in case supplemental information is present in the virtual model, the system is configured to check whether at least one of the boundary conditions is applicable
if at least one of the boundary conditions is applicable, taking account of said at least one boundary condition when determining the set of transformations A boundary condition can result from supplemental information (see above) and/or can be provided to the system, e.g., by way of written description. By way of example, a boundary condition can be:
the command not to move a specific tooth in a specific patient's dentition at all (e.g., because it was replaced by an implant) and/or
the definition of a possible range of movement for a specific tooth in a specific patient's dentition and/or
the command not to grind a specific tooth in a specific patient's dentition (e.g., because it has a massive dental filling)

In embodiments in which a set of transformations is determined it can be provided that said set of transformations is used to create at least one treatment plan, preferably a plurality of treatment plans (which are preferably created in parallel), and the at least one treatment plan is provided to the at least one second interface and wherein, preferably, the at least one treatment plan is provided in form of:
at least one CAD file, preferably an STL file and/or object file, and/or
at least one human-readable file (e.g., an ASCII file, such as a CSV file, or a graphic file)

In this case it can be provided that the at least one treatment plan comprises successive and/or iterative steps for the treatment of the orthodontic condition to a final orthodontic condition (being identical to or at least close to a target dentition), preferably via at least one appliance, particularly preferably in the form of a fixed and/or removable appliance. If the at least one appliance is represented by at least one CAD file, preferably an file and/or an object file, this at least one CAD file may be used directly for production of the at least one appliance by any known process such as producing molds for casting or using additive manufacturing such as 3d printing or can serve as a basis for such production.

Different treatment plans for the same orthodontic condition (same starting dentition) can differ from each other due to different transformations (different sequence of intermediary dentitions) and/or due to different target dentitions.

The internal knowledge of the system and method can comprise information about how the orthodontic condition of a given dentition is to be rated relative to the set of possible target dentitions which enables the system and method to compare the dentition in the given state to an improved state and to compute the necessary transformations of the dentition in the given state to arrive at or at least approximate the improved state. The system and method can then provide a virtual model of the improved state of the dentition and an electronic file (e.g., a CSV-file or another file type comprising alphanumeric information) comprising information, e.g., how each individual tooth is to be manipulated, that and/or why some teeth must not be manipulated in a certain way, how one or, more likely, a plurality of appliances is to be designed to arrive at the improved state. The information can be given in computer-readable and/or human-readable format.

Computation of the necessary transformations of a dentition in a given state to arrive at or at least approximate a dentition in a different state represented by a target dentition is done by a plurality of computation modules, e.g., such that each tooth is shifted and/or rotated from its position and orientation in the given state to conform to a position and orientation in the different state by an individual computation module or group of computation modules.

Preferably, for one and the same orthodontic condition several different treatment plans are generated (preferably in parallel) by the system and method, respectively, which differ, e.g., in the number of successive and/or iterative steps, the steps themselves, the type of appliance used for the treatment, and so on. By way of example, at least two, preferably at least three, different treatment plans could be generated relating to one and the same orthodontic condition.

In some embodiments at least one group of computation modules is configured to determine, for an appliance in the form of at least one orthodontic bracket, the shape of a bonding surface of the at least one orthodontic bracket such that it is a fit to the part of the surface of a tooth to which it is to be bonded (e.g., by creating a negative of the surface of the tooth to be at least one orthodontic bracket is to be bonded to). In this way orthodontic brackets which are a perfect fit for a given patient can be produced.

After the system or method has been trained, interaction with an operator during inference operation can, e.g., happen as follows:

In some embodiments, the virtual model and/or the at least one treatment plan created by the system can be sent to an external computer program (e.g., any frontend system available on the market) for interaction with the operator. A human operator can check the files provided by the system and can make changes if that is deemed necessary. The checked and/or modified files are not sent back to the system but can be further acted upon in the external computer program by a human operator for controlling and documentation purposes and further processing.

In some embodiments a human operator can directly interact with the system to check and, if necessary, modify the virtual model and/or the at least one treatment plan created by the system. The system is capable to process the modifications, if any, and to create a modified virtual model and/or a modified at least one treatment plan. These output files can be sent to an external computer program (e.g., any frontend system available on the market) for further user interaction for controlling and documentation purposes and further processing.

In some embodiments the system or method directly generates files which can be used for production of appliances.

In some embodiments it can be provided that at least
said at least one shared memory device
said at least one computing device are located on at least one server and at least
said at least one first interface
said at least one second interface are located in the form of
 at least one client program of the server on a client computer which is connected to said at least one server by a communication network, preferably the internet.

This makes it possible that all required information to propose a treatment plan for the orthodontic condition can be gathered locally on the at least one client computer. The at least one server can use that information to generate at least one treatment plan essentially instantaneously, wherein an operator is able to select the preferred treatment of his orthodontic condition with the help of the at least one treatment plan immediately via the at least one local client computer, e.g., at a dentists office.

As already mentioned the technical term "real time" is defined pursuant to the norm DIN ISO/IEC 2382 as the operation of a computing system in which programs for processing data are always ready for operation, in such a way that the processing results are available within a predetermined period of time. If a client-server architecture is used, the term "real time" is understood to mean that processing of digital information and/or transmitting digital information between at least one client program and the least one server does not include a lag that is induced by a preparation of the digital information within the at least one client by the patient and/or technical staff for instance. The virtual model and/or the at least one treatment plan is available for the patient in real time, i.e., at most after a de-fined period of time after the at least one digital data record can be transmitted to the at least one server and is affected essentially by the computation time and the data transfer time. Time delays which occur during steps in the processing can be neglected in comparison to typical user-dependent time delays.

In such embodiments it can be provided that said at least one client program is designed as being or comprising a plugin in the form of an interface between at least one computer program running on said client computer, preferably a computer program certified for orthodontic use, and the at least one server, wherein the at least one client program is configured to:
translate and/or edit, preferably essentially in real time, user inputs and/or data of the at least one computer program relating to the at least part of a dentition of patient to create the at least one digital data record and/or
translate and/or edit, preferably essentially in real time, the output of the at least one second interface for the at least one computer program By this it is possible that the plugin acts as a compiler between the at least one computing device at the server and the at least one client program that can operate locally. Therefore, a translation of user inputs and/or data that are particularly in a form consistent with the certified computer program need not be translated by the at least one computing device itself as the plugin translates and/or edits the information into a form that can be processed by the at least one computing device. Thus, the at least one computing device can operate faster to create the at least virtual model and/or the at least one treatment plan. A separate interpreter is not necessary. Data preparation for the user of the at least one client program and/or the at least one computing device is done by the plugin wherein the at least one client program is not fixed to certain it that have to be consistent with a data structure of the at least one computing device. Moreover, if the system prepares at least one treatment plan, this at least one treatment plan can be edited to prepare it visually in a user-friendly way. In general, an operator (e.g., a patient and/or technical staff) has the possibility to configure the at least one treatment plan, the orthodontic condition and/or data regarding the orthodontic condition within the at least one client program, the at least one client computer and/or the at least one sever. If according to the operator there exists, e.g., a more convenient way for a proposed movement of a tooth of the at least one treatment plan, the operator is able to adapt the at least one treatment plan accordingly.

In some embodiments it can be provided that description in written natural language is attached to individual anatomical sub-structures of a dentition, e.g., to an individual tooth. This description can e.g., comprise information about the transformations necessary for the individual anatomical sub-structure in orthodontic treatment and/or supplemental information such as the presence of a dental implant, a dental filling or caries. The anatomical sub-structure can comprise one tooth or several teeth, possibly part of or a complete dental arch. Attachment of the description to the individual anatomical sub-structure can be done by way of computation modules representing fibered categories in which the individual sub-structure is represented by a fiber and the description is represented by a base of a fibered category, if categorical constructs are used.

In some embodiments the system or method creates a virtual model of an appliance in the form of an orthodontic bracket. An orthodontic bracket is placed onto a tooth and is connected to orthodontic brackets on other teeth by way of an archwire to move the teeth to a desired dentition (intermediary dentition or target dentition). By using the information of the virtual model of a dentition (starting dentition or intermediary dentition), the system can create a bonding surface of the orthodontic bracket which perfectly matches the surface of the tooth to which it is bonded.

In some embodiments the system or method creates a virtual model of an appliance in the form of a fixed lingual retainer. Such a fixed lingual retainer is intended for use after a target dentition has been reached in a treatment plan and is meant to keep the teeth in the positions defined by the target dentition. The virtual model of the fixed lingual retainer comprises placement portions to be placed the top edge of selected teeth and tooth-adhering portions having a generally flat top edge and a generally curved bottom edge and which are designed by the system to exactly match the shape of the lingual side of the teeth they are placed on (e.g., by creating a negative shape of a tooth's surface. Connection portions are located at a position below the top edge of the tooth-adhering portions and are formed narrower than the tooth-adhering portions to expose as much tooth surface as possible between the tooth-adhering portions.

Use of categorical constructs the system and method:

In a preferred embodiment groups of computation modules are used to represent constructs (mathematical structures) which can be modeled mathematically using category theory (categorical construct), in the language of category theory one or more computation module can represent one or more categories, object(s) of categories or morphism(s) of categories. One or more computation module can represent a functor (a map between categories) or a natural transformation (a map between functors) or universal objects (such as projective limit, pullback, pushout, . . . ). The use of categorical constructs in connection with a plurality of co-running computation modules improves the processing of data without having the hardware requirements that would be present if a database were to be used. Furthermore, using categorical constructs allows more easily to represent logical connections. Flow of information can be handled in an efficient way using connections which can be modeled by categorical constructs. Other than a database, in some embodiments, the system can create and learn new concepts.

Composition of morphisms can be used to represent processes and/or concepts sequentially.

Tensor products can be used to represent processes and/or concepts parallelly.

Functors can be used to map structures and/or concepts from one category to another category.

Natural transformations can be used to map one functor to another functor.

Commutative diagrams can be used to learn an unknown concept (with or without supervision) which forms part of a commutative diagram if enough of the other elements of the commutative diagram are known.

A combination and/or composition of morphisms, tensor products, functors, natural transformations and/or commutative diagrams and/or of the other categorical constructs described in this disclosure can be used to learn new concepts (with or without supervision) by using a network of diagrams.

By way of example the system and method can be configured such that there is a plurality of categories present, wherein each category is represented by a group of interconnected computation modules or a single computation module. The interconnection can be done by composition of morphisms or functors (directly or, in case of fibered categories, via their base categories) which, in programming language, means that the language constructs representing the computation modules in a chosen programming language are suitably interconnected by the means provided by the chosen language, e.g., using pointers between classes.

Structures of a data hub process such as, e.g., a routing process, can be modeled, e.g., as a morphism or functor between categories which, in turn, are modeled by computation modules or groups of computation modules and/or by other structures of a data hub process.

By way of example, data analysis using categorical constructs can be done in the following way (the following example uses data segments, works in the same way for non-segmented data):

Suppose input data $ID_1$ and $ID_2$ is present in segmented form $[KS_l^1, \ldots, KS_k^1]$ and $[KS_l^2, \ldots, KS_l^2]$ such that data segment $KS_i^1/KS_i^2$ is specific to a first/second group of computation modules $C_{n,m}^2/C_{o,p}^2$ (the data segments can be created by at least one data hub process or can already present in segmented form in the input data) in the shared memory. Computation modules $C_{n,m}^1$ of the first group, upon checking the content of the shared memory, see and extract keyed data segments $KS_i^1$; computation modules $C_{o,p}^2$ of a second group, upon checking the content of the shared memory, see and extract keyed data segments $KS_i^2$ and computation modules $C_{o,p}^2$ of a third group, upon checking the content of the shared memory, see that there is no module-specific data present. For simplicity it is assumed in this example that a keyed data segment is specific to a single group of computation modules only, in some embodiments it might be specific to a plurality of groups of computation modules which, together, might represent a categorical construct such as an object or a morphism. Additionally or alternatively, more specific keys can be used which are not only specific for a group of computation modules but for single computation modules.

Once a module-specific data segment $KS_i^1$ has been loaded by a computation module $C_{l,m}^{1,2}$ this computation module $C_{l,m}^{1,2}$ can, e.g., check whether this data segment corresponds to an object $A_k$ of the category $\mathcal{A}$ represented by this computation module $C_{l,m}^{1,2}$.

A computation module $C_{l,m}^k$ (or sometimes a plurality of computation modules) is said to represent an object $A_i$ of a category $\mathcal{A}$ in the sense that if provided with different versions of data or data segments $KS_l, \ldots KS_n$ which, e.g., all represent a molar when seen under different angles and/or with a deviation from the a common tooth-shape of a molar, e.g., because massive caries is present, then the computation module can be trained to recognize that all of these data segments refer to an "ideal object" $A_i$ (in the given example "molar"). In the same sense, another computation module is said to represent an object $B_i$ of a category $\mathcal{B}$. Representation of an object could also be done by groups of computation modules: E.g., a first group of computation modules can represent object $A_i$ by having each computation module of that first group representing different versions of this object $A_i$. A second group of computation modules can represent object $B_i$ by having each computation module of that first group representing different versions of this object $B_i$.

Once a computation module $C_{l,m}^{k}$ has identified that a data segment $KS_i$ corresponds to an object $A_i$ of the category $\mathcal{A}$ represented by this computation module $C_{l,m}^{k}$, it depends on the configuration (either initial configuration or configuration after training) what its action upon identification of the ob $A_i$ is. By way of example, it could simply send a message to another computation module $C_{u,v}^{i}$ such that the other computation module $C_{u,v}^{i}$ can take an appropriate action and/or it could send a message to a data hub process which, in turn, could reroute this message to yet another computation module $C_{o,p}^{j}$.

If there are at least two computation modules present which, say, represent two different objects $A_1, A_2$ of a given category $\mathcal{A}$, a third computation module can be used to represent a morphism $a_1$ in that category $\mathcal{A}$ between the two objects $A_1, A_2$ such that $$A_1 \xrightarrow{a_1} A_2.$$

Another computation module can represent another object $A_3$ of that category and another computation module can represent a morphism $$A_1 \xrightarrow{a_3} A_3.$$

Another computation module can represent a further morphism $$A_2 \xrightarrow{a_2} A_3$$

thus completing a commutative diagram in which $a_2 \circ a_1 = a_3$. Whenever the system has learned all but one part (object or morphism) of the commutative diagram it can use commutativity to find the missing part, e.g., if morphism $a_3$ is unknown or object $A_2$ is unknown, and can train a computation module to represent the missing part. In a sense, a commutative diagram can be understood to be an equation which allows computation of a missing variable of the equation (of course, more complex commutative diagrams can be built using this elementary commutative diagram).

By way of example, if $A_1$ represents the object "molar", $A_2$ represents "cavity", $A_3$ represents "a dental filling", $a_1$ represents "has" and $a_2$ represents "is filled by", then the system can learn the concept that "molar" has "a dental filling" because $a_2 \circ a_1 = a_3$ gives: "A cavity is filled by a dental filling" $\circ$ "Molar has a cavity"="Molar has a dental filling.", i.e., $a_3$="has".

If there are two categories $\mathcal{A}, \mathcal{B}$ represented, with objects $A_1, A_2$ and morphism f $$(A_1 \xrightarrow{f} A_2)$$

in category $\mathcal{A}$ and objects $B_1, B_2$ and morphism g $$(B_1 \xrightarrow{g} B_2)$$

in category $\mathcal{B}$, it is possible to have at least three computation modules represent a functor $\mathfrak{F}$ mapping objects and morphisms from category $\mathcal{A}$ to objects and morphisms in category $\mathcal{B}$ such that $\mathfrak{F}: A_1 \rightarrow B_1, A_2 \rightarrow B_2, f \rightarrow g$. This way, by using a total of at least nine computation modules, a simple commutative diagram can be built wherein one computation module is used per object $A_1, A_2, B_1, B_2$ and per morphism f, g and three computation modules are used for the functor $\mathfrak{F}$ with the functor condition that, of course, $g \circ \mathfrak{F}(A_1) = \mathfrak{F} \circ f(A_1)$.

When the categorical constructs are built during initial configuration of the system and method there is a plurality of categorical constructs which can be used by the system and method in the unsupervised learning step to learn new concepts, e.g., in the following way:

Suppose that with respect to the exemplary commutative diagram given above, category $\mathcal{A}$ represents the category of "molars" and category $\mathcal{B}$ represents the category of "incisors" such that $A_1, A_2$ are two molars which are connected to each other by a rotation represented by morphism f, in other words, the system has learned that a molar which has been rotated is still the same molar. Using functor $\mathfrak{F}$ this concept can be mapped to the category of "incisors" meaning it is not necessary for the system to re-learn the concept of "rotation of an anatomical sub-structure" in the category of "incisors".

Suppose that with respect to the exemplary functor given above, the first category is a "molar-category" in the sense that the objects of $\mathcal{A}$ represent "visible parts of molars" (e.g., $A_1$ represents the visible part of a specific molar shown in an image), $A_2$ represents "root of molar" and f represents the mapping "visible part of molar is connected to" and the second category is a "tooth-category" in the sense that the objects of $\mathcal{B}$, e.g., $B_1$, represent different kinds of "visible parts of teeth" and $B_2$ represents "root of tooth" and the functor $\mathfrak{F}$ maps from the "molar"-category to the "visible parts of teeth"-category. Let us further assume that morphism g is not yet known to the system. Because in a commutative diagram the composition $g \circ \mathfrak{F}(A_1)$ must give the same result as the composition $\mathfrak{F} \circ f(A_1)$, namely $B_2$, the system can learn that morphism g represents "visible part of tooth is connected to" and can configure a computation module to represent that morphism.

Alternatively, if only $B_1$ had been unknown but both morphisms f, g had been known, the system would have concluded that $B_1$ must represent "visible parts of teeth" and could configure a computation module to represent that object.

In category the technique to find unknown quantities that form part of a—possibly very complex—commutative diagram is sometimes colloquially called "diagram chasing".

The above examples, although of interest to the invention, are of course very simple. More complex categorical constructs can be used, such as, e.g., a pullback or pushout, a natural transformation or a projective limit (sometimes the projective limit is also called inverse limit or indirect limit in the literature).

One and the some categorical construct can be used for different functions during operation of the system and method (wherein each function will be represented by different groups of computation modules), e.g., the projective limit could be used to distribute data to different structures in the system (routing) or create new concepts using random signals.

With respect to a routing process, e.g., of a data hub process and/or by individual computation modules and/or groups of computation modules, to analyze data, by sending it to different computation modules the projective limit can be used, e.g., as follows:

Data which is to be interpreted is inputted to a computation module (depending on the complexity of the data it will, in practice, often have to be a group of several computation modules) which is interpreted to represent the projective limit of the data which is interpreted to consist of a sequence of data segments $$A_1 \xleftarrow{a_1} A_2 \xleftarrow{a_2} \cdots \xleftarrow{a_{n=k-1}} A_{n=k}.$$

The projective limit is the object $$\xleftarrow{\lim} A_i$$

together with morphisms $\pi_i$ which means that the sequence $A_{n=1}, \ldots, A_{n=k}$ is projected onto its ith member $A_{n=i}$. It can be remembered how the data X was segmented, e.g., by use of the projection morphisms $\pi_i$ and morphisms $a_i$.

By way of example, assume the system must interpret the meaning of some data X. Depending on the complexity of data X, a single computation module might not have sufficient complexity to calculate the meaning of data X. Therefore, data X is being sent to different computation modules (or groups of computation modules) and each computation module tries to find out whether the meaning of data X is known. If a computation module finds that it knows (at least part of) data X it can provide this information, either to the computation module which initially sent data X or, preferably, to a structure which can gather the responses of the different computation modules such as a routing process. If the computation module finds that it does not know data X it can send data X to a different group of computation modules (or a single computation module) to let them check the data X. This process can be facilitated by interpreting data X as the projective limit $$\xleftarrow{\lim} A_i$$

wherein the projection morphisms $\pi_i$ can be used to distribute the data X to different computation modules in the form of segments $A_{n=i}$ and the logical connection between the different data segments is preserved by the morphisms $a_i$. If data is to be sent to computation modules of a different category, say from category $\mathcal{A}$ to category C, computation modules representing a functor $\mathcal{F}$ between these categories can be used.

How a computation module can find out whether it knows some data or a data segment, by using categorical constructs, can be understood by remembering that a computation module represents an object $A_i$ in a category $\mathcal{A}$ and therefore the neuronal network(s) contained by the computation module can compare whether data X is at least isomorphic (i.e., similar, in other words, approximately equal) to the object $A_i$ represented by that computation module.

If computation modules having a vertical hierarchical structure are used, the projection of data segments to other objects could be done, e.g., in layers V and VI, by modeling projection morphisms.

In preferred embodiments the system and method are enabled to create new concepts itself, such as, e.g., new anatomical sub-structure (which, e.g., is an arrangement of two adjacent teeth) or a sentence such as "Molar A has a dental filling." and to configure computation modules to represent these new concepts. Such a new concept does not necessarily need to make sense. However, by checking the new concept with concepts that are already known by the system to make sense, such as, e.g., anatomical sub-structures in different shapes or different sentences concerning teeth, the system will often be able to decide for itself whether a new concept makes sense. It might, however, be necessary for the system in some cases to obtain external input to decide whether a new concept makes sense, e.g., by asking an operator of the system or accessing an external database. In other words, "creation of new concepts itself" means that these new concepts are logically derived from input data or from analysis of input data.

In some embodiments creating new concepts can be done or improved by inputting a random signal generated by a random signal generator to a receptor of a neuron. This random signal can be inputted to the result of the integration function to modify (e.g., by adding or multiplying) that result such that the activation function operates on the modified result. In this way, a neuronal network which is inputted with information will base its computation not on the inputted information alone but on the modified result. By this mechanism the information or concept which is represented by the neuronal network will be changed in creative ways. In many cases the changed information will be wrong or useless. In some cases, however, the new information or concept will be considered to be useful, e.g., to create new categorical constructs represented by newly configured computation modules. The random signal generator does not need to form part of the system, although this is certainly possible, but can be an external device which can be connected to the system. In some embodiments, the random signal generator will generate random signals in the form of random numbers taken from a pre-determined interval, e.g., the interval [0, 1]. Preferably, the random signals are sent not at regular time intervals but according to a Poisson distribution.

In case a new concept is found to be useful, the system can train one or more computation modules to represent this new concept. The new concept can be stored by the routing process until one or more computation modules have been trained.

In some embodiments only some of the neurons of a neuronal network will be provided with random signals, preferably those neurons which are more upstream with respect to the direction of information flow in the neuronal network. By way of example, in a layered neuronal network, the first or first and second layers after the input interface of the neuronal network might be provided with random signals while the neurons of the remaining layers will work in the way known in the art, i.e., without the input of random signals.

The concept of inputting a random signal into a neuron body should not be confused with the concept of inputting (e.g., adding or multiplying) random signals to the weights of the synapses of a neuron. This concept can also be applied with respect to the invention, irrespective of the question whether random signals are inputted to the neuron body or not.

In some embodiments the creation of new concepts by using random signals is done by at least one plurality of computation modules which represent a projective limit.

In those embodiments which make use of random signals to create new concepts, in most embodiments, at least two different pluralities of computation modules are present: at least one plurality which is used to analyze data and at least one plurality to create new concepts. The size of the former plurality will usually be larger than the size of the latter plurality. While the at least one plurality used for analyzing data will run idly most of the time and will only do computational work if module-specific data is present, the at least one plurality used to create new concepts will do more or less continuous work. In some embodiments, it might therefore be advantageous to transfer newly learned concepts to other computation modules to store them in order to free those computation modules used to create new concepts.

As a general matter, it should be noted that one and the same categorical object can be represented by different computation modules during operation of the system.

Training of system and method:

Training of the system (training of the method can be thought of analogously) after configuration is done in part in a supervised way and, at least in some embodiments (e.g., those with categorical constructs), in part in an unsupervised way and, in some embodiments using creation of new concepts. Training can be done in some embodiments partly before inference operation of the system and partly during inference operation as explained in the following:

The supervised training step can, in a first aspect, be done with respect to at least some of the neuronal networks, in the usual way by providing training data, comparing the created output with a target output and adapting the neuronal networks to better approximate the target output by the created output, e.g., with back-propagation, until a desired degree of accuracy is reached. This is usually done before inference operation of the system. Training the at least one data hub process (if present) with respect to segmentation and/or keying and/or routing can also be done during this stage. As is known in the art (cf. the references listed in section "Background"), supervised training can encompass, e.g., supervised learning based on a known outcome where a model is using a labeled set of training data and a known outcome variable or reinforcement learning (reward system).

In order to configure computation modules to represent different anatomical sub-structures that might be present in a dentition of a patient, provided in the form of at least one CAD file and/or a 3d tomographic file, in the supervised training step according to the first aspect training data are provided to the system, comprising:

3d representations of teeth of a human dentition; for each tooth a plurality of different possible shapes in different orientations is given, preferably examples having different possible scan defects and/or colors are also given 3d representations showing different (arts of) dentitions, i.e., showing which teeth are adjacent to another are given, preferably (parts of) dentitions having gaps due to missing teeth are also given 3d representations of possible boundaries between gingiva and teeth In those embodiments in which the system is configured to create at least one treatment plan it is advantageous if, in the supervised training step; training data is provided to the system, comprising:

(parts of) dentitions having correctly or at least acceptably aligned teeth (which can be added to a catalog of target dentitions)

(parts of) dentitions having misaligned teeth (which can be added to a catalog of starting dentitions), preferably with different degrees of misalignment (parts of) dentitions having teeth with varying degrees of misalignment (which can be added to a catalog of intermediary dentitions)

established sequences of intermediary dentitions leading from a starting dentition to a target dentition In those embodiments in which the system is configured to analyze supplemental information given in the form of training data in the form of 2d representations such as an X-ray picture the above-mentioned training steps have to be done also with 2d representations in order to enable the system to understand 2d representations. In order to enable the system to combine information from 3d and 2d representations, training data showing corresponding 3d and 2d representations of the same (part of) dentitions for many different (parts of) dentitions should be given.

Supervised training can be stopped once a desired accuracy is achieved by the system.

In a second aspect, supervised training can be done differently from the prior art: By way of example assume the sentence "tooth 41 has a dental filling" (referring by way of example to the ISO 3950 dental notation) is inputted via, the first interface as (possibly part of) supplemental information regarding the digital data record. The system has categories for teeth and possible attributes of teeth, e.g., in the "tooth" category different names are represented by objects such as "tooth 11", "tooth 12" and so on while in the "possible attributes" category different attributes are represented by objects such as "dental filling", "dental implant", "caries", "brittle" and so on. The verb "has" could be represented by a first functor between the "tooth" category and those objects of the "attributes" category which represent attributes a tooth might have and a second functor between the "tooth" category and a category the objects of which represent information whether a tooth is present in a dentition or not, and so on. There could also be category of sentences the objects of which are sentences. Connections between objects of the same category are represented by morphisms while connections between different categories are represented by functors, e.g., a functor might connect the object "tooth 41" to "dental filling" and to further information relating "tooth 41" in other categories, e.g., to the sentence "Tooth 41 shows caries.", and connections between functors are represented by natural transformations as is well known in category theory. The "tooth" category might be connected to another category with possible attributes that might be connected to the names, e.g., a distinction between molars and incisors. Functors can be mapped onto each other using natural transformations.

Let us assume that, the system has not yet learned the meaning of "tooth 41" (that, in the ISO 3950 notation, it is the first incisor on the lower right of a permanent dentition)

and the meaning of "dental filling".Upon trying to resolve the meaning of the sentence "Tooth 41 has a dental filling." by inputting "tooth 41" and "dental filling" into a functor (actually a bi-functor) which maps to a category of sentences, it realizes that "tooth 41" is a designation of a specific tooth and that "dental filling" is something a specific tooth might have but it does not know what type of tooth number 41 is. This prompts the system to output two questions via the second interface, namely, "What type of tooth is tooth 41?" and "What does tooth 41 have?" Once these questions have been answered, e.g., by a human supervisor or by consulting an external database, (e.g., "Tooth 41 is the first incisor on the lower right." and "A dental filling fills a cavity in a tooth.") the system will configure as many computation modules as necessary to store the newly learned information in the form of objects and morphisms in the correct categories. Another question might be "Is tooth 41 intact?". Once the questions regarding "tooth 41" have been answered the system can train a natural transformation between the functors that represent "dental filling" and "intact" because both concepts make sense with respect to "tooth 41".

Another categorical construct that can be used for unsupervised learning is a commutative diagram, as explained above starting from paragraph 152.

By way of example, in one embodiment, the system and method have been trained during supervised training in the following way:

For training, digital data records and photos concerning a multitude of different cases showing different types of orthodontic conditions were initially inputted to the system (in total, after several rounds of training, several hundred cases had been used for training, out of a reservoir of about 10000 exemplary cases), wherein for each case the following was provided:

input CAD files showing 3d representations of dentitions having malocclusions 20 to 30 files showing possible treatment plans and possible target dentitions 2 output CAD files allowing production of orthodontic appliances The input CAD files (in this example STL files were used) were created using a scan of each patient's dentition, one scan for the maxilla and one scan for the mandible. Some of the accompanying photos, provided in this example as JPEG files, showed each patient's dentition in total, some of the accompanying photos showed the individual teeth embedded in the gingiva, all for different viewing positions. Human operators manually separated the teeth from the gingiva and from each other using a CAD program according to the art and marked electronically where each of the individual teeth is shown in the photos showing the patient's total dentition and in the input CAD files. All of this data was inputted to the system and:

in this embodiment, a data, hub process was trained to calculate keys for the inputted data groups of computation modules were trained to represent the patient's dentition of the maxilla and the mandible groups of computation modules were trained to represent the individual teeth embedded in the gingiva groups of computation modules were trained to represent the manually separated teeth groups of computation modules were trained to output a virtual model of the patient's dentition based on the results of the before-mentioned computation modules in this embodiment, the computation modules were trained to recognize module-specific keys connections were configured manually by human operators between each of the following groups of computation modules:

the groups of computation modules representing the patient's dentition of the maxilla and the mandible the groups of computation modules representing the individual teeth embedded in the gingiva the groups of computation modules representing the manually separated teeth For each of the cases the system outputted CAD files (here: STL files), which initially little resembled the actual dentition of a patient. Therefore, the outputted STL files were manually corrected by human operators and returned to the system for another training round until, after several rounds and corrections by the human operators, the human operators concluded that the outputted STL files closely enough resembled the actual dentitions of the patient's.

In some embodiments, in order to enable the system to create treatment plans, a catalog of target dentitions (i.e., dentitions having no or only acceptable degrees of malocclusions) were inputted to the system (preferably pre trained to create a virtual model as described above) as well as different dentitions showing a variety of malocclusions. For each of the dentitions having malocclusions, human operators then created treatment plans (in the form of CAD files and CSV files) which, with, in this example, between twelve and sixteen steps of transformation, transformed each dentition from a starting dentition by way of intermediary (transformed) dentitions into one of the target dentitions. All of these dentitions (starting, intermediary and target were inputted into the system and the system was trained to automatically recognize the sequence from a starting dentition to a target dentition via intermediary dentitions. For some of the starting dentitions the human operators provided different sequences of intermediary dentitions which arrived at the same target dentition. Using test training data, it was checked by human operators that a starting dentition of the test training data was correctly transformed into a target dentition by the system with a desired accuracy. The system learned to output treatment plans in the form of CAD files and/or CSV files (which could also be used as production files for appliances) the system also has the capability to create different treatment plans for one and the same starting dentition.

It should be noted, that the step of training connections between the sequences of dentitions could have been replaced by manually configuring the connections between the computation modules representing a sequence of intermediary dentitions.

During configuration of the above-described system, in this embodiment, groups of computation modules were configured to represent a plurality of categorical constructs and random signals were inputted into some of computation modules. This enabled the system, even during supervised training, to partially learn by itself thereby shortening the necessary training time.

The above-described training process can also be used, if the system or method is intended to be able to process data different from input CAD files, such as X-ray images, CT-scans, written descriptions, CSV-files and the like.

By way of example, the system and method can be trained, according to any of the above described techniques, to recognize at least one of:

shape of at least the visible parts of individual teeth in isolation and/or as part of a dental arch shape of tooth parts which are not visible, like roots boundary between gingiva and teeth and/or between teeth presence of dental implants or dental fillings when provided with dental images in which these are recognizable natural language descriptions of teeth and/or dental implants and/or dental fillings malocclusions of a dentition or of a part of dentition desired state of dentition based on a given state (starting dentitions) and necessary transformations (intermediate dentitions) to get from the given state to the desired state (target dentition) in one or more steps Tedious and time-consuming tasks, such as separating gingiva from teeth, which in the prior art usually is done by specialists can be supported or gone by the system and method to automatically find a separation line on images in the process of separation. A cutting edge between teeth and/or a tooth and the gingiva can be found efficiently, wherein virtualized teeth in isolation can be manipulated and/or manufacturing machines can automatically (and with litte time resources required) produce the appropriate orthodontic appliances.

By way of example, the system and method can be trained to provide a virtual model in which deficient representation of the teeth (e.g., due to defective scans) have been automatically repaired, preferably by filling in defects (e.g., interpolation based on surrounding areas) and the teeth can be provided with movement options and/or movement fixations by providing supplemental information.

By way of a more detailed example, a computation module or computational group of computation modules can be trained to recognize a first kind of tooth (e.g., "molar") in the following way:

Learning data showing different embodiments of the first kind of tooth is inputted via the at least one first interface, e.g., to the at least one data hub process (if present), in some embodiments via the shared memory, which—if necessary—segments the input data into keyed data segments. A plurality of computation modules checks repeatedly whether there is any data present in the data, hub process and/or the shared memory with a matching (tolerance parameters can be given to determine when a key is at least approximately matching). If there is a module-specific data segment present, the data segment which is keyed with this key is loaded into the fitting computation module(s).

In dependence on the loaded keyed data segment(s) and, in some embodiments, with a requested tolerance, the computation module(s) generate(s) output using at least one machine learning method, the output being, e.g., a classification result for the loaded keyed data segment. This output data is used in the usual way of supervised learning by the neuronal network(s) of the computation module(s) to train the neuronal network(s) by a technique known in the art, e.g., back-propagation. If no data hub process is present, the groups of computation modules can check all of the digital data record provided as input for anatomical sub-structures which are represented by them which increases computational complexity.

Training of another computation module or computational group of computation modules to recognize a second kind of tooth (e.g., "incisor") can be done in the same way.

It should be noted that the phrase "system/method is trained to recognize a structure" does not necessarily mean that each computation module is trained to recognize every possible anatomical sub-structure that the system/method is able to recognize. On the contrary, for each structure that the system/method is able to recognize there may only be a part of the totality of computation modules (in some cases a single computation module, in other cases a group of computation modules having 2 to 10 or a few 10 computation modules, with respect to complex structures a group of computation modules having some 100 or some 1000 computation modules) that is trained to recognize that structure. In this sense, for a given computation module or group of computation modules and an inputted digital data record comprising a plurality of anatomical sub-structures only a part of that digital data record will be relevant for that computation module or group, namely that part which comprises the anatomical sub-structure for which the computation module or group is trained. In order to allow that part of computation modules to quickly find data that is relevant to them, if necessary, the inputted data can be segmented (if it does not come in segments) and can be provided with keys which can be recognized by the computation modules so that they know which data to act upon.

Supervised learning during training can encompass the step of asking an instructor (e.g., a human operator or a database), some anatomical sub-structure cannot be identified by the system itself.

By way of example, if the inputted data set is at least part of a dentition, the system and method will try to transform that, dentition by moving, scaling and rotating the anatomical sub-structures (these operation can be implemented by way of functors if categorical constructs are used) until it recognizes the anatomical sub-structure. In case recognition is not possible the system and method would ask a supervisor to identify the anatomical sub-structure and would, in the usual way regarding neuronal networks by changing weights, learn the dentition.

Regarding unsupervised learning (which can happen during training and/or during inference operation), in some embodiments, the system, by using random signals, creates or modifies anatomical sub-structures such as individual teeth or partial or complete dentitions which have not been provided as input. This enables the system and method to build a reservoir of, possibly more unusual, types of anatomical sub-structures which will help to accelerate identification of inputted data. The term "modifying structures" can mean to remove part of a given tooth or place a dental implant at a certain position in a dentition. This also helps the system and method to faster identify necessary transformations in inference operation.

It should be understood that—as is usual with respect to the workings of neuronal networks—the neuronal networks of the computation modules do not actually store pictures of anatomical sub-structures but have weights configured in such a way that they represent anatomical sub-structures. It is, of course, desirable to provide graphical representations of the anatomical sub-structures as an output for the benefit of a user of the system. This can be done by computation modules trained to create graphical representations.

Learning data showing different embodiments of the anatomical sub-structures is inputted via the at least one first interface, preferably to the at least one data hub process, in some embodiment via the shared memory, which—if necessary—segments the input data into keyed data segments.

A plurality of computation modules checks repeatedly whether there is any data present in the data hub process and/or the shared memory with a matching key (tolerance parameters can be given to determine when a key is at least approximately matching).

If there is a module-specific data segment present, the data segment which is keyed with this key is loaded into the fitting computation module(s).

In dependence on the loaded keyed data segment(s) and, in some embodiments, with a requested tolerance, the computation module(s) generate(s) output using at least one machine learning method, the output being, e.g., a classification result for the loaded keyed data segment. This output data is used in the usual way of supervised learning by the neuronal network(s) of the computation module(s) to train the neuronal network(s) by a technique known in the art, e.g., back-propagation.

Training of another computation module or computational group of computation modules to recognize a second type of anatomical sub-structure (e.g., "dental implant") can be done in the same way.

Unsupervised training can in some embodiments, happen using commutating diagrams which are represented by computation modules in the way described elsewhere in this disclosure. In some embodiments, unsupervised training can also happen due to the input of random signals and the creation of new concepts as described elsewhere in this description.

All statements in the present disclosure which are given with respect to the system only are also to be understood as referring to a method according to the invention.

BRIEF DESCRIPTION OF DRAWINGS

The Figures show schematic views of:

FIG. 6: steps according to an embodiment of the inventive method FIG. 8A: an example involving creation of a supplemental data record FIG. 8B: an example involving creation of a supplemental data record

FIG. 24C: an example how the system creates a virtual model and two treatment plans FIG. 25A: an example of digital representations to create deep drawing tools for deep drawing of aligners FIG. 25B: an example of digital representations to create deep drawing tools for deep drawing; of aligners FIG. 26A: an example of digital representations to create deep drawing tools for deep drawing; of aligners FIG. 26B: an example of digital representations to create deep drawing tools for deep drawing of aligners FIG. 27A: an example of digital representations to create deep drawing tools for deep drawing of aligners FIG. 27B: an example of digital representations to create deep drawing tools for deep drawing of aligners FIG. 28A: an example of digital representations to create deep drawing tools for deep drawing of aligners FIG. 28B: an example of digital representations to create deep drawing tools for deep drawing of aligners FIG. 29A: an example of digital representations to create deep drawing tools for deep drawing of aligners FIG. 29B: an example of digital representations to create deep drawing tools for deep drawing of aligners FIG. 30A: an example of digital representations to create deep drawing tools for deep drawing of aligners FIG. 30B: an example of digital representations to create deep drawing tools for deep drawing of aligners FIG. 37A: an example of digital representations to create deep drawing tools for deep drawing of aligners FIG. 37B: an example of digital representations to create deep drawing tools for deep drawing of aligners FIG. 38A: an example of digital representations to create deep drawing tools for deep drawing of aligners FIG. 38B: an example of digital representations to create deep (framing tools for deep drawing of aligners FIG. 39A: an example of digital representations to create deep drawing tools for deep drawing of aligners FIG. 39B: an example of digital representations to create deep drawing tools for deep drawing of aligners FIG. 40A: an example of digital representations to create deep drawing tools for deep drawing of aligners FIG. 40B: an example of digital representations to create deep drawing tools for deep drawing of aligners FIG. 41: an example of virtual models of dentitions in different steps of a treatment plan created by the system for a first treatment case FIG. 42: an example of virtual models of dentitions in different steps of a treatment plan created by the system for a first treatment case FIG. 43: an example of virtual models of dentitions in different steps of a treatment plan created by the system for a first treatment case FIGS. 44A and 45: output of the system in the form of visualizations of interproximal reduction according to the treatment plan for the example of FIGS. 41 to 43

FIG. 44B: output of the system in the form of CSV files of movement of teeth according to the treatment plan for the example of FIGS. 41 to 43

FIG. 44C: output of the system in the form of CSV files of movement of teeth according to the treatment plan for the example of FIGS. 41 to 43

FIG. 44D: output of the system in the form of CSV files of movement of teeth according to the treatment plan for the example of FIGS. 41 to 43

FIG. 44E: output of the system in the form of CSV files of movement of teeth according to the treatment plan for the example of FIGS. 41 to 43

FIG. 44F: output of the system in the form of CSV files of movement of teeth according to the treatment plan for the example of FIGS. 41 to 43

FIG. 44G: output of the system in the form of CSV files of movement of teeth according to the treatment plan for the example of FIGS. 41 to 43

FIG. 44H: output of the system in the form of CSV files of movement of teeth according to the treatment plan for the example of FIGS. 41 to 43

FIG. 44I: output of the system in the form of CSV files of movement of teeth according to the treatment plan for the example of FIGS. 41 to 43

FIG. 44J: output of the system in the form of CSV files of movement of teeth according to the treatment plan for the example of FIGS. 41 to 43

FIG. 44K: output of the system in the form of CSV files of movement of teeth according to the treatment plan for the example of FIGS. 41 to 43

FIG. 44L: output of the system in the form of CSV files of movement of teeth according to the treatment plan for the example of FIGS. 41 to 43

FIG. 44M: output of the system in the form of CSV files of movement of teeth according to the treatment plan for the example of FIGS. 41 to 43

FIG. 44N: output of the system in the form of CSV files of movement of teeth according to the treatment plan for the example of FIGS. 41 to 43

FIG. 46: an example of virtual models of dentitions in different steps of a treatment plan created by the system for a second treatment case FIG. 47: an example of virtual models of dentitions in different steps of a treatment plan created by the system for a second treatment case FIG. 48: an example of virtual models of dentitions in different steps of a treatment plan created by the system for a second treatment case FIG. 49: an example of virtual models of dentitions in different steps of a treatment plan created by the system for a third treatment case FIG. 50: an example of virtual models of dentitions in different steps of a treatment plan created by the system for a third treatment case FIG. 51: an example of virtual models of dentitions in different steps of a treatment plan created by the system for a third treatment case

There is a difference between a physical-point-of-view of the system 1 and an information-point-of-view. With respect to the former point of view the plurality of computation modules 7 can be viewed as a matrix (or a higher-dimensional tensor) in which each individual computation module 7 is addressed by an index, e.g., $C_{k,l}$. With respect to the latter point of view, categorical constructs are present which are represented by one or more computation modules 7. By way of example, a category comprising 1000 objects and/or morphisms might be represented by a matrix of, e.g., 50×4 computation modules 7. In other words, a, 1:1 correspondence between a single computation module 7 and a categorical construct does not need to exist and, in most embodiments, will not exist, however a 1:1 correspondence between groups of computation modules 7 and categorical constructs can exist. In the physical-point-of-view a data hub process 6 can be viewed as an index addressing computation modules 7 while in the information-point-of-view it can be seen as a base category of a fibered category having computation modules 7 as fibers.

Figure 1:
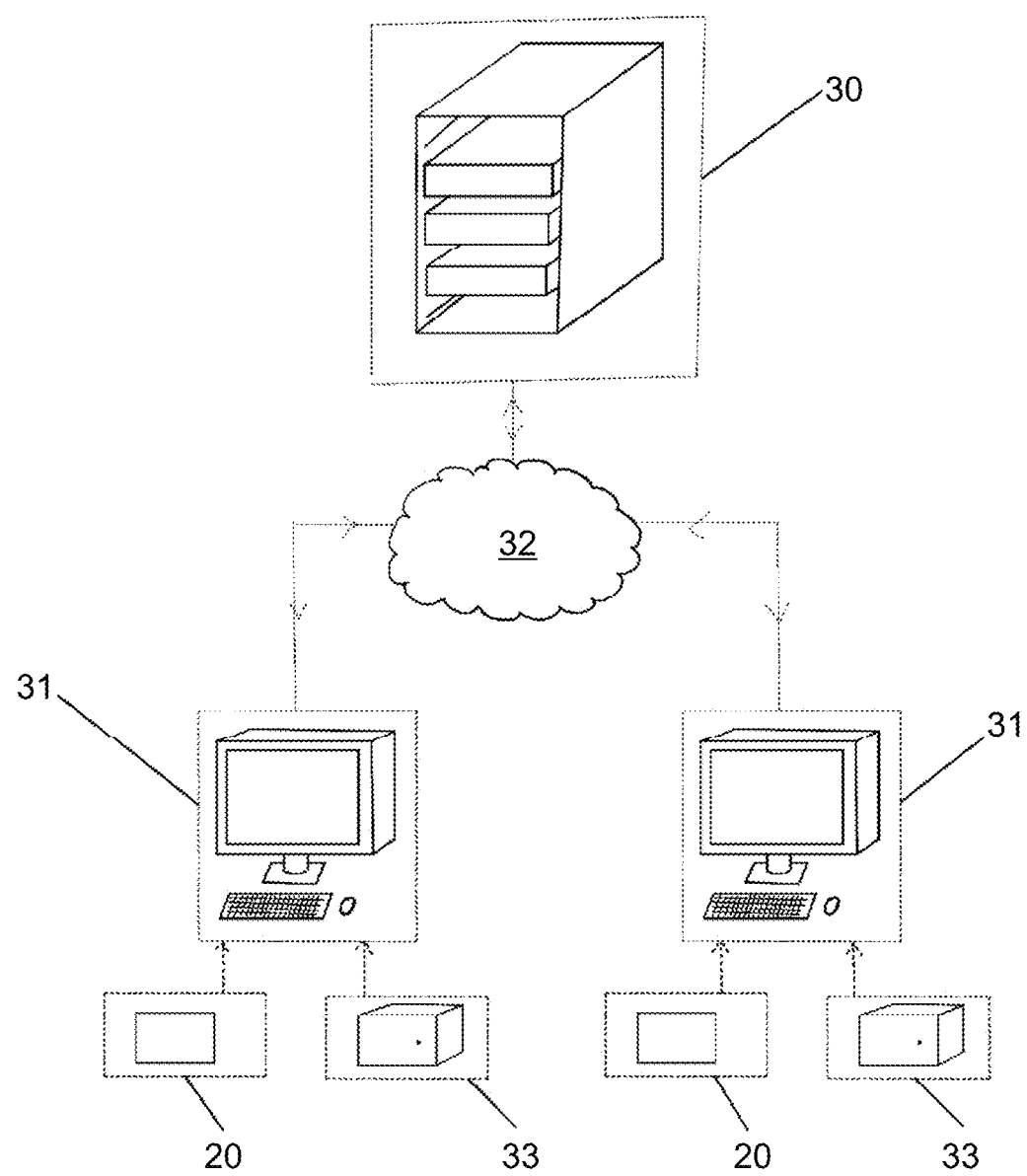
FIG. 1: a system with components provided on a server and components provided on client computers connected to the server by a communication network

FIG. 1 shows a preferred embodiment regarding the spatial distribution of a system 1 and method according to the invention. In such a system 1 at least:
said at least one shared memory device 4, and
said at least one co wilting device 5 are located on at least one server 30 and at least
said at least one first interface 2, and
said at least one second interface 3 are located in the form of at least one client program of the server 30 on a client computer 31 which is connected to said at least one server 30 by a communication network 32, preferably the internet.

Other than shown in FIG. 1 if a server-client architecture is used, the at least one first interface 2 and the at least second interface 3 could be located on the server 30 or some of the at least one first interface 2 and/or the at least second interface 3 could be located on the server 30 and some on the client computer 31.

Via the at least one first interface 2 the client computer 31 can be brought into connection with a scanner 33 and/or a file 20 comprising the at least one digital data record 17 and/or supplemental information can be provided to the client computer 31.

What is particularly advantageous about the system 1 and method of the present invention is that it can be used to directly read and/or process polygonal structures such as representations of the surface of anatomical sub-structures such as (parts of) teeth and gingiva, particularly in the form of CAD files, such as STL files or object files.

With the process according to the invention and the output of the system 1 and method it is possible to generate a computer-readable command file, e.g., at least one CAD file, e.g. an STL file or an object file, to directly instruct a manufacturing machine such as a CNC machine, a 3d printing machine, a casting machine, . . . , to produce appliances for die orthodontic condition efficiently with respect to time and material resources in a dentists office, ideally, while the patient is still waiting.

In such a system 1 it is preferred that at least one client program comprises a plugin in the form of an interface between at least one computer program running on said client computer 31, preferably a certified computer program, and the at least one server 30, wherein the at least one client program is configured to:
translate and/or edit, preferably essentially in real time, user inputs and/or data of the at least one computer program relating to the at least part of a dentition of patient to create the at least one digital data record 17 and/or
translate and/or edit, preferably essentially in real time, the output of the at least one second interface 3 for the at least one computer program (e.g., the virtual model 8 and/or at least one treatment plan 9 and building commands to build an orthodontic appliance)

In general, an operator (e.g., a doctor) has the possibility to configure the virtual model 8 and/or at least one treatment plan 9 within the at least one computer program, and to have the system 1 and method accordingly change the virtual model 8 and the at least one treatment plan 9, respectively. If according to the operator there exists, e.g., a more convenient way for a proposed movement of a tooth of the at least one treatment plan 9, the operator is able to adapt the at least one treatment plan 9 accordingly.

Figure 2:
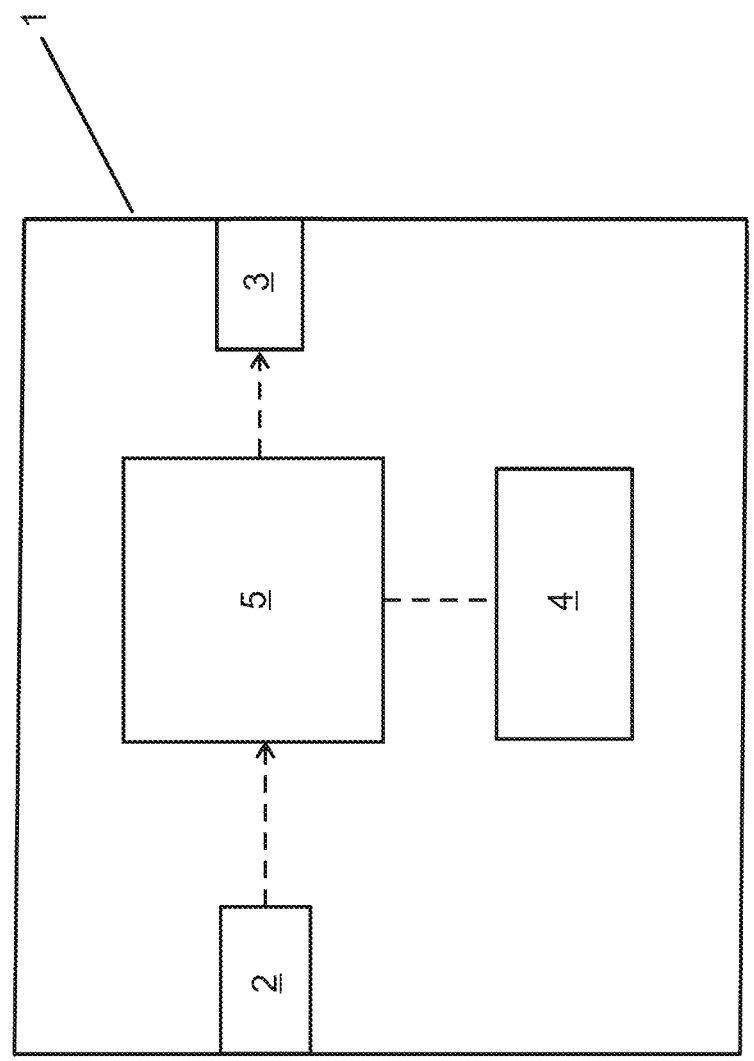
FIG. 2: a schematic view of a system according to an embodiment of the invention

FIG. 2 shows an embodiment of a system 1 comprising:
at least one first interface 2 for receiving input data ID
at least one second interface 3 for outputting output data OD
at least one shared memory device into which data can be written and read from
at least one computing device 5 to which the at least one first interface 2 and the at least one second interface 3 and the at least one shared memory device 4 are connected and which is configured to:
receive input data ID from the at least one first interface 2
send output data OD to the at least one second interface 3
read data from and write data into the at least one shared memory device 4

Figure 3:
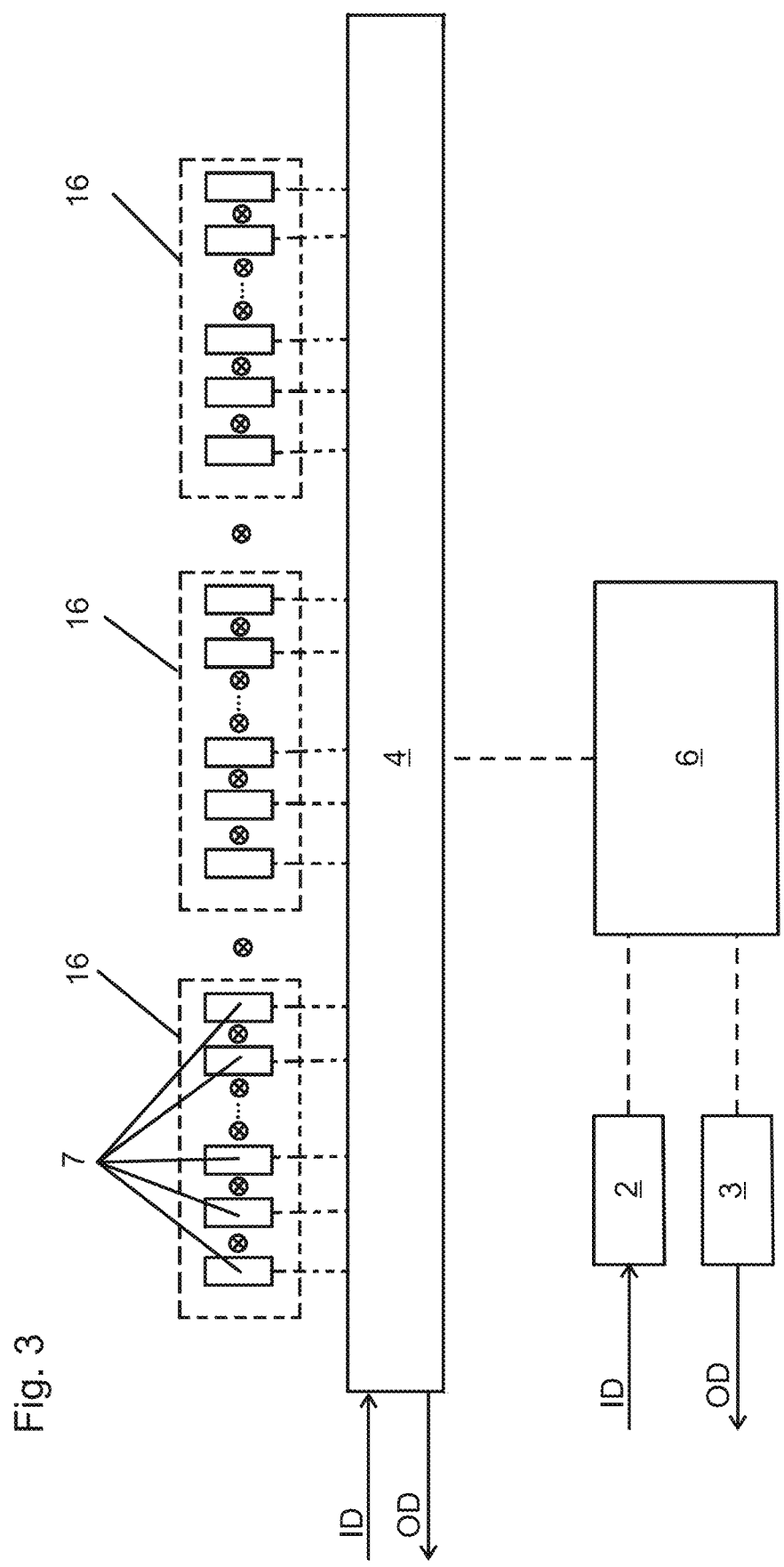
FIG. 3: the internal structure of the computing device and interactions between its components and other components of the system

FIG. 3 shows a plurality of computation modules 7 which, in some embodiments, are organized into logical computational groups 16 (which could be organized into logical meta-groups, but, this is not shown) and which, in this embodiment, interact with at least one data hub process 6 via a shared memory device 4. Input data ID in the form of a digital data record 17 is inputted via at least one first interface 2 into the shared memory device 4 and/or the at least one data huh process 4. Output data OD comprising at least a virtual model 8 is outputted into the shared memory device 4 and/or the at least one data hub process 6 and can be sent to the at least one second interface 3.

Figure 4:
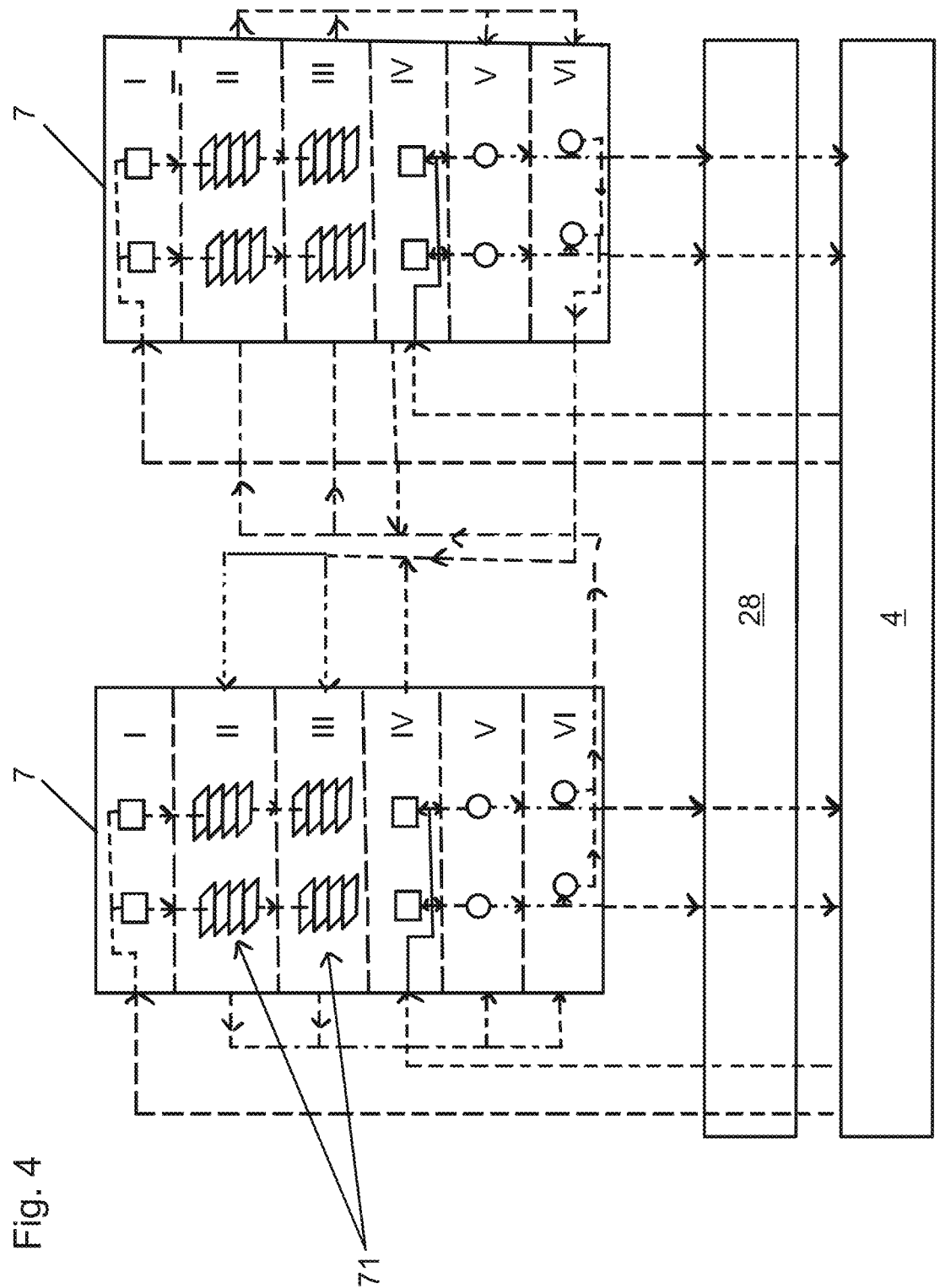
FIG. 4: the internal structure of computation modules and interactions between their components and other components of the system
Figure 19:
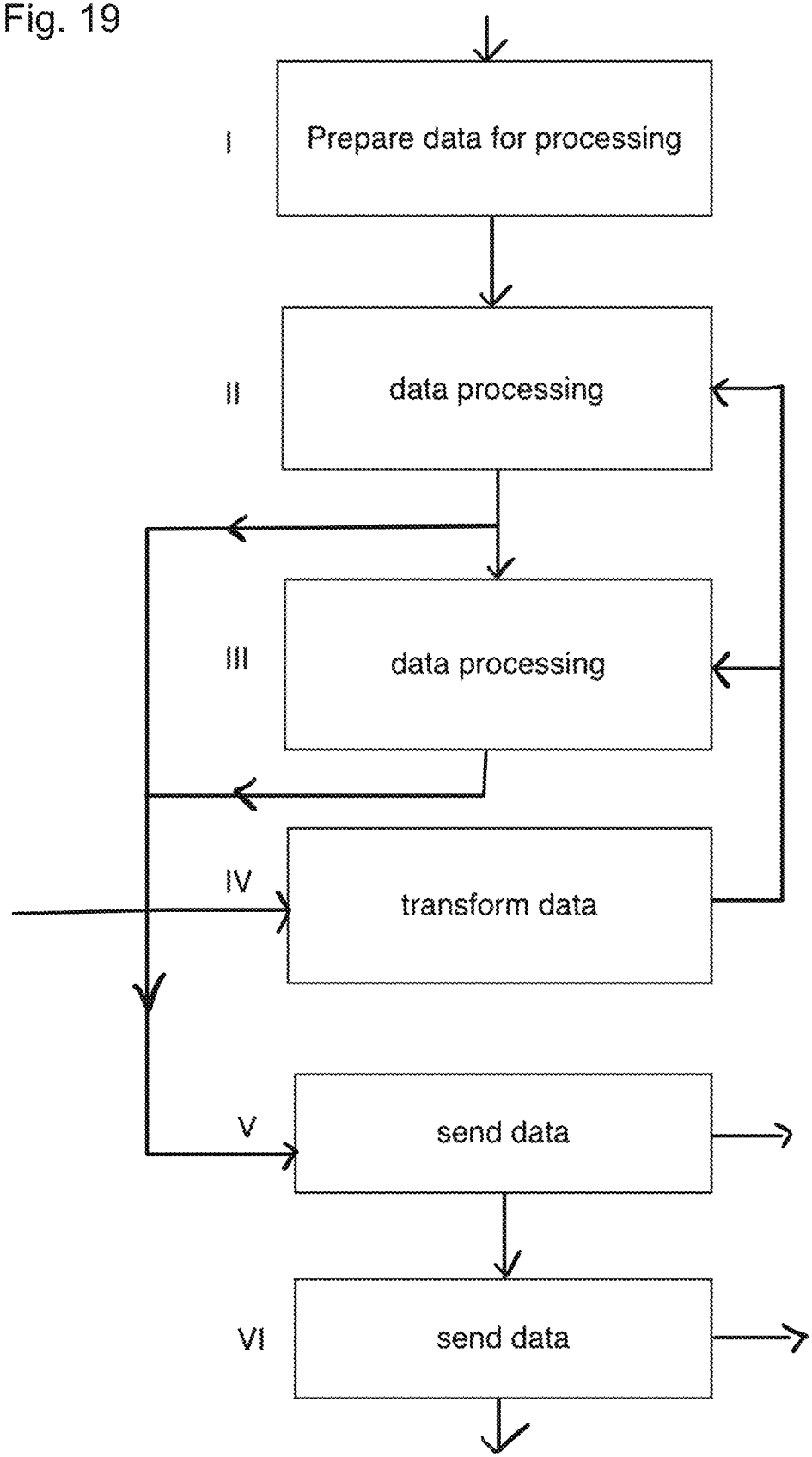
FIG. 19: a possible vertical hierarchical organization of a computation module

FIG. 4 shows the internal structure of computation modules 7 for an embodiment in which the computation modules 7 are provided with, e.g., six different layers I, II, III, IV, V, VI (the number of layers could be different for different computation modules 7). Steps of analyzing data, using such an anatomical sub-structure are also shown in FIG. 19. It can also be seen that a routing process 28 is present (in this embodiment separate from the data hub process 6 although in some embodiments it can form part of it, if a data hub process 6 is present) which knows which computation module 7 has to be connected with which other component of the system 1.

In some embodiments layer I might be configured to process module-specific keyed data segments $KS_i$ obtained from shared memory 4 or the data hub process 6 such as a target vector. This layer can prepare data to be better suited for processing by the at least one neuronal network 71, e.g., by topological down transformation, as is known in the art.

In some embodiments layer II and/or III might be configured to process data obtained from layer I and, possibly, from other computational modules 7, e.g., via neuronal networks 71 (by way of example ANNs are shown). These are the layers where machine learning takes place to cognitively process data during data analysis. In some embodiments, these layers can also receive information from other computation modules 7, e.g., from layers V or VI of these other computation modules 7.

In some embodiments layer IV might be configured to comprise at least one neuronal network 71 which, however, is not used for cognitive data processing but to transform data from the data hub process 6 or the shared memory 4 (such as an input vector) for layers II and III, e.g., by topological down transformation.

In some embodiments layer V and/or VI might be configured to comprise neuronal networks 71 which can be used to learn whether information represented by data is better suited to be processed in a different computation module 7 and can send this data accordingly to the data hub process 6 (preferably via the routing process 28) and/or the shared memory device 4 and/or at least one other computation module 7 where this data can be inputted, e.g., in layers II or III.

Figure 5:
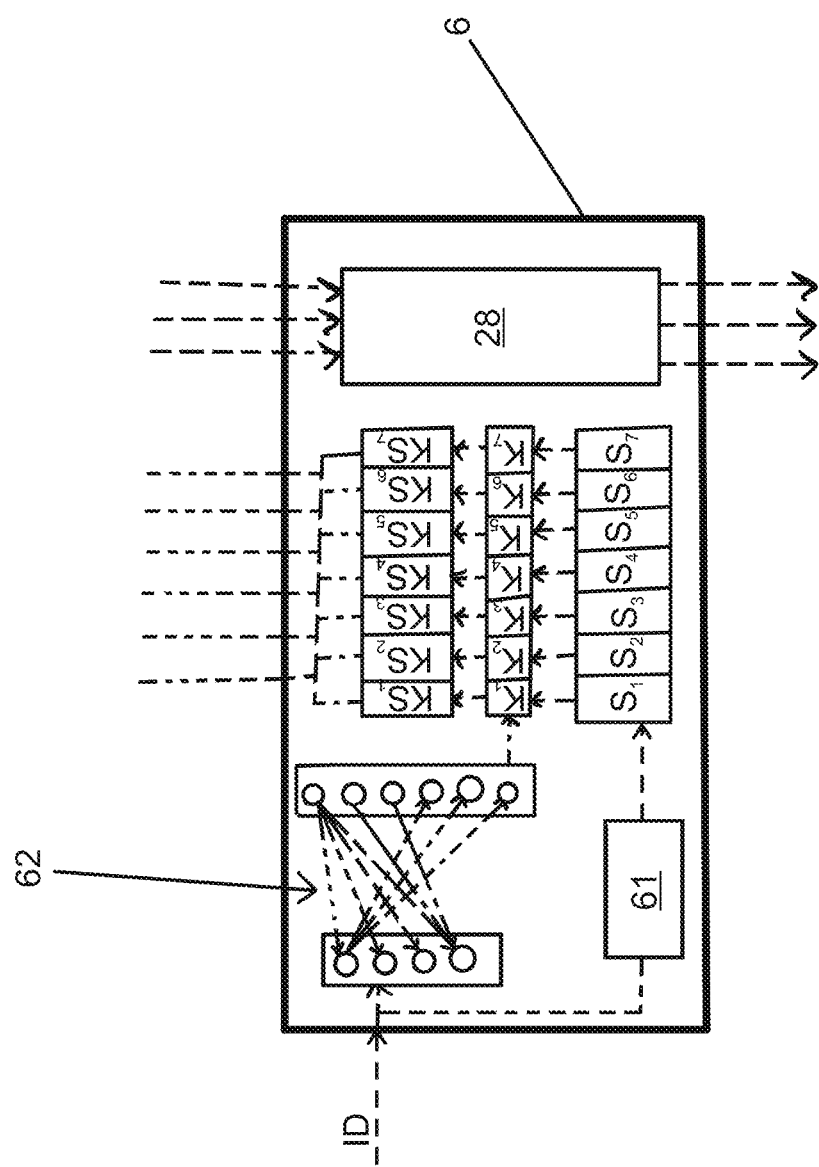
FIG. 5: the internal structure of a data hub process

FIG. 5 shows the internal structure of one of possibly several data hub processes 6 for an embodiment in which:
input data ID is segmented into data segments $S_1, \ldots, S_7$ by one, of possibly several segmentation sub-processes 61
keys $K_1, \ldots, K_7$ are determined by one of possibly several keying sub-processes 62 (in some embodiments at least one ART network might be used for that purpose)
the keys $K_1, \ldots, K_7$ assigned to the segments $S_1, \ldots, S_7$ to create keyed data segments $KS_1, \ldots, KS_7$ by one of possibly several keying sub-processes 62
the keyed data segments $KS_1, \ldots, KS_7$ are written into the shared memory device 4
an optional at least one routing process 28, here configured as a sub-process, which directs output provided by at least one of the computation modules 7 to at least one other computation module 7, the at least one routing process 28 accessing the shared memory device 4

FIG. 6 shows possible steps carried out by at least one data hub process 6 and at least one computation module 7:
input data ID is captured via the at least one first interface 2
keys $K_i$ are determined by one of possibly several keying sub-processes 62
input data ID is segmented into data segments $S_i$ by one of possibly several segmentation sub-processes 61
keyed data segments $KS_i$ are created by one of possibly several keying sub-processes 62
the keyed data segments $KS_i$ are provided to shared memory device 4
the computation modules 7 repeatedly check shared memory device 4 for module-specific keyed data segments $KS_i$
the computation modules 7 load their module-specific keyed data segments $KS_i$ if any are present, otherwise they stay idle
the computation modules 7 start data analysis on the module-specific keyed data segments $KS_i$
the computation modules 7 provide their output to shared memory device 4 and/or at least one data hub process 6 and/or at least one other computation module 7 and/or to the at least one second interface 3

Figure 7:
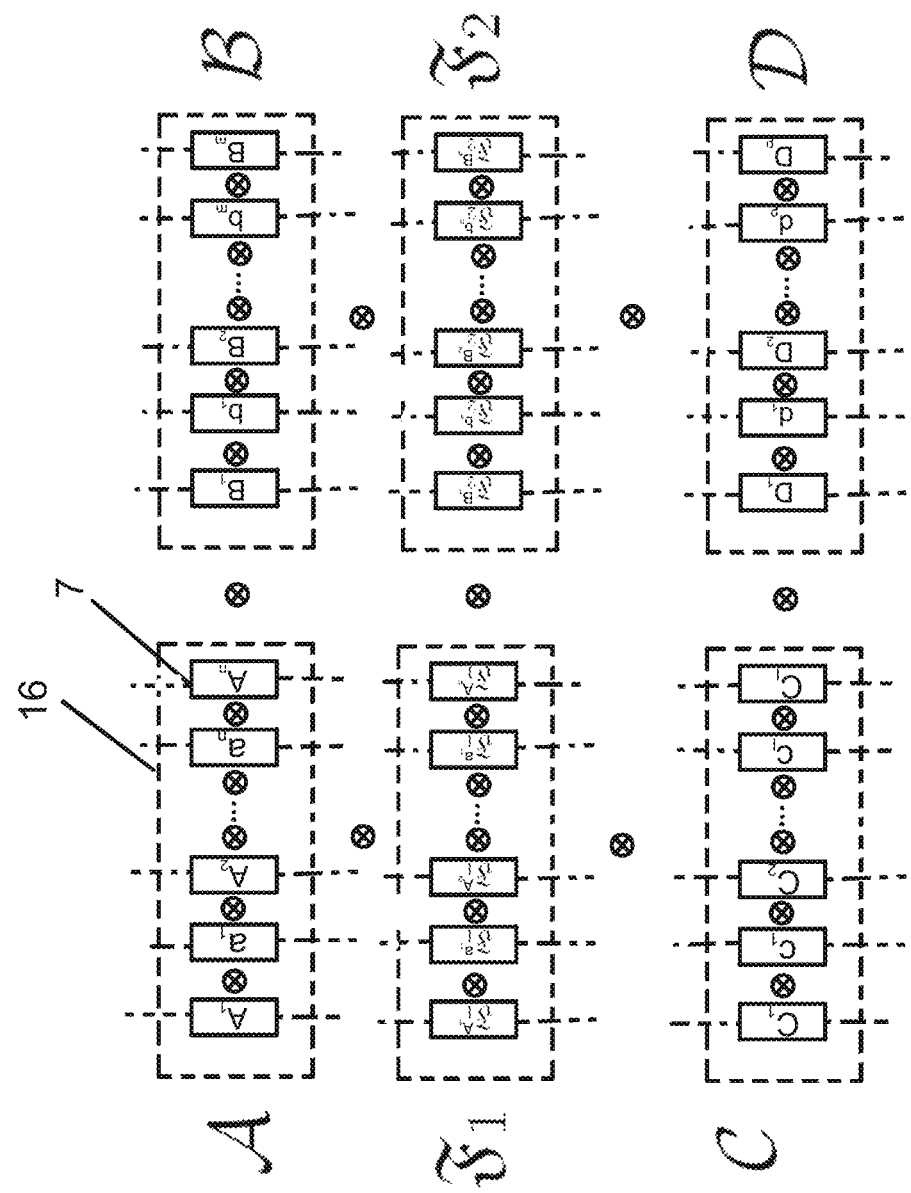
FIG. 7: computation modules representing categorical constructs

FIG. 7 shows how categorical constructs can be represented by computation modules 7 and their interactions in some embodiments. It should be noted that the number of computation modules 7 per computational group 16 can be different between computational groups 16 and that the representation of categorical constructs by computation modules 7 in no way relies on the organization of computation modules 7 into computational groups 16 or the internal (vertical) structure of computation modules 7.

In some embodiments different computational groups 16 may represent different categories $\mathcal{A}, \mathcal{B}, \mathcal{C}, \mathcal{D}$ wherein each computation module 7 represents an object $A_i, B_i, C_i, D_i$ or a morphism $a_i, b_i, c_i, d_i$ and other computational groups 16 may represent functors $\mathfrak{F}_1, \mathfrak{F}_2$ between different categories, e.g., $\mathfrak{F}_1: \mathcal{A} \sqcup \mathcal{C}$ and $\mathfrak{F}_2: \mathcal{B} \to \mathcal{D}$ such that $\mathfrak{F}_1^{A_i}(A_i) = C_i$, $\mathfrak{F}_2^{B_i}(B_i) = D_i$ for the objects of the categories and $\mathfrak{F}_1^{a_i}(a_i) = c_i$, $\mathfrak{F}_2^{a_i}(b_i) = d_i$ for the morphisms of the categories.

Different examples of more complex categorical constructs such as the projective limit $$\underset{\longleftarrow}{\lim} A_i$$

or natural transformations and their possible uses have already been discussed above and further examples will be discussed with respect to the following Figures.

It is an advantage of those embodiments of the present invention comprising categorical constructs that concepts which have been learned by computation modules 7 in a supervised way can be used by the system 1 to learn related concepts in an, at least partially, unsupervised way.

FIG. 8 shows an example in which a supplemented data record 19 is created out of a digital data record 17 and a supplemental data record 18. In this example the digital data record 17 is in the form of a 3d model of the dentition on a patient's mandible produced by an intraoral scan or a scan of an imprint of the dentition and the supplemental data record 18 is a digitalized analog X-ray picture of the patient's complete dentition (FIG. 8A). In the X-ray picture it can be seen that, with respect to the mandible, one of the canines has been replaced with a dental implant and one of the molars has a dental filling (FIG. 8A). This supplemental information is used in the creation of the virtual model 8 as shown by way of example (FIG. 8B: exclamation mark on canine and schematic representation of contour of dental filling on molar). It would also be possible to supplement the original digital data record 17 to create a supplemented data, record 19 (i.e., before creation of the virtual model 8).

Figure 9:
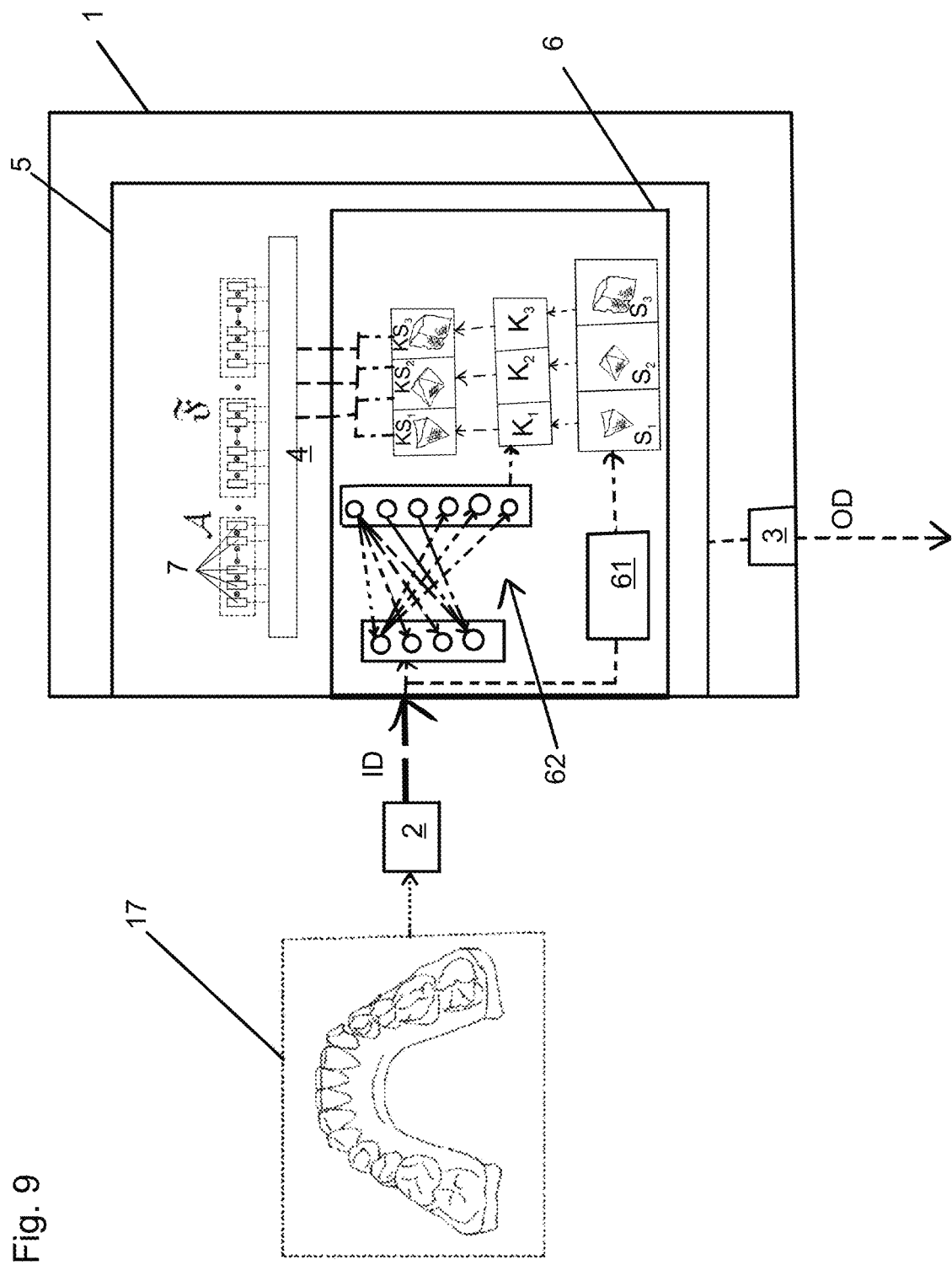
FIG. 9: an example involving recognizing different anatomical sub-structures of a digital data record

FIG. 9 shows an example where a number of computation modules 7 is configured to do structure recognition in order to enable them to recognize anatomical sub-structures in the shape of visible parts of different types of teeth such as incisors, molars, . . . irrespective of a color, rotational state or possible deformations of the anatomical (sub-)structures.

A digital data, record 17 representing a 3d model of a dental arch in a given spatial orientation having a plurality of anatomical sub-structures such as visible parts of different teeth and gingiva is provided as input data ID via the at least one first interface 2. The input data m is segmented and keys are created as described above. In the present example it is supposed that the segmentation sub-process 61 has been trained according to the art to recognize the presence of individual anatomical sub-structures in the input data ID and to create data segments $S_1, \ldots, S_n$ and the keying sub-process 62 has been trained according to the art to create keys $K_1, \ldots, K_n$ for the different anatomical sub-structures such that the data hub process 6 can create keyed data, segments $KS_1, \ldots, KS_n$ and provide them to the shared memory device 4 (in this Figure only two different anatomical sub-structures are shown by way of example).

Figure 10:
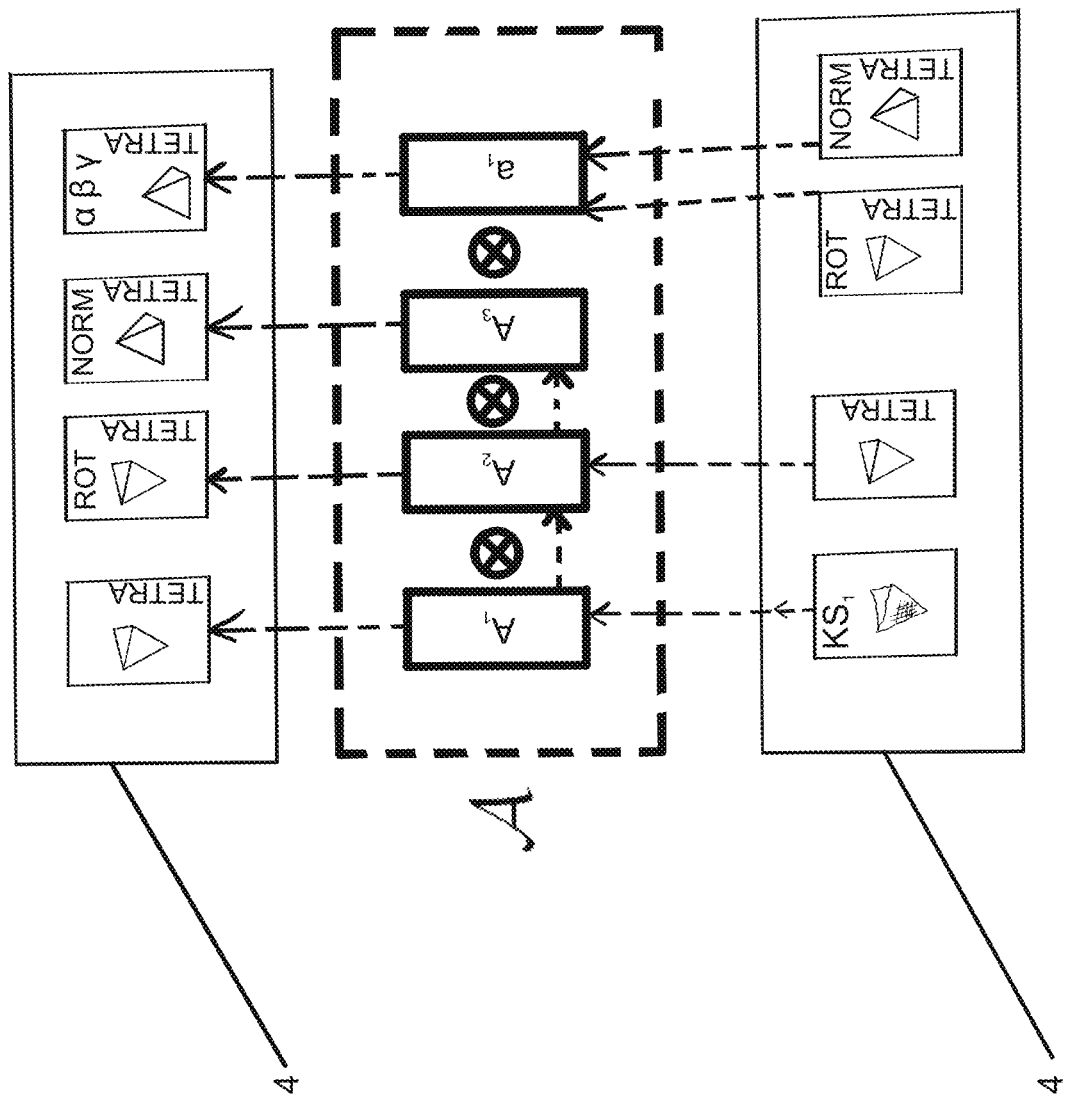
FIG. 10: a detail regarding the example of FIG. 9

Turning to FIG. 10 a number of computation modules 7 representing a category $\mathcal{A}$ is shown. The number of computation modules 7 is understood to be symbolic, n reality it will often be larger than the four computation modules 7 shown. A first computation module 7 represents an object $A_1$ and is trained to repeatedly access the shared memory device 4 looking for keyed data segments $KS_1$ representing objects. Although the computation modules 7 of this group are specifically trained to analyze incisors it could happen that they load a keyed data segment $KS_i$ which does not represent an incisor. In case during analysis a computation module 7 finds that a loaded keyed data segment $KS_i$ does not represent an incisor it can return this keyed data segment to the shared memory device 4 with the additional information "not an incisor" so that it will not be loaded by a computation module 7 of this group again.

Once a keyed data segment $KS_8$ has been loaded by the computation module 7 representing object $A_1$ analysis begins. This computation module 7 has been trained to recognize incisors irrespective of color or orientation. As an output it creates data representing $A_1$="incisor" a symbolized by the box showing an incisor and provided with the additional information "INCISOR". This output can either be sent directly to other computation modules 7 of this group or can be stored in the shared memory device 4. Here it is assumed that it is stored in the shared memory device 4 and the computation module 7 representing object $A_2$ loads this information. Computation module 7 representing object $A_2$ has been trained to recognize that the incisor is in a rotational state (with respect to a normalized state represented by object $A_3$) and outputs this information as $A_2$"INCISOR, ROT, $\alpha$, $\beta$, $\gamma$". However, it should be noted, that this computation module 7 does not necessarily encode the rotation group SO(3) since it is not necessary for the computation module 7 to know the exact values of $\alpha$, $\beta$, $\gamma$. Computation module 7 has been trained to receive as input $A_2$ and $A_3$, recognize the rotational state of an incisor by comparing these two inputs and to output this information which can be understood as representing the morphism $a_1:A_3 \rightarrow A_2$ as "INCISOR, ROT, $\alpha$, $\beta$, $\gamma$".

Of course other types of transformations than rotations could be represented, such as translations, reflections, . . . . It is to be understood that in some embodiments the morphism $a_1$ might be composed of several morphisms $a_1 = a_{11} \circ \ldots \circ a_{1k}$ wherein each morphism is encoded by one or several computation modules 7, e.g., of three morphisms $a_{11}$, $a_{12}$, $a_{13}$ wherein each morphism encodes rotation about a single axis or translation along a single direction.

Figure 11:
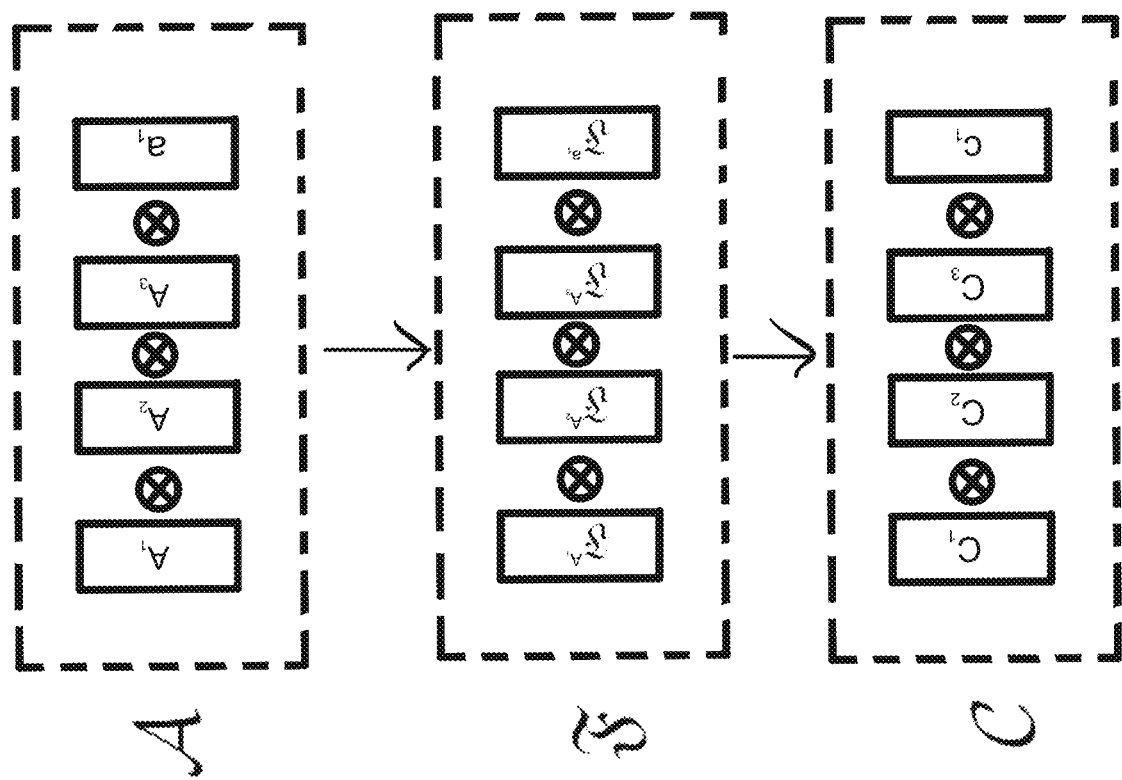
FIG. 11: a detail regarding the example of FIG. 9

FIG. 11 shows that using the categorical construct of a functor $\mathfrak{F}$ the objects and morphisms of category $\mathcal{A}$ (representing incisors) can be mapped to objects and morphisms of category C which, in this example, represents molars. In this way it is not necessary to train the computation modules 7 of category $\mathcal{C}$ once training of the computation modules 7 of category $\mathcal{A}$ is completed because all necessary concepts are mapped by the functor $\mathfrak{F}$ from category $\mathcal{A}$ to category $\mathcal{C}$ resulting in FIG. 12 (of course, the same can be done by a different functor with respect to a category representing a different type of tooth or gingiva). In this example the functor $\mathfrak{F}$ has been learned by comparing the rotational states of different anatomical sub-structures after these rotational states had been learned.

Figure 12:
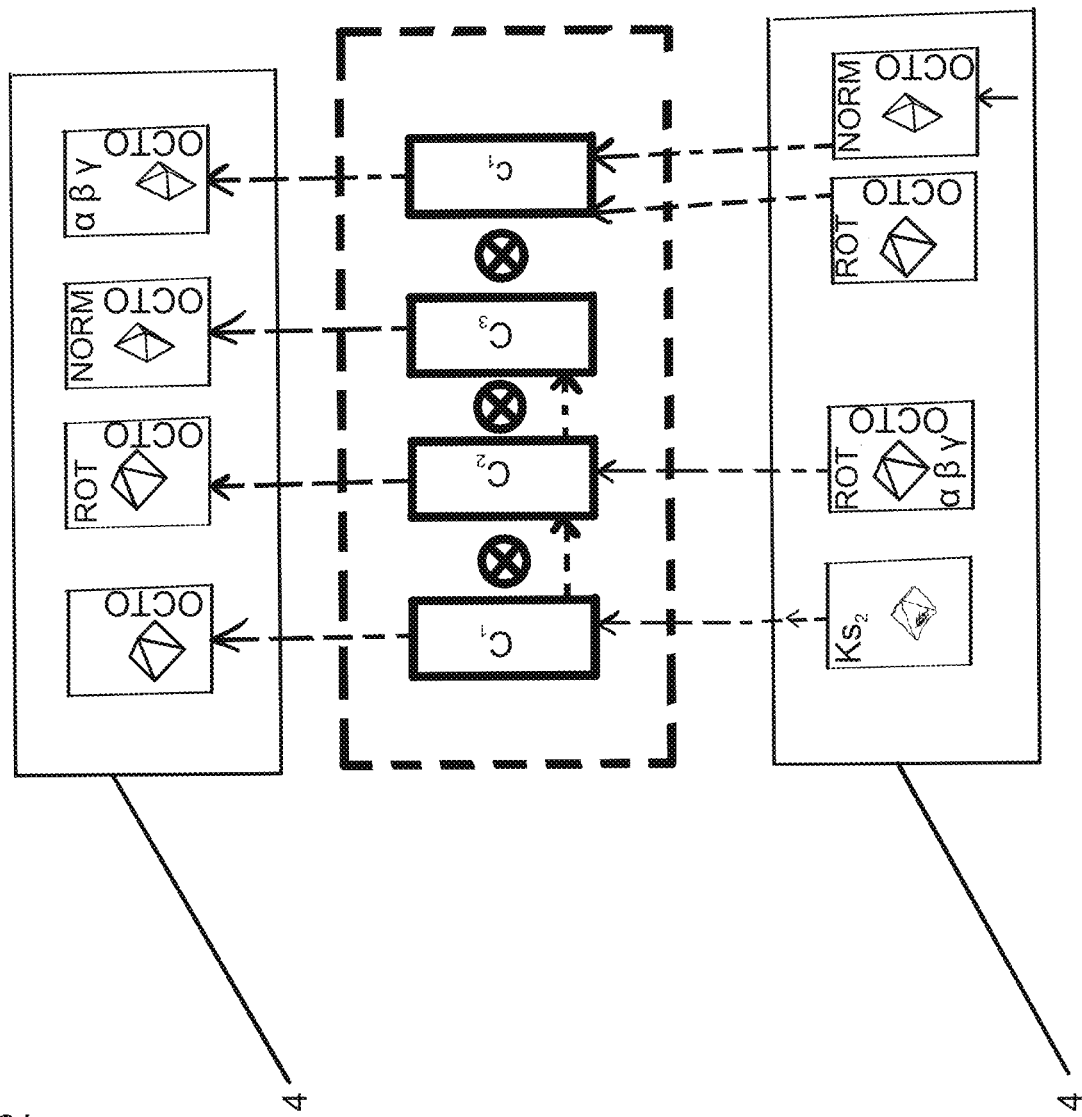
FIG. 12: a detail regarding the example of FIG. 9

FIG. 12 shows a number of computation modules 7 representing the category C of FIG. 11. The number of computation modules 7 is understood to be symbolic, in reality it will often be larger than the four computation modules 7 shown. A first computation module 7 represents an object $C_1$ and is trained to repeatedly access the shared memory device 4 looking for keyed data segments $KS_1$ representing molars. Although the computation modules 7 of this group are specifically trained to analyze molars it can happen that they load a keyed data segment $KS_i$ which does not represent a molar. In case during analysis it finds that a loaded keyed data segment $KS_i$ does not represent a molar it can return this keyed data segment $KS_i$ to the shared memory device 4 with the additional information "not a molar" so that it will not be loaded by a computation module 7 of this group again. Once a keyed data segment $KS_1$ has been loaded by the computation module 7 representing object $C_1$ analysis begins. This computation module 7 has been trained to recognize molars irrespective of color and orientation. As an output it creates data representing $C_1$="molar" as symbolized by the box showing a molar and provided with the additional information "MOLAR". This output can either be sent directly to other computation modules 7 of this group or can be stored in the shared memory device 4. Here it is assumed that it is stored in the shared memory device 4 and the computation module 7 representing object $C_2$ loads this information. Computation module 7 representing object $C_2$ has been trained to recognize that the molar is in a rotational state (with respect to a normalized state represented by object $A_3$) and outputs this information as $C_2$="MOLAR, ROT, $\alpha$, $\beta$, $\gamma$". Computation module 7 has been trained to receive as input $C_2$ and $C_3$, recognize the rotational state of the molar by comparing these two inputs and to output this information which can be understood as representing the morphism $c_1:C_3 \rightarrow C_2$ as "MOLAR, ROT, $\alpha$, $\beta$, $\gamma$".

Figure 13:
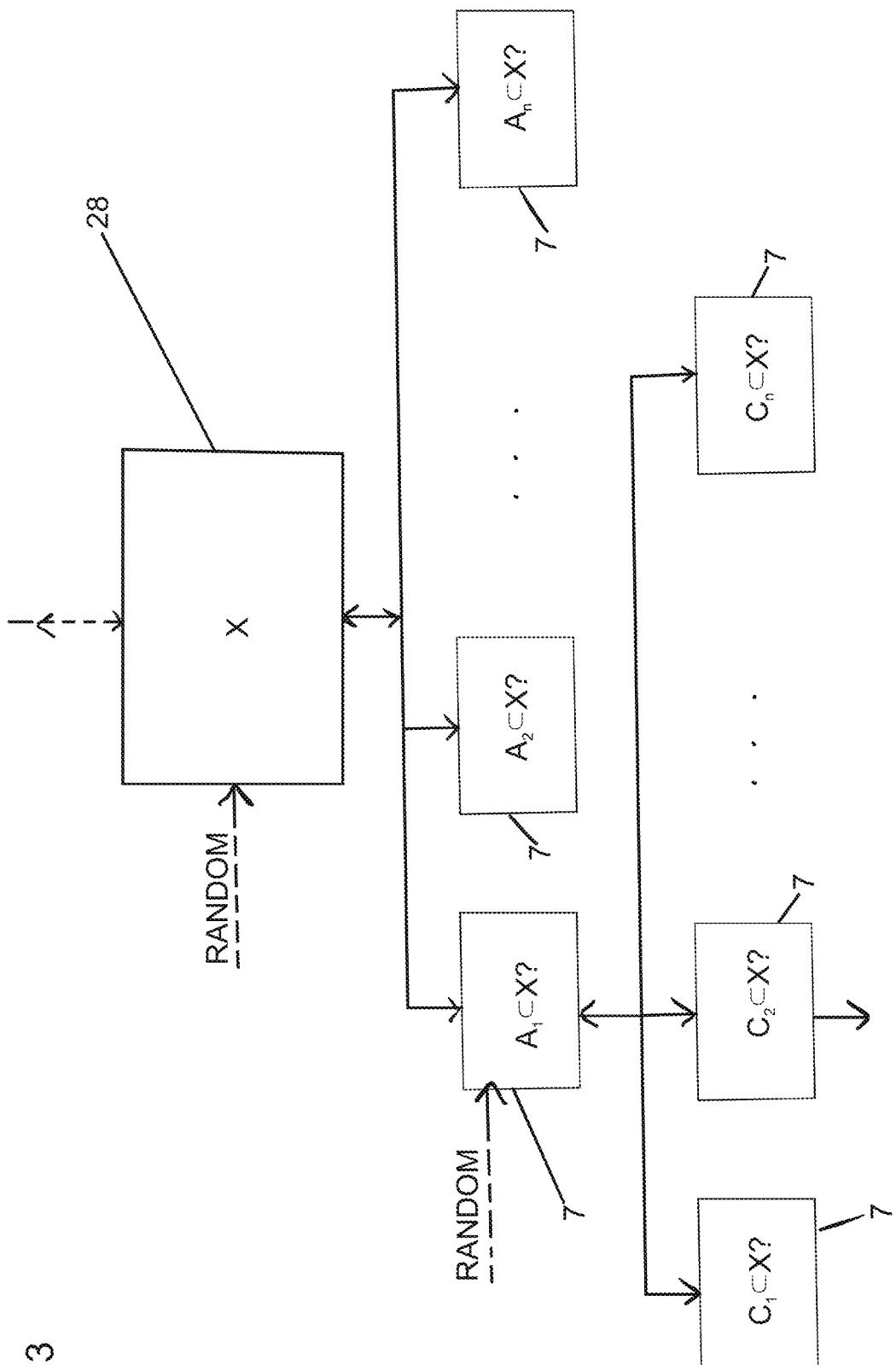
FIG. 13: an example involving data processing

FIG. 13 shows how, in some embodiments, the system 1 can analyze complex data by making use of different computation modules 7 which are each trained to recognize specific data. Some data X is inputted to the routing process 28 (or a different structure such as a sufficiently complex arrangement of computation modules 7) which sends this data to different computation modules 7. Each computation module 7 checks whether it knows (at least part of) the data X by checking, whether $a_i$ forms part of data X (here represented by the mathematical symbol for "being a subset of"). If the answer is "yes" it reports this answer back to sub-process 63. If the answer is "no" it can report this answer back to sub-process 63 or, in a preferred embodiment at least with respect to some computational modules 7, sends the data (segment) to at least one other computation module 7 (which can, e.g., form part of a, category that might be better suited to recognize this data). By way of example, data X might represent some anatomical sub-structure such as an incisor or (part of) a sentence such as "Pre-molar number 34 is replaced by a dental implant.".

In a, first example, the computation mom es 7 of a first category $\mathcal{A}$ might represent objects $A_i$ that represent anatomical sub-structures in the form of differently rotated incisors, while the computation modules 7 of second category $\mathcal{C}$ might represent objects $C_i$ in the form of differently rotated molars.

In a, second example, the computation modules 7 of a first category $\mathcal{A}$ might represent objects $A_i$ that represent nouns referring to a type of tooth and possible teeth damages (e.g., "incisor" or "molar" or "caries") or verbs (e.g., "has") referring to a first topic (e.g., "possible damages of teeth"), while the computation modules 7 of second category $\mathcal{C}$ might represent objects $C_i$ that represent nouns referring to artificial anatomical sub-structures (e.g., "dental filling", "dental implant") or verbs (e.g., "replaced by" or "shows") referring to a second topic (e.g., "modification or replacement of teeth") The computation modules 7 of the first category $\mathcal{A}$ will not be able to recognize data X in the form of a sentence concerning, e.g., a dental implant (since they only know possible damages of teeth) and will either give this information to the routing process 28 or, as shown in this Figure, can send this data X to computation modules 7 of the second category C which will be able to recognize the data X.

In preferred embodiments, the system 1 is enabled to create new concepts itself (cf. FIG. 13) by inputting a random signal RANDOM to at least one layer of the neuronal network(s) 71 of a computation module 7 such that the inputs of the neurons which, after integration, are used by an activation function $\sigma$ of the known kind of the neuronal network 71 to determine whether a certain neuron 21 will fire or not, are modified. In this way, a neuronal network 71 which is inputted with information regarding an anatomical sub-structure will base its computation not on the inputted information alone but on the inputted information which was altered by the random signal. In FIG. 13 this is shown by the signal line denoted "RANDOM". In some embodiments, if a hierarchically structured computation module 7 is used, this random signal RANDOM could be provided to the at least one neuronal network 71 present in layer III.

Figure 14:
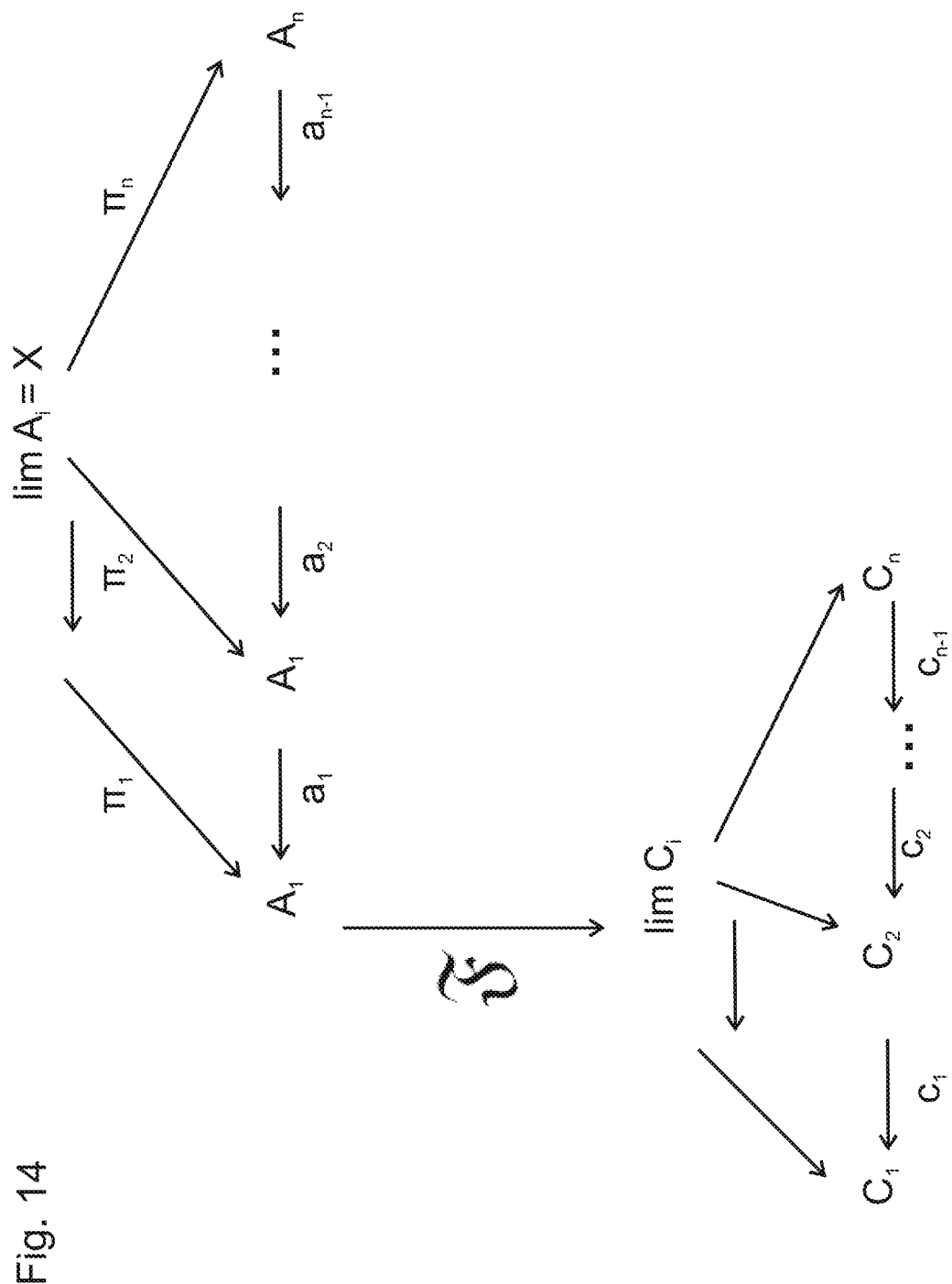
FIG. 14: the example of FIG. 13 using categorical constructs

FIG. 14 shows how a projective limit can be used for the process described in FIG. 13, e.g., by the routing process 28 of the data hub process 6 and/or by individual computation modules 7 and/or groups 16 of computation modules 7: data X which is to be interpreted is inputted to a computation module 7 (depending on the complexity of the data it will, in practice, often have to be a group 16 of several computation modules 7) which is interpreted to represent the projective limit of the data X which is interpreted to consist of a sequence of data segments $$A_1 \xleftarrow{a_1} A_2 \xleftarrow{a_2} \ldots \xleftarrow{a_{n=k-1}} A_{n=k}$$

The projective limit is the object $$\xleftarrow{\lim} A_i$$

together with morphisms $\pi_i$ which means that the sequence $A_{n=1}, \ldots, A_{n=k}$ is projected onto its ith member $A_{n=i}$. The system 1 can remember how the data X was segmented, e.g., use of the projection morphisms $\pi_i$ and morphisms $a_i$. Although not shown in FIG. 13, input of random signals RANDOM could also be present.

Figure 15:
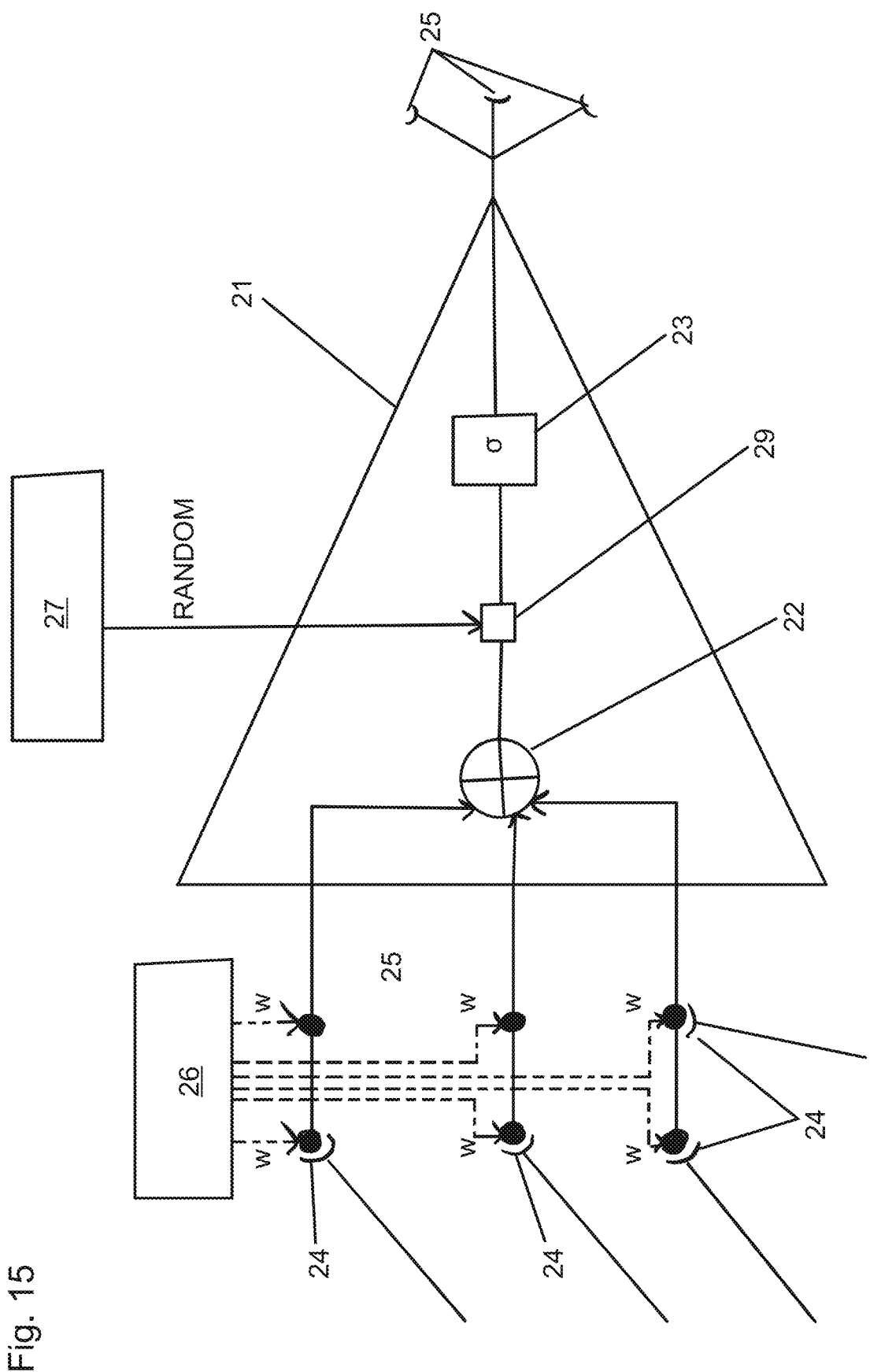
FIG. 15: an example showing a single artificial neuron having a receptor for a random signal

FIG. 15 shows a single artificial neuron 21 of an artificial neuronal network 71. The artificial neuron 21 (in the following in short: "neuron 21") has at least one (usually a plurality of) synapse 24 for obtaining a signal and at least one axon for sending a signal (in some embodiments a single axon can have a plurality of branchings 25). Usually, each neuron 21 obtains a plurality of signals from other neurons 21 or an input interface of the neuronal network 71 via a plurality of synapses 24 and sends a single signal to a plurality of other neurons 21 or an output interface of the neuronal network 71. A neuron body is arranged between the synapse(s) 24 and the axon and comprises at least an integration function 22 for integrating the obtained signals according to the art and an activation function 23 to decide whether a signal is sent by this neuron 21. Any activation function 23 of the art can be used such as a step-function, a sigmoid function, . . . . As is known in the art, the signals obtained via, the synapses 24 can be weighted by weight factors w. These can be provided by a weight storage 26 which might form part of a single computation module 7 or could be configured separately from the computation modules 7 and could provide individual weights w to a plurality (or possibly all) of the neuronal networks 71 of the computation modules 7. These weights w can be obtained as known in the art, e.g., during a training phase by modifying a pre-given set of weights w such that a desired result is given by the neuronal network 71 with a desired accuracy.

In some embodiments the neuron body can comprise a receptor for obtaining a random signal RANDOM which is generated outside of the neuronal network 71 (and, preferably, outside of the computation module 7). This random signal RANDOM can be used in connection with the autonomous creation of new concepts by the system 1.

The neurons 21 of a neuronal network 71 can be arranged in layers $L_1, L_2, L_3$ (which are not to be confused with the layers I-VI of a computation module 7 if the computation module 7 has a hierarchical architecture).

In some embodiments, the layers $L_1, L_2, L_3$ will not be fully connected, in other embodiments they will be fully connected.

Figure 16:
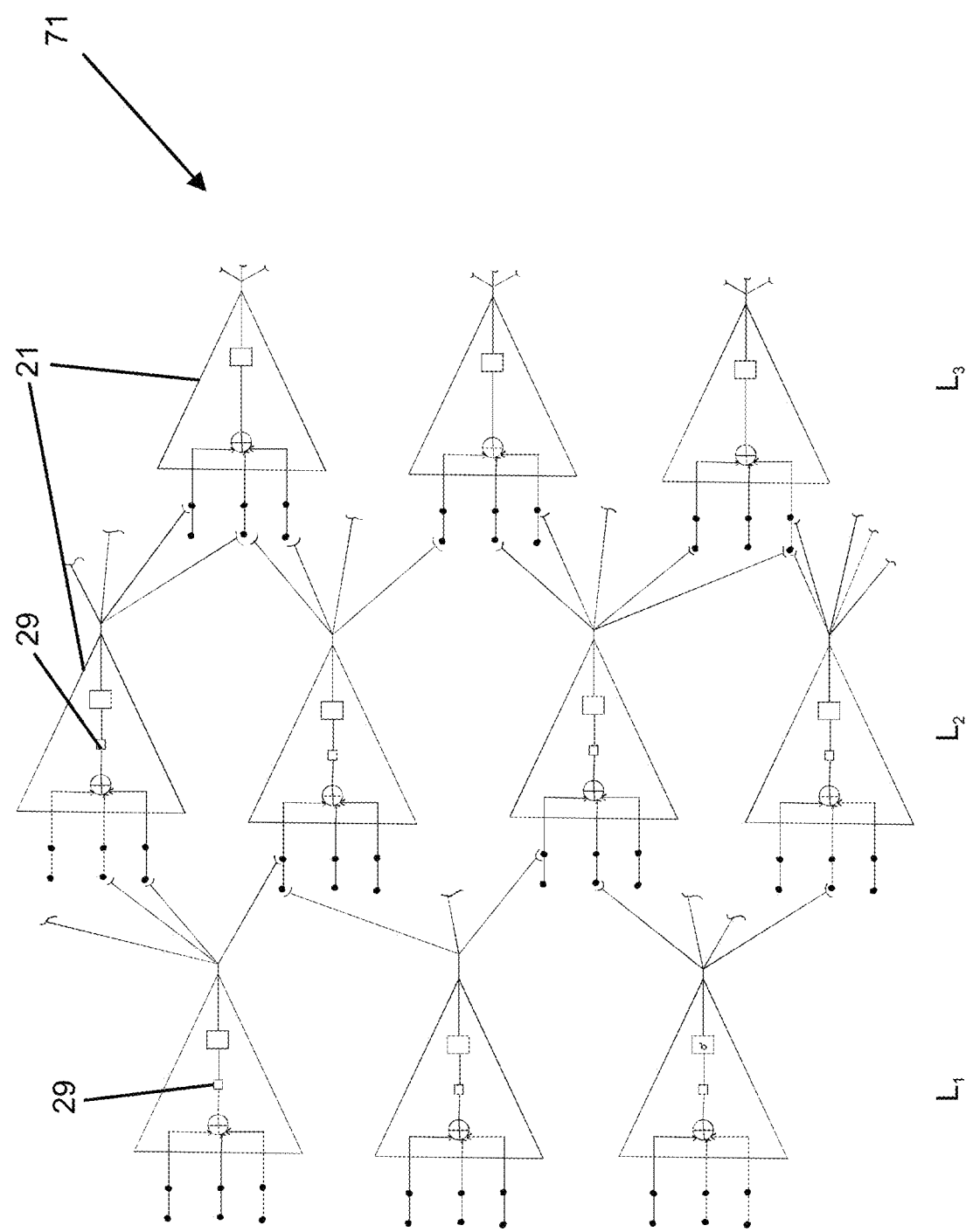
FIG. 16: an example of a neuronal network having a plurality of neurons as shown in FIG. 15

FIG. 16 shows three layers $L_1, L_2, L_3$ of neurons 21 which form part of a neuronal network 71. Not all of the connections between the neurons 21 are shown. Some of the neurons 21 are provided with a receptor 29 for obtaining a random signal RANDOM.

Figure 17:
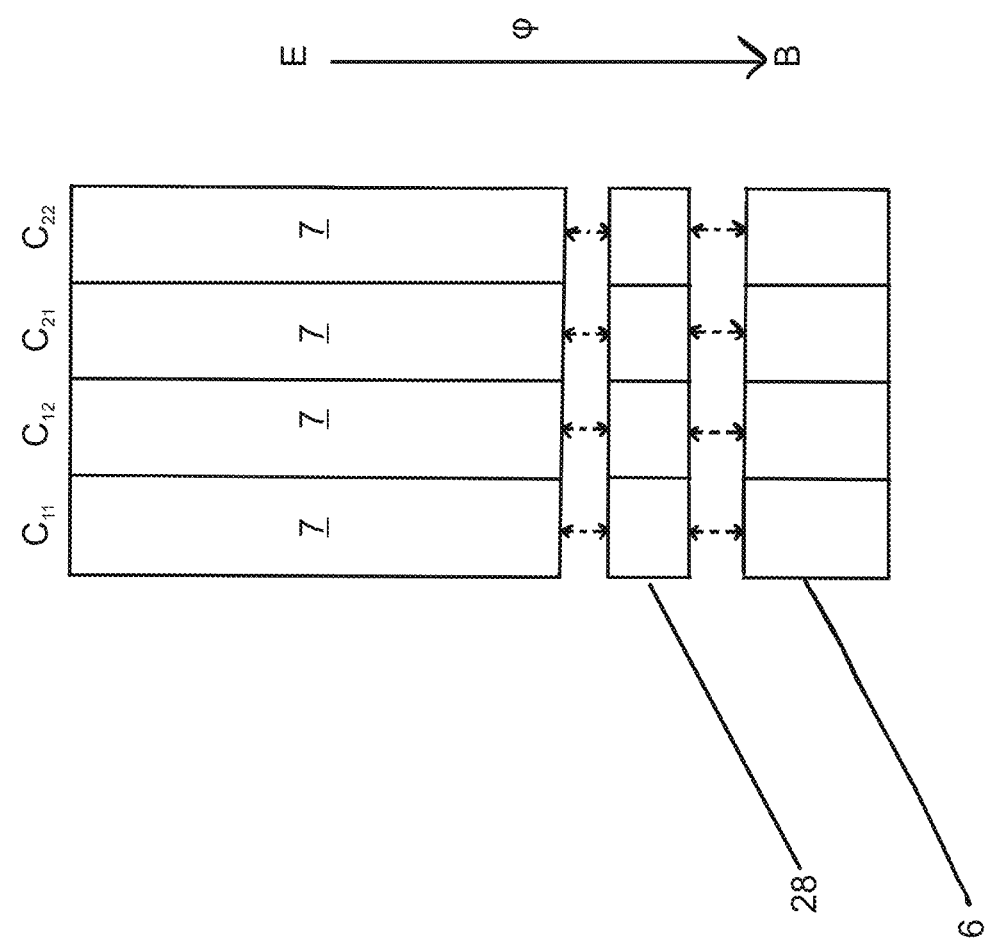
FIG. 17: a correspondence between computational modules and a categorical construct

FIG. 17 shows, by way of example, how a plurality of computation modules 7 (the chosen number of four is an example only) $C_{11}, C_{12}, C_{21}, C_{22}$ which form part of a tensor (here a 2×2 matrix) is used to represent a single category $\varepsilon$ and how, in the information-point-of-view, this category $\varepsilon$ is connected to a base or index category $\mathcal{B}$ via a functor $\phi(\varepsilon)$ and can be viewed as a fibered category while in the physical-point-of-view the four computation modules 7 are connected via the routing process 28 to the data hub process 6. The routing process and/or the data hub process 6 know where the information provided b the computation modules 7 has to be sent to.

Figure 18:
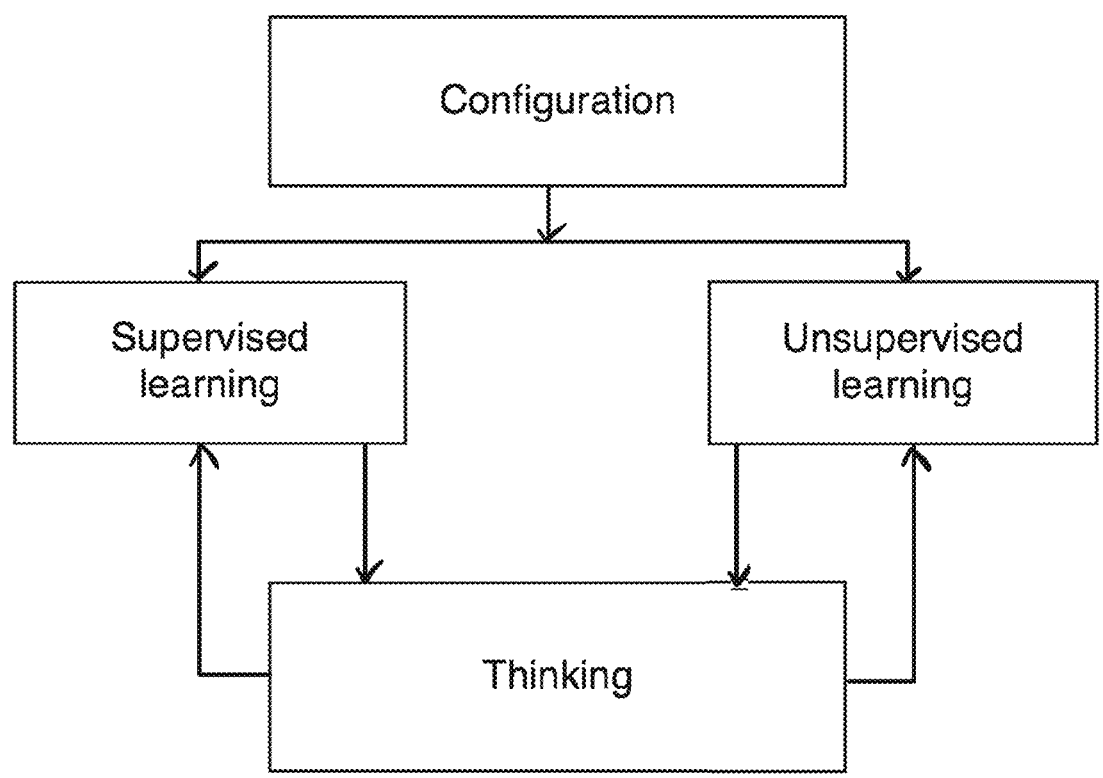
FIG. 18: different phases in the operation of a.n inventive system or method

FIG. 18 shows that although, approximately speaking, different phases can be thought of being present in the operation of an embodiment of a system 1 according to the invention, at least some of these phases can be thought of being temporally overlapping or being present in a cyclic way:

A first phase is denoted as "Configuration". In this phase the basic structures of the system 1 are configured such as the presence of a data hub process 6, the presence of the computation modules 7, possibly configuration of categorical structures, configuration of auxiliary processes and the like.

Once this first phase is finished the system 1 can start with supervised training, e.g., as is known in the art (by providing training data to the neuronal networks and adjusting weights until a desired result is achieved with a desired accuracy). It is also possible (additionally or alternatively) that the system 1 receives input data ID, e.g., by way of a sensor or by accessing an external database, analyzes the input data ID using the computation modules 7 and checks back with an external teacher, e.g., a human operator or an external database or the like, whether the results of the analysis are satisfactory and/or useful. If so, supervised learning is successful, otherwise, another learning loop can be done.

In addition to supervised learning, unsupervised learning ca be started by the system 1 in the above-described way using categorical constructs such as objects, morphisms, commutative diagrams, functors, natural transformations, pullbacks, pushouts, projective limits, . . . .

In addition to the phases of supervised and unsupervised learning, once a certain level of knowledge has been achieved by the system 1, the creation of new concepts, i.e., thinking, can be done using random signal RANDOM inputs as described above. Once it has been checked that a new concept makes sense and/or is useful (i.e., is logically correct and/or is useful for data analysis) this new concept can be used in supervised and unsupervised learning processes such that there can be a loop (which can be used during the whole operation of the system 1) between learning (unsupervised and/or supervised) and thinking.

FIG. 19 shows an embodiment in which at least some of the computation modules 7 have a vertical hierarchical organization with, e.g., six layers I-VI. Arrows show the flow of information. The term "vertical organization" means that the different layers can depicted as being stacked upon each other, it does not mean that information could only flow in a vertical direction.

Layer I is configured to process module-specific keyed data segments obtained from shared memory 4. This layer can prepare data to be better suited for processing by the at least one neuronal network 71, e.g., by topological down transformation. This data can comprise, e.g., a target vector for the neuronal networks 71 in layers II and III.

Layers II and III can comprise at least one neuronal network 71 each, each of which processes data obtained from layer I and, possibly, from other computational modules 7. These are the layers where machine learning can take place to process data during data analysis in a cognitive way using well-known neuronal networks such as general ANNs or more specific ANNs like MfNNs, LSTMs, . . . (here synaptic weights w are modified during training to learn pictures, words, . . . ). In some embodiments, these layers can also receive information from at least one other computation module 7, e.g., from layers V or VI of the at least one other computation module 7. In some embodiments, layer III contains at least one neuronal network 71 which receives random signals RANDOM as described above.

Layer IV can comprise at least one neuronal network 71 which, however is not used for cognitive data processing but to transform data for layers II and III, e.g., by topological down transformation. This data can comprise, e.g., an input vector for the neuronal networks 71 in layers II and III.

In layers V and VI neuronal networks 71 can be present which can be used to learn whether information represented by data is better suited to be processed in a different computation module 7 and can be used to send this data accordingly to the data hub process 6 and/or the shared memory 4 and/or routing processes 28 and/or directly to another computation module 7 where this data can he inputted, e.g., in layers II or III.

Figure 20:
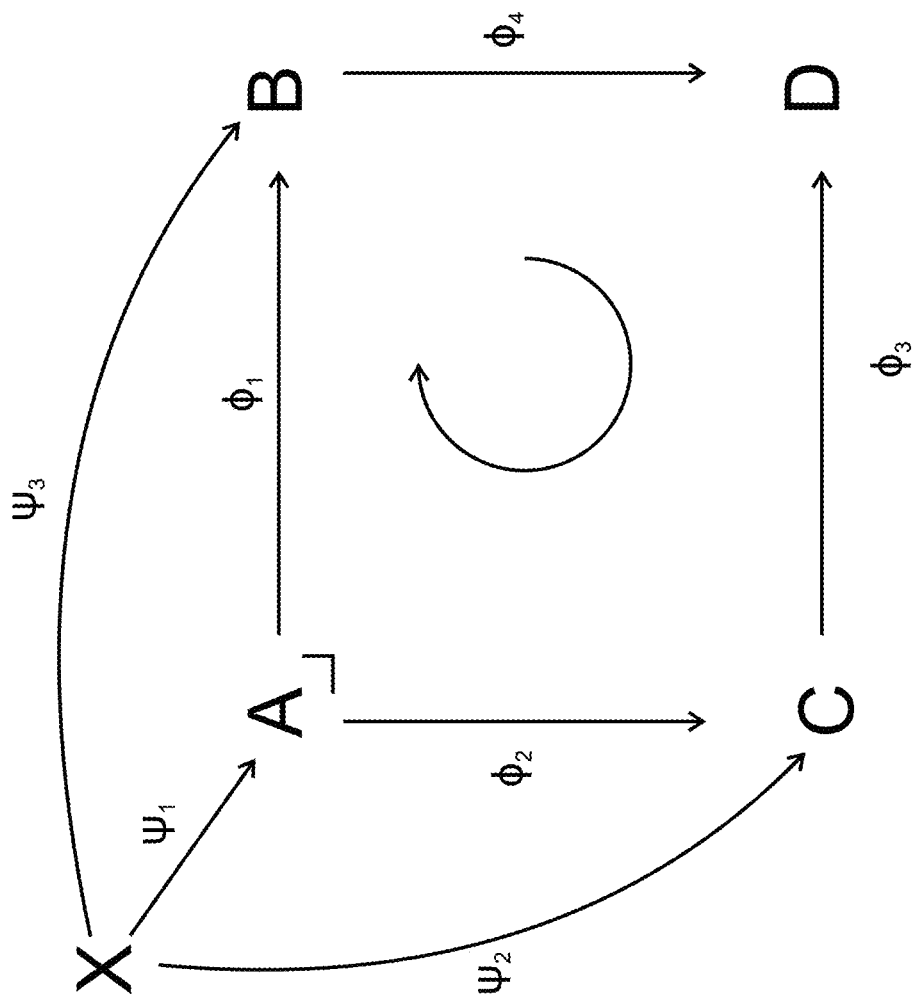
FIG. 20: an example of using the categorical construct "pullback" to define a concept for the system to act upon

FIG. 20 shows an example of using the categorical construct "pullback" to define a concept for the system 1 to choose possible allowed transformations (categorial object A is the pullback of C→D←B, i.e., C×$_D$B, which is denoted by the small ⌐ placed to the lower right of A):

Categorical object X represents "an anatomical sub-structure in the form of a dental implant cannot be moved".
Categorical object A represents "an anatomical sub-structure that cannot be moved".
Categorical object B represents "an anatomical sub-structure in the form of a dental implant".
Categorical object C represents "an anatomical sub-structure".
Categorical object D represents "an implant".
Functor $\phi_1$ represents "has as discernible shape".
Functor $\phi_2$ represents "is".
Functor $\phi_3$ represents "has".
Functor $\phi_4$ represents "is".
Functor $\Psi_1$ represents "is an anatomical sub-structure which is".
Functor $\Psi_2$ represents "is".
Functor $\Psi_3$ represents "is".

The diagram formed by categorical objects A, B, C, D is commutative which is denoted by the arrow ↻. In category theory it can be proven that functor $\Psi_1$ is unique. In other words, there is an unambiguous assignment of the object represented by X to the pullback represented by A which, in turn, is connected to categorical objects C, B, D. During processing of the data represented by the digital data record 17 it can be checked by the different computation modules 7, or computational groups 16 of computation modules 7, which represent categorical objects C, B, D, whether any of the data can be interpreted as representing one or more of these categorical objects. In case all of these categorical objects are present in the processed data (i.e., all of the following can be ascertained by processing the data: "an anatomical sub-structure", "an anatomical sub-structure in the form of a dental implant", "an implant") it can be concluded that the nature of the object represented by X is to be respected with the effect that an anatomical sub-structure in the form of a dental implant will not have "movement" as a possible transformation when the system and method calculate the at least one treatment plan.

FIG. 21 shows examples involving unsupervised learning to learn new concepts by using categorical constructs.

Figure 21C:
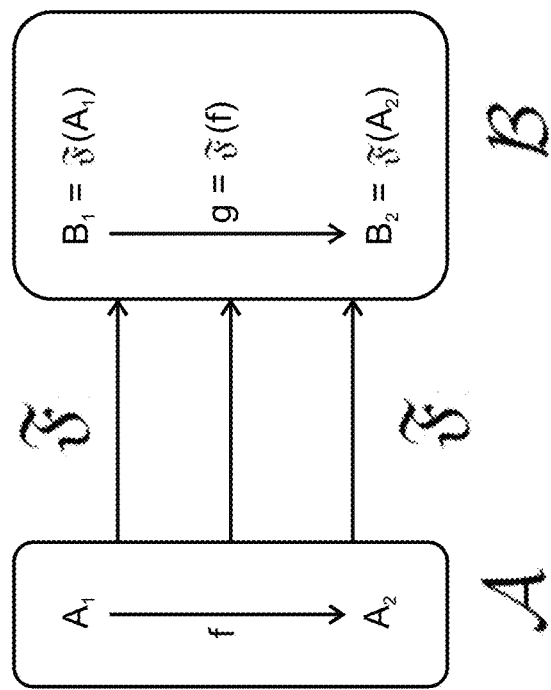
FIG. 21C: an example involving unsupervised learning, kw using categorical constructs
Figure 21A:
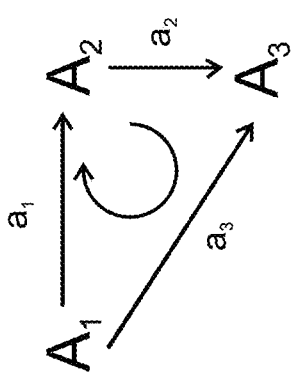
FIG. 21A: an example involving unsupervised learning by using categorical constructs

By way of example, FIG. 21A shows a commutative diagram (as denoted by ↻). If $A_1$ represents the object "molar", $A_2$ represents "a cavity", $A_3$ represents "a dental filling", $a_1$ represents "has" and $a_2$ represents "is filled by", then the system can learn the concept that "molar" has "a dental filling" because $a_2 \circ a_1 = a_3$ gives: "A cavity is filled by a dental filling"∘"Molar has a cavity"="Molar has a dental filling.", i.e., $a_3$="has".

Figure 21B:
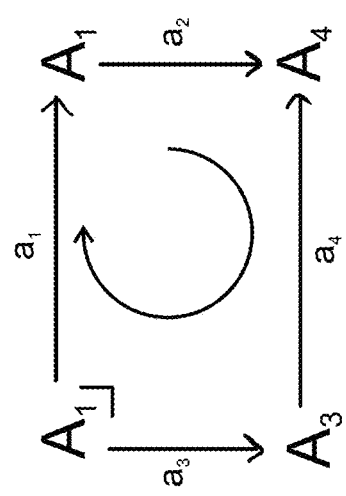
FIG. 21B: an example involving unsupervised learning by using categorical constructs

The example of FIG. 21B shows an analysis of natural language using the categorical construct of a pullback (as denoted by ⌐) where the knowledge of "molar has dental filling" and "incisor has dental filling", represented by the commutative diagram shown (categorical objects $A_2$, $A_3$, $A_4$ represent "molar", "incisor" and "dental filling", respectively, and the morphisms $a_2$, $a_4$ represent "has"), has as pullback $A_1$ "incisor and molar have dental fillings" (morphisms $a_1$ and $a_3$ are projections) which can then be abstracted, e.g., to "anatomical sub-structures". Upon checking by the system 1 involving a human operator or an external database, this generalization would be found to be incorrect because not all anatomical sub-structures can have dental fillings (e.g., gingiva cannot have a dental filling) and the connections between computation modules 7 would have to be retrained.

It is known in category theory that pullbacks can be added by joining the commutative diagrams representing them.

Suppose that, in the example of FIG. 21C, $\mathcal{A}$ represents the category of "incisors" and category $\mathcal{B}$ represents the category of "molars" such that $A_1$, $A_2$ are two incisors which are connected to each other by a rotation represented by morphism f and $B_1$, $B_2$ are two molars. In other words, the system 1 has learned that an incisor which has been rotated is still the same incisor. Using functor $\mathfrak{F}$ ($\mathfrak{F}$: $A_1 \to B_1$, $A_2 \to B_2$, f→g) this concept can be mapped to the category $\mathcal{B}$ of "molars" meaning it is not necessary for the system 1 to re-learn the concept of "rotation of an anatomical sub-structure" as represented by g in the category of "molars".

Figure 22B:
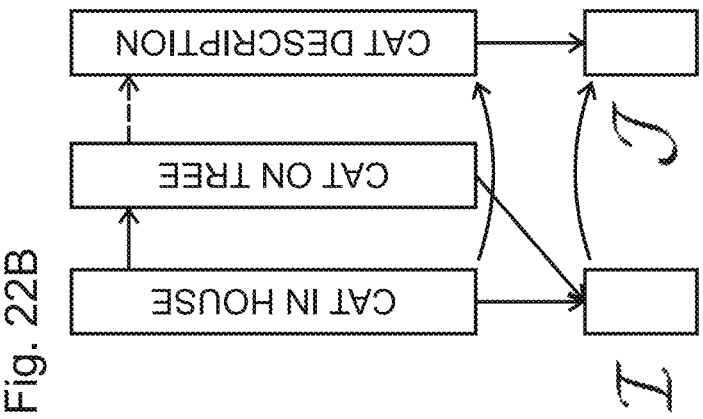
FIG. 22B: an example involving analysis of a combination of data types
Figure 22A:
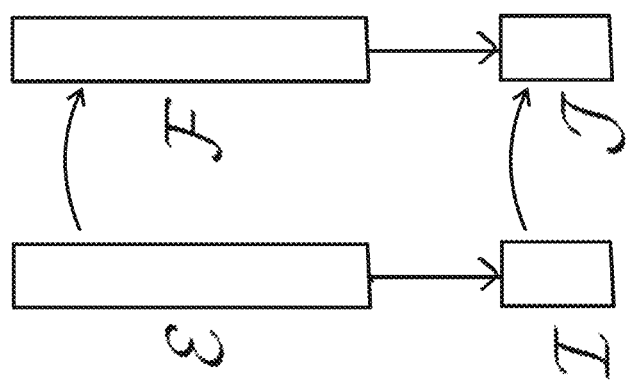
FIG. 22A: an example involving analysis of a combination of data types

FIG. 22A shows an example involving analysis of a combination of data types in the form of anatomical sub-structures in a digital data record 17 which are provided with specific descriptions given in natural language. Another example, involving the same data type, would be the combination of images. The depiction of FIG. 22 relates to an information-point-of-view. Two fibered categories, ε, with base category $\mathcal{I}$, and $\mathcal{F}$, with base category $\mathcal{J}$, are, used to represent an image (e.g., a tooth being shown in an STL-file) and a description given in natural language (e.g., tooth has a dental filling, tooth has caries, tooth has been replaced by a dental implant, ... ) and relating to the image of the tooth in isolation (this can be done, e.g., try teaching a computation module 7 or a plurality of computation modules 7 to recognize teeth), i.e., irrespective of the fact that in one image the tooth is located in an STL-file and in another image it is located in an X-ray image, respectively. Both, the image and the description have, for themselves, unique identifiers, e.g., in the form of keys or addresses or, as shown, of base categories. The system 1 and method can be trained to learn that a certain description is specific to a certain image such that, in this sense, they belong together. This fact can be learned by functors between the index categories $\mathcal{I}$ and $\mathcal{F}$.

FIG. 22B shows an example where it is important that one and the same description has to be specific to different images. For human beings it is intuitively clear that, e.g., a specific tooth shown in an STL-file and in an X-ray file (and/or shown in different orientations), is always the same tooth. For the neuronal networks 71 that are used to cognitively analyze information in the computation modules 7 this is per se not clear and must be taught in a supervised or unsupervised way. Once the system 1 has learned that a tooth shown in different images (or different orientations) is still the same object, it can learn in an unsupervised way (without the need for a random signal, using only commutativity) that the same description is to be associated to two different images, wherein one of the images shows the tooth in an STL-file (and/or in a first orientation) and the other image shows the same tooth in an X-ray image (and/or in a second orientation). This is shown by having both categories "tooth 41 in STL" and "tooth 41 in X-ray" point to the same base category $\mathcal{I}$. The dashed arrow shows the unsupervisedly learned connection between "tooth 41 in STL" and the category "tooth 41-description". Therefore, the system 1 in some embodiments, is configured to attribute the same natural language description to parts of different images showing the same object.

Figure 23:
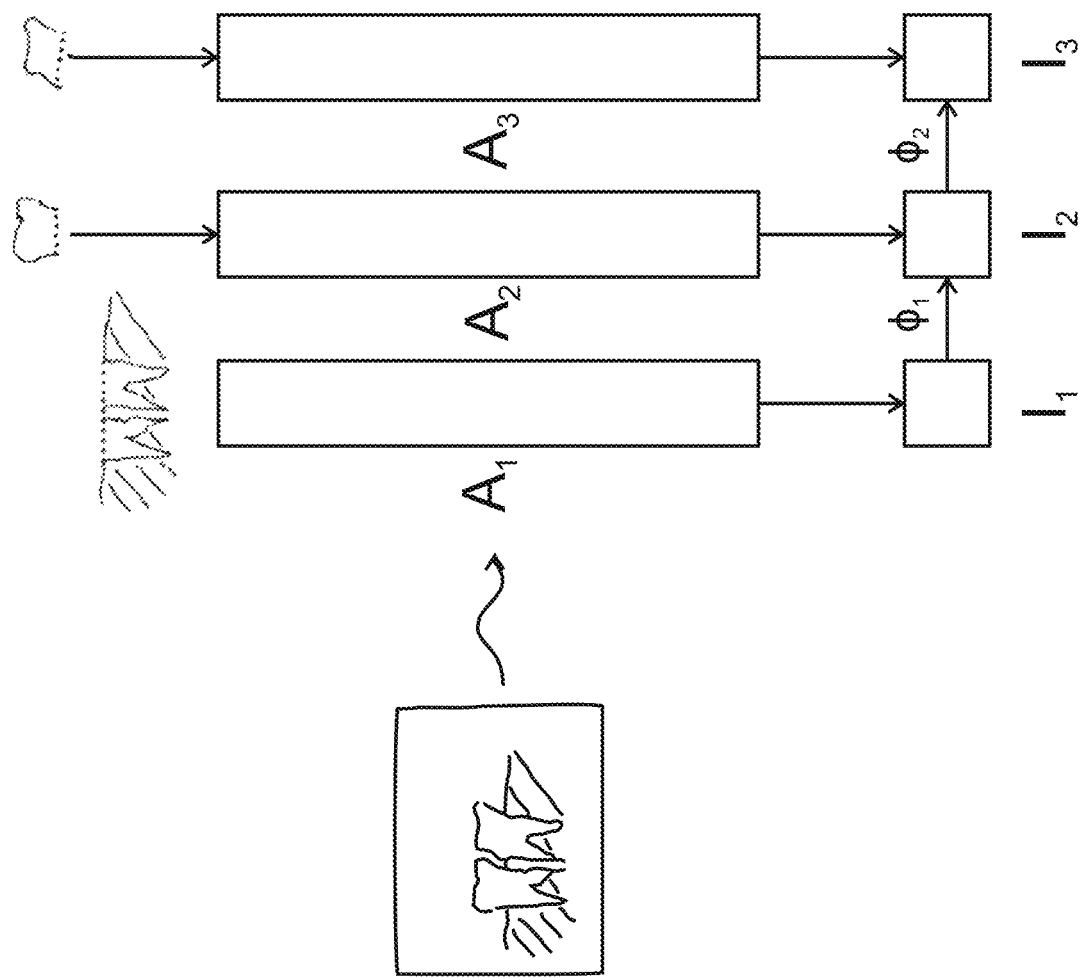
FIG. 23: an example how the system can create a sense of orientation in space and/or time

In FIG. 23 an X-ray image is showing teeth having invisible and visible parts, the invisible parts being embedded in gingiva and the parts protruding from gingiva. The system 1 analyses the image and extracts the different objects, i.e., "gingiva", "invisible parts of teeth" and "visible parts of teeth". The spatial relationships between these objects are encoded by non-commuting functors $\phi_1$, $\phi_2$ between the base categories $I_1$, $I_2$, $I_3$, $I_4$ of the categories $A_1$, $A_2$, $A_3$, G. They are non-commuting because, e.g., the visible parts of the teeth protrude from the gingiva but not the invisible parts. Therefore, in the example of FIG. 23, the more to the right a category is, the higher the anatomical sub-structure represented by that category is arranged in the image. It should be noted that in the same way temporal relationships between objects can be encoded (e.g., replace "higher" by "later").

In this example it can be seen that a base category can itself be a fibered category having a base category ($I_4$).

FIG. 24A-D shows an example how the system 1 can create a virtual model 8 as an output based on both, a digital data record 17 and a supplemental data record 18.

Figure 24A:
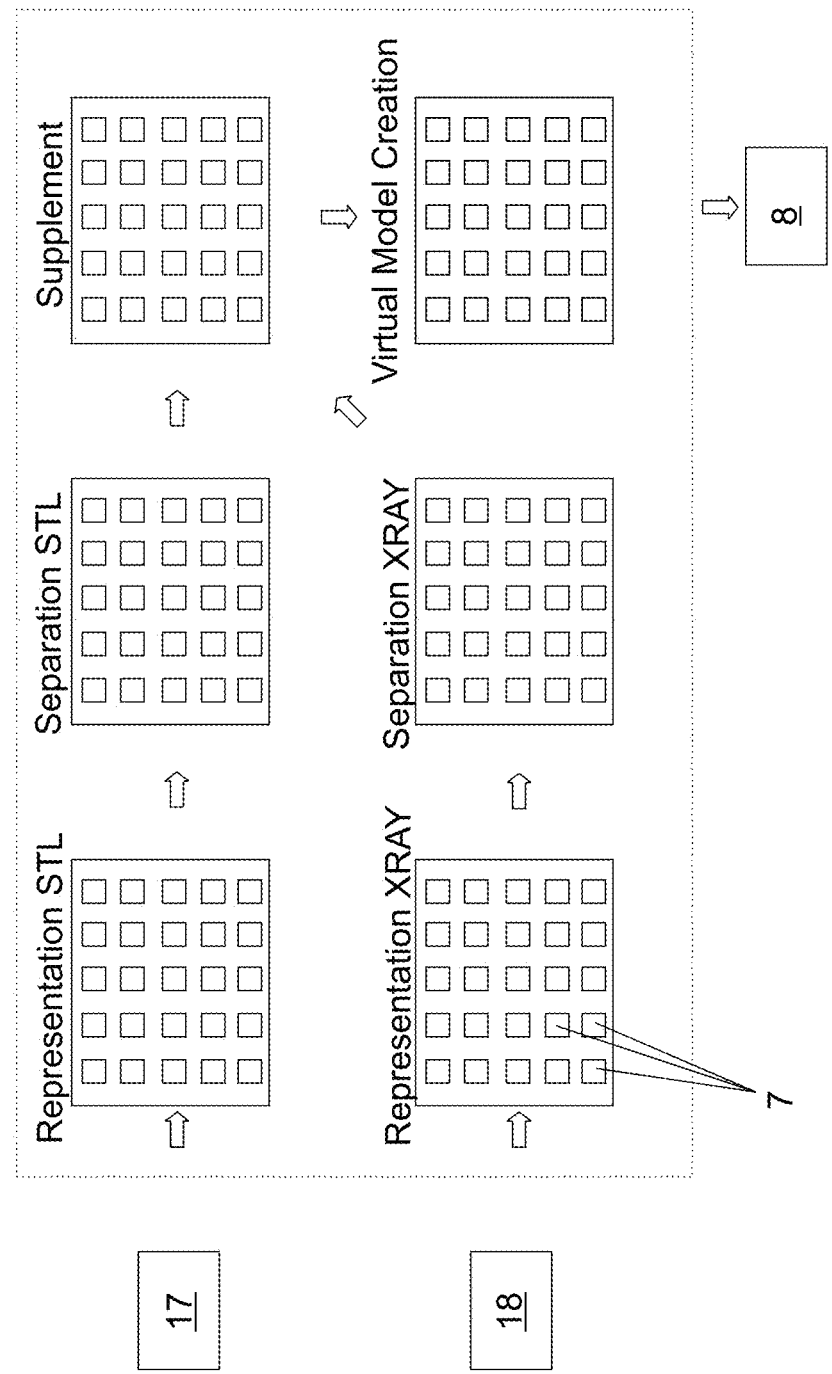
FIG. 24A: an example how the system creates a virtual model and two treatment plans

FIG. 24A shows different groups of computation modules 7 (the small box-shaped structures, only three of which have been assigned with a reference sign in order not to overload the presentation of this Figure) which are configured to accomplish different task in a system 1 according to the invention. It is to be understood that this presentation is highly schematical in the sense that computation modules 7 of a specific group will in reality, i.e., as configured in a computing device 5, not be arranged adjacent to another in any meaningful sense, in other words, the division of computation modules 7 into groups is to be understood symbolically in the sense that those computation modules 7 are shown grouped together which are configured to work on similar tasks. Also, none of the connections between different computation modules 7 and between computation modules 7 and other structures of the system 1 such as the shared memory device 4 are shown. The arrows shown represent flow of information between different groups of computation modules 7.

The group marked "REPRESENTATION STL" is configured to represent different anatomical sub-structures that might appear in an STL-representation of a human's dentition such as different teeth and gingiva. The group marked "REPRESENTATION XRAY" is configured to represent different anatomical sub-structures that might appear in an X-ray-representation of a human's dentition such as different teeth and gingiva.

The group marked "SEPARATION STL" is configured to accomplish separation of the visible parts of teeth and gingiva in an STL-representation of a human's dentition. The group marked "SEPARATION XRAY" is configured to accomplish separation of (both, visible and invisible parts of) teeth and gingiva.

The group marked "SUPPLEMENT" is configured to supplement the information gained from the STL-representation with the information from the X-ray-representation forming a (unified) supplemented data record which, in this embodiment, is used by the group marked "VIRTUAL MODEL CREATION" to create the virtual model. Alternatively, it would be possible to directly use the supplemental information in the creation of the virtual model 8, i.e., without forming a supplemented data record.

Figure 24B:
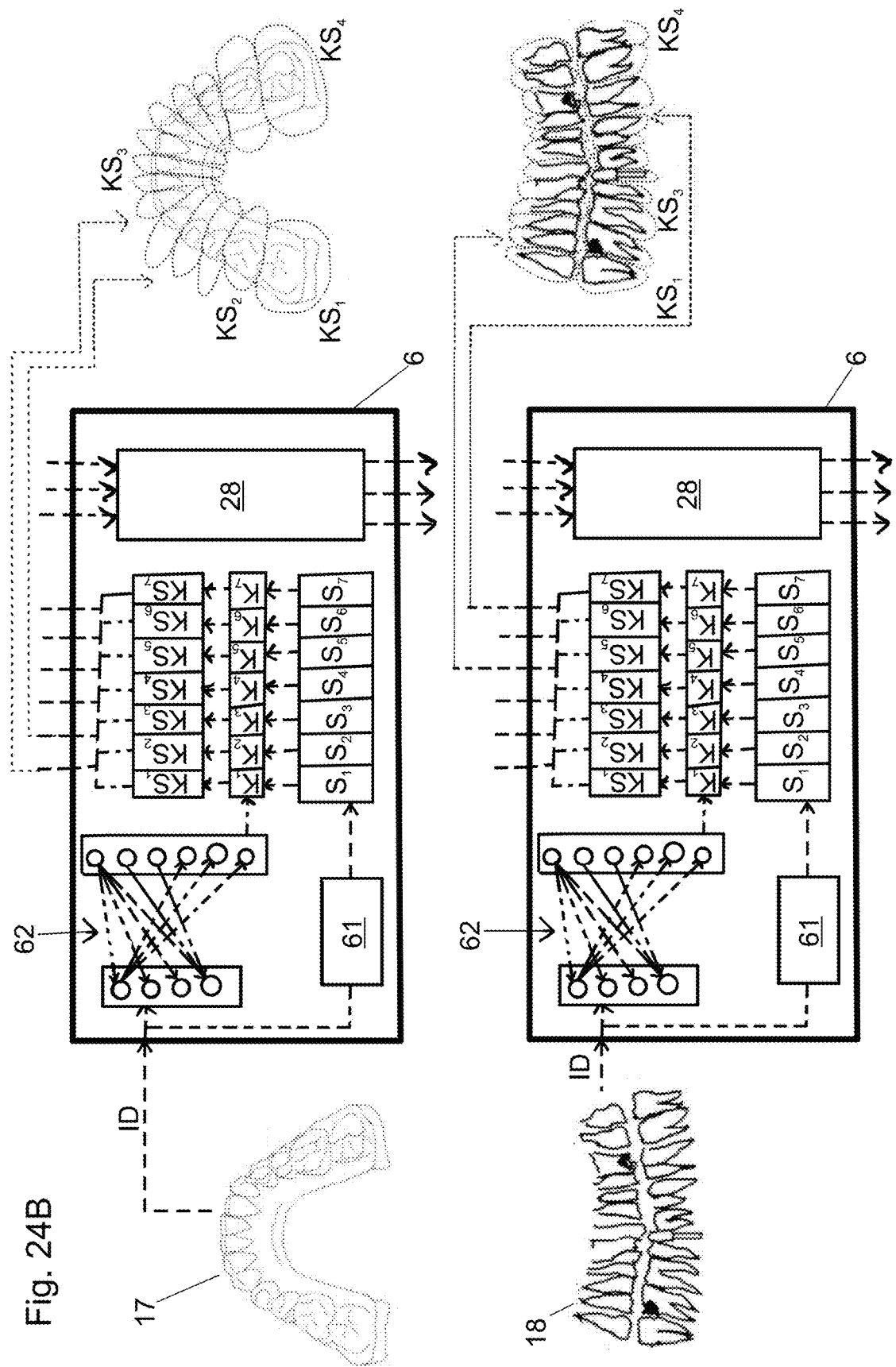
FIG. 24B: an example how the system creates a virtual model and two treatment plans

FIG. 24B shows an optional segmentation of the data contained in the digital data record 17 and the supplemental data record 18 into keyed data segments $KS_i$ using a data hub process 6 as explained with respect to FIG. 5. With respect to the STL-representation each keyed data segment $KS_i$ represents a single tooth together with the surrounding gingiva, i.e., in this embodiment segmentation has been chosen such that the visible parts of the teeth are separated from each other. Other ways of creating keyed data segments are of course possible. With respect to the X-ray-representation each keyed data segment $KS_i$ represents the visible and the invisible parts of a single tooth, in an X-ray-representation the gingiva is less represented due to the nature of X-ray-imagery. If data segmentation as shown in this Figure is present in an embodiment it would be done before the step shown in FIG. 24C.

FIG. 24C shows for some of the keyed data segments $KS_i$ from the STL-representation how they are processed. The computation modules repeatedly check whether a keyed data segment $KS_i$ with a module-specific key is present (this is shown in FIG. 24C by an arrow going from a computation module 7 to a keyed data segment $KS_i$) this process is shown for only a few of the computation modules 7). If this is the case the corresponding keyed data segment $KS_i$ is loaded into the computation module 7 (this is shown in FIG. 24C by an arrow going from a keyed data segment $KS_i$ to a computation module 7), if this is not the case, a keyed data segment $KS_i$ is not loaded by a computation module 7

(although there is an arrow going from a computation module 7 to a keyed data segment KS$_i$, there is no arrow from that keyed data segment KS$_i$ back to the computation module 7). The task of the computation modules 7 in this group is to recognize those teeth which they are configured to represent (this is shown in the form "TOOTH No. . . .") and to output this information to other structures of the system 1 such as other computation modules 7 or the shared memory device 4.

Figure 24D:
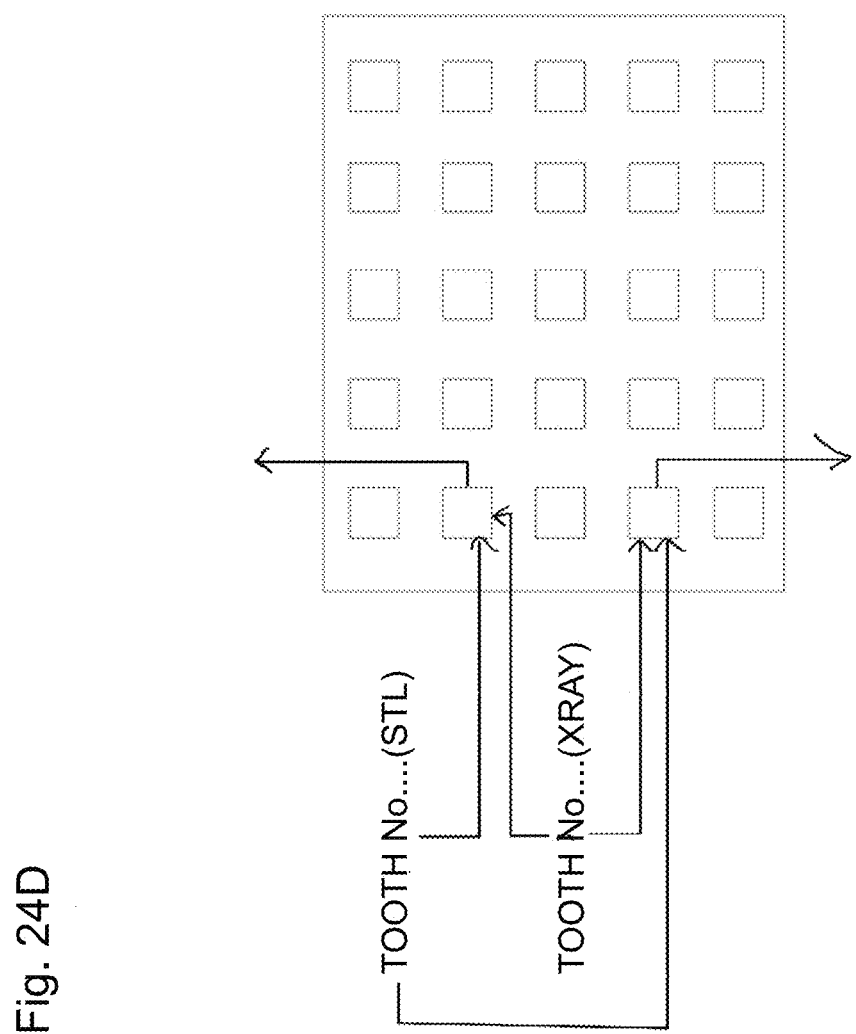
FIG. 24D: an example low the system creates a virtual model and two treatment plans

The computation nodules 7 shown in FIG. 24D use the information obtained from the STL-representation and the X-ray-representation to create a supplemented data record 18.

Figure 24E:
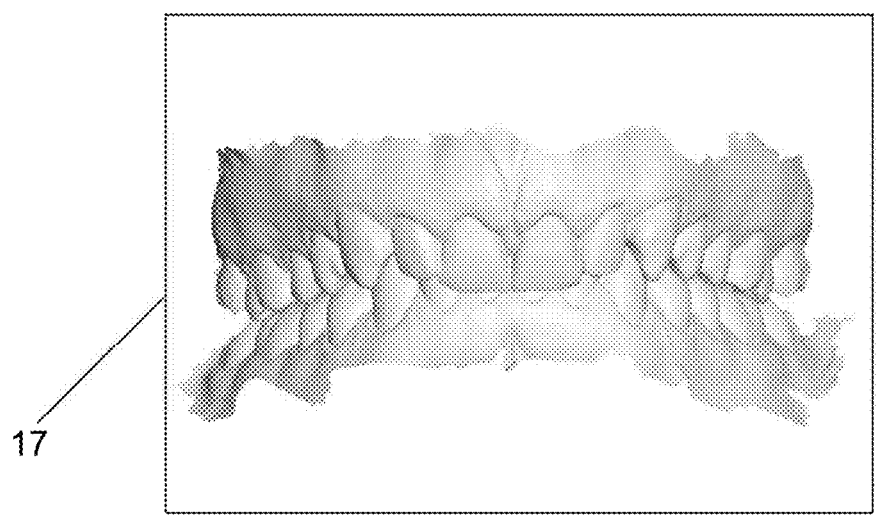
FIG. 24E: an example how the system creates a virtual model and two treatment plans
Figure 24F:
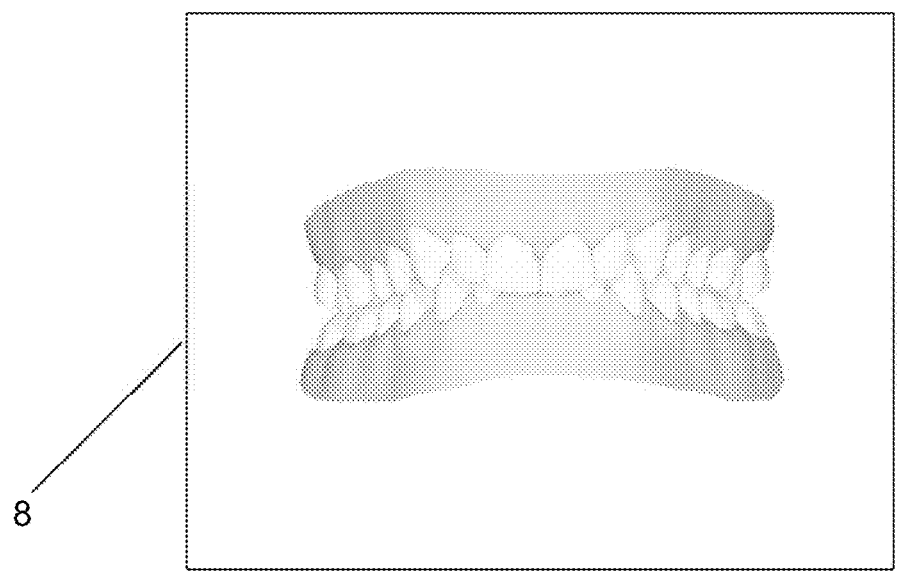
FIG. 24F: an example how the system creates a virtual model and two treatment plans

FIGS. 24E and 24F show a comparison between the 3d model 17 provided as an input to the system 1 and the virtual model 8 created by the system 1 for the same angular view. Of course, both, the 3d model 17 and the virtual model 8 can be rotated through an angular field of 360 degrees and only a single angular view is shown. In the virtual model 8 all teeth have been separated from each other and from the gingiva. The roots of the teeth that are shown in FIG. 24F need not be the actual roots of the teeth but can be templates that can be used to represent roots. Of course, as already explained elsewhere in this disclosure, supplemental information could have been used to create actual representations of the roots and to show them in the virtual model 8.

Figure 24G:
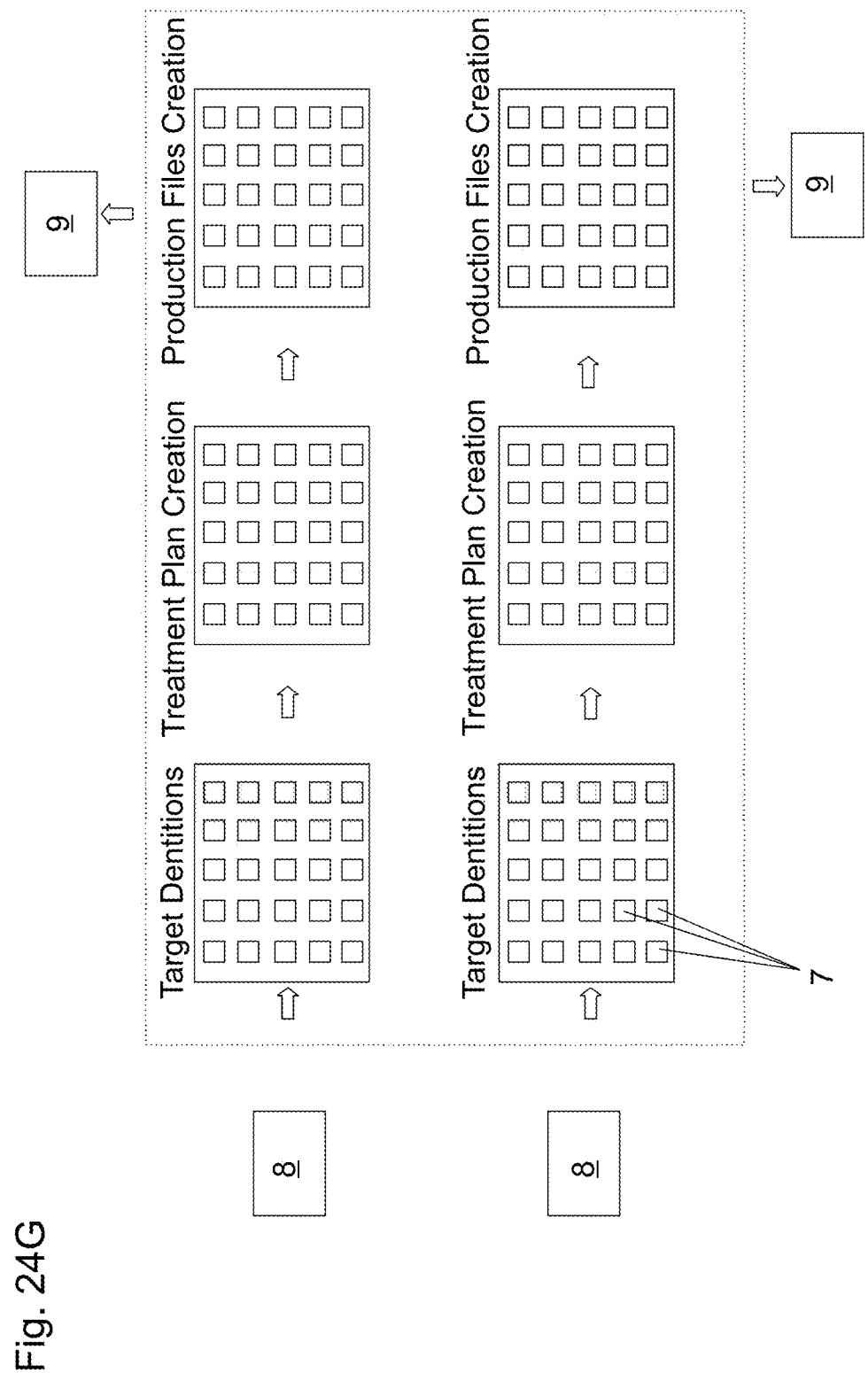
FIG. 24G: an example how the system creates a virtual model and two treatment plans

FIG. 24G shows how in this embodiment two, different treatment plans 9 can be created by the system 1 in parallel. The different treatment plans 9 can differ from each other due to different transformations (different sequence of intermediary dentitions, e.g., different number of steps and/or different movement of teeth) and/or due to different target dentitions. As the upper block of groups of computation modules 7 and the lower block work independently from each other, only one of them will be described in the following:

Based on a virtual model 8 which is used as an input the system 1 identifies malocclusions present in the dentition represented by the virtual model 8 by comparing the dentition of the virtual model 8 (starting dentition) with a catalog of target dentitions (having no or only acceptable malocclusions) represented by the group of computation models 7 named "TARGET DENTITIONS". The group of computation models 7 named "TREATMENT PLAN CREATION" then determines intermediary dentitions forming a sequence of dentitions from the starting dentition to the target dentition wherein the dentitions of the sequence are connected by the transformations necessary to transform the starting dentition into the target dentition. In this embodiment a group of computation modules 7 named "PRODUCTION FILES CREATION" creates binary files that can directly be used by a manufacturing device to produce the appliances necessary for the transformations of the treatment plan 9.

Figure 31A:
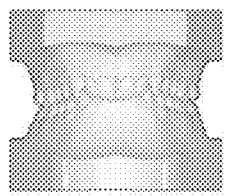
FIG. 31A: an example of digital representations to create deep drawing tools for deep drawing of aligners
Figure 31B:
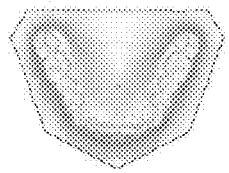
FIG. 31B: an example of digital representations to create deep drawing tools for deep drawing of aligners
Figure 32A:
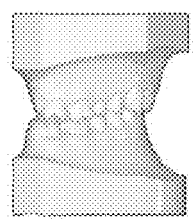
FIG. 32A: an example of digital representations to create deep drawing tools for deep drawing of aligners
Figure 32B:
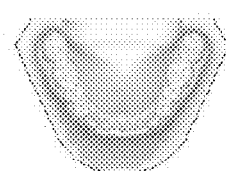
FIG. 32B: an example of digital representations to create deep drawing tools for deep drawing of aligners
Figure 33A:
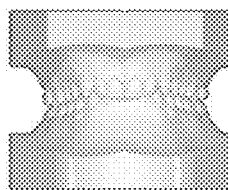
FIG. 33A: an example of digital representations to create deep drawing tools for deep drawing of aligners
Figure 33B:
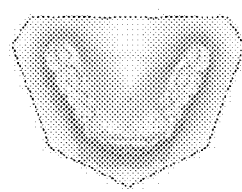
FIG. 33B: an example of digital representations to create deep drawing tools for deep drawing of aligners
Figure 34A:
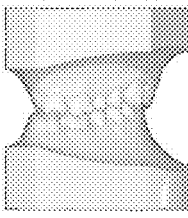
FIG. 34A: an example of digital representations to create deep drawing tools for deep drawing of aligners
Figure 34B:
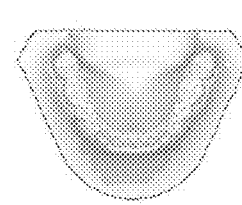
FIG. 34B: an example of digital representations to create deep drawing tools for deep drawing of aligners
Figure 35A:
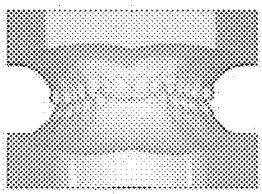
FIG. 35A: an example of digital representations to create deep drawing tools for deep drawing of aligners
Figure 35B:
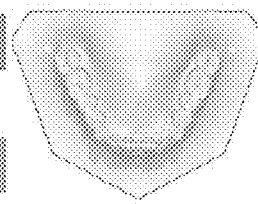
FIG. 35B: an example of digital representations to create deep drawing tools for deep drawing of aligners
Figure 36A:
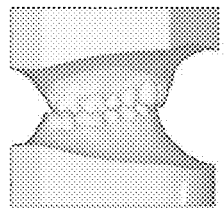
FIG. 36A: an example of digital representations to create deep drawing tools for deep drawing of aligners
Figure 36B:
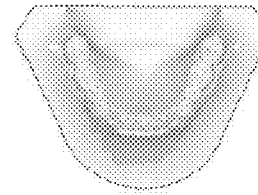
FIG. 36B: an example of digital representations to create deep drawing tools for deep drawing of aligners
Figure 52:
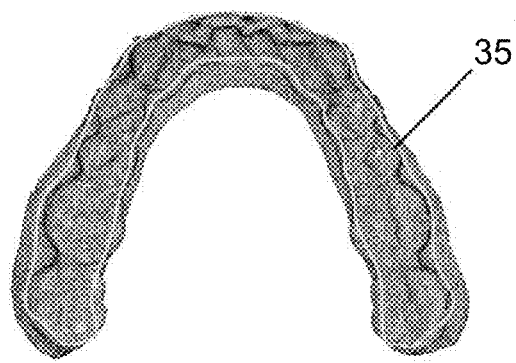
FIGS. 52 and 53A, 53B: examples of a virtual model of an appliance created fry the system in the form of an aligner

The series of FIGS. 25 to 40 shows different examples of digital representations of deep drawing tools (base trays) created by the system 1 which can be used for deep drawing of aligners 36. FIGS. 25 and 26 show a first example in different views for a small base tray used in the European Union, FIGS. 27 and 28 show a standard size for a base tray used in the European Union and FIGS. 29 and 30 show a large base tray used in the European Union. FIGS. 31 and 32 show small base trays used in the United States, FIGS. 33 and 34 show standard size base trays used in the United States and FIGS. 35 and 36 show large base trays used in the United States. FIGS. 37 and 38 show a horseshoe shaped base tray and FIGS. 39 and 40 show a plate base tray. The user can choose which type is to be outputted by the system 1. The system also calculates a cutline 35 (this is exemplary shawl for the deep drawn aligner 36 depicted in FIG. 52) to indicate how an aligner 36 is to be cut.

Figure 53A:
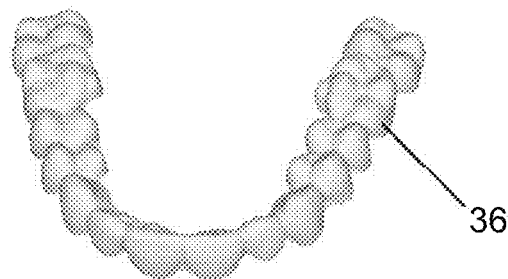
Figure 53B:
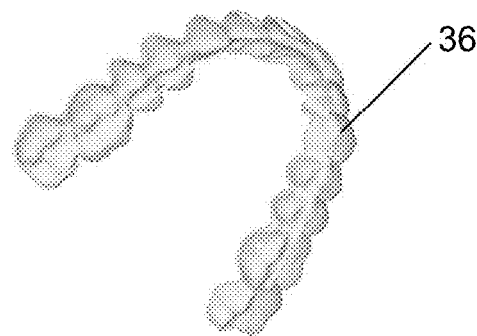

One of the alternative ways of producing an aligner 36 is 3d printing. FIG. 53 shows a virtual model created by the system 1 which can be used to 3d print the aligner 36.

Figure 41:
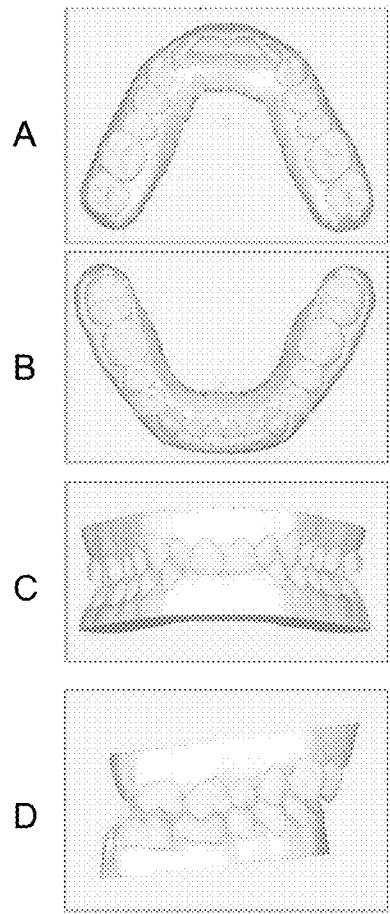
Figure 42:
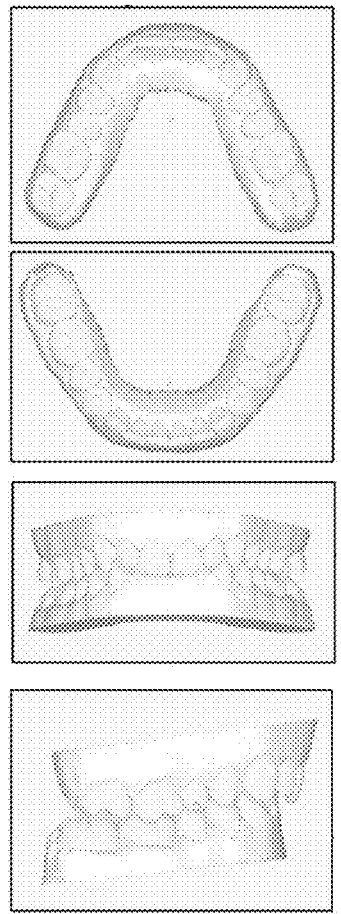
Figure 43:
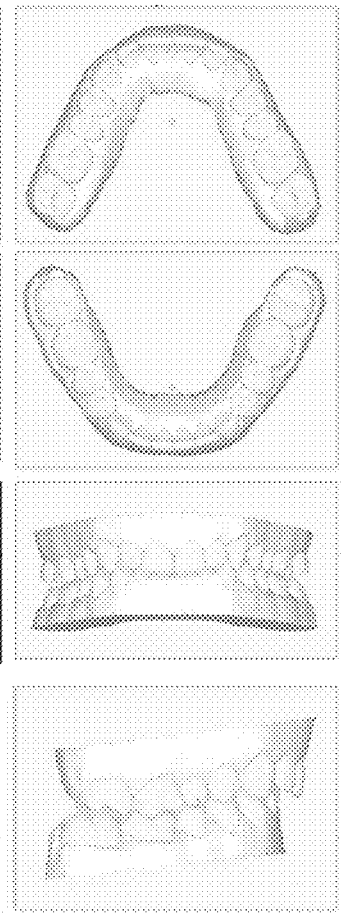

FIGS. 41 to 43 show (for different views marked as A, B, C, D) three virtual models 8 of dentitions created by the system 1 as described above. The dentition shown in FIG. 41 is the starting dentition (step 00), the dentition shown in FIG. 42 is an intermediary dentition (here step 06 has been chosen) and the dentition shown in FIG. 43 is the target dentition (step 12). The use of twelve steps in the treatment plan 9 is exemplary only, a different number of steps can be chosen (cf. the example of FIGS. 46 to 48 were sixteen steps were chosen, in this example it is also shown that the system 1 can take into account the placement of tooth attachments 37 on some of the teeth and move them together with the teeth they are placed on).

The totality of intermediary dentitions together with the target dentition forms the treatment plan 9 because the virtual models 8 representing those dentitions contain all information required to produce the appliances necessary to move the teeth according to the transformations defined by the sequence of dentitions and it is possible for a human operator to study the suggested transformation, either via the ASCII files (here CSV files) and/or via the sequence of virtual models 8 representing the dentitions.

Figure 45:
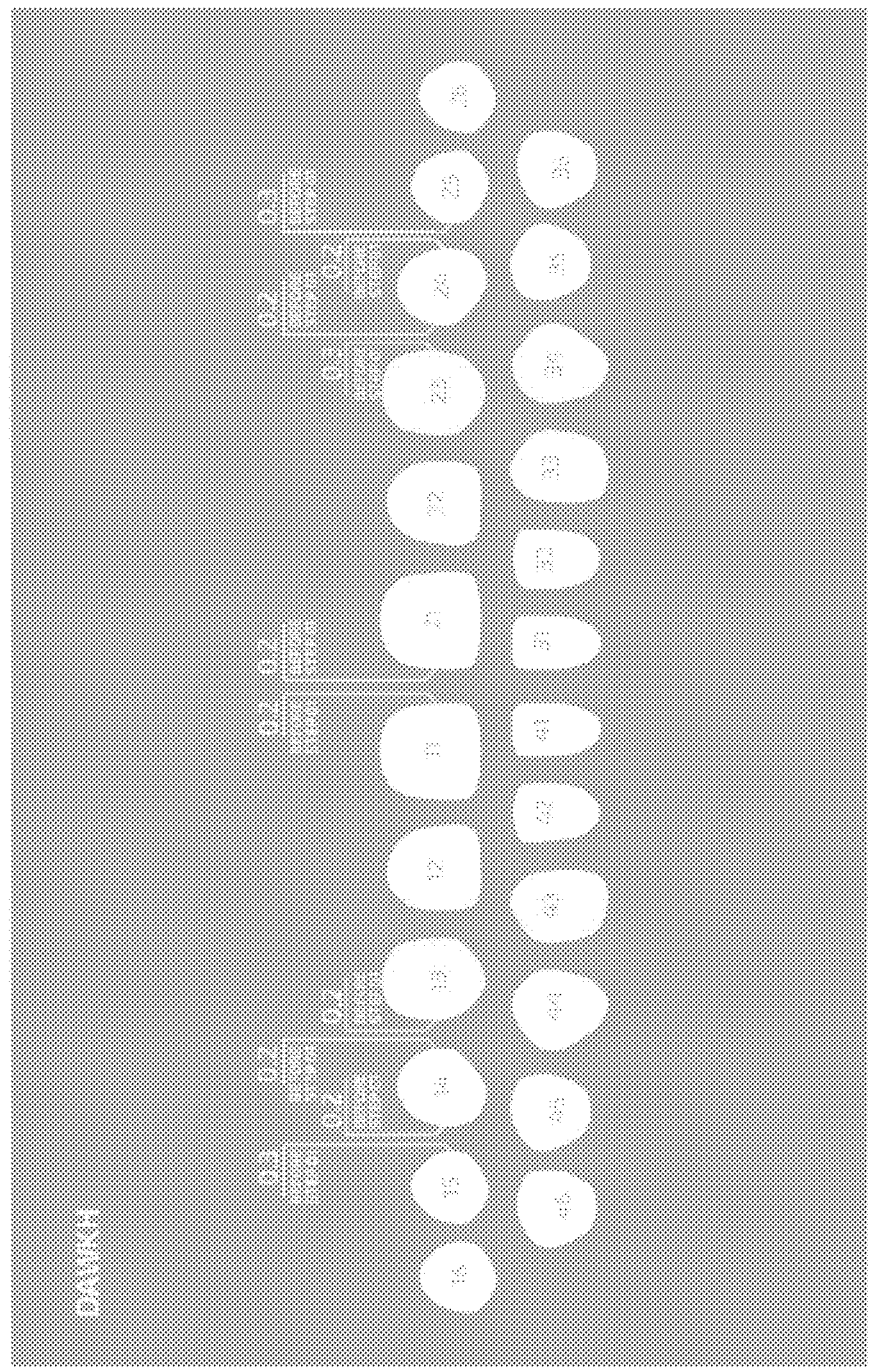

FIGS. 44A and 45 (using dental notation according to ISO 3950) show a detail of the treatment plan 9 of FIGS. 41 to 43 in two different ways of presenting the same information. The detail concerns the necessity of doing an interproximal reduction with respect to some of the teeth of the starting dentition before these teeth can be shifted and/or rotated (therefore, the interproximal reduction is marked as being before step 01). FIG. 44A shows a presentation of this information by way of a CSV file created by the system 1 while in FIG. 45 a pictorial way of presentation has been chosen.

FIGS. 44B to 44M show out put created by the system 1 in the form of ASCII files (here: CSV files) detailing movement of teeth according to the treatment plan 9 for the example of FIGS. 41 to 43 (using dental notation according to ISO 3950):

FIG. 44 B shows the transformations of step 1, FIG. 44C shows the transformations of step 2, . . . , FIG. 44M shows the transformations of step 12. FIG. 44N shows the total movements of the teeth from the starting dentition to the target dentition. The CSV file of FIG. 44A together with the CSV files of FIG. 44B to 44M form a complete treatment plan 9 (the information of FIG. 44N regarding total movement of teeth can be derived from the information of FIGS. 44B to 44M) because they contain all information required to produce the appliances necessary to move the teeth according to the transformations defined by the CSV files.

The numerical values of the transformations shown in ASCII files can be derived by the system 1 based on the virtual models 8 of the sequence of intermediary dentitions to the target dentition for any given starting dentition by comparing subsequent dentitions and determining what configurational changes—if any—each of the teeth has undergone between subsequent dentitions. Alternatively, the system 1 could compare only the starting dentition and the target dentition, determine what configurational changes—if any—each of the teeth has undergone from the starting dentition to the target dentition in total, and, based on this information, divide the total configurational changes into a sequence of configurational changes according to a (possibly pre-determined) number of steps and create virtual models 8 for the intermediate dentitions according to the sequence of configurational changes.

In the example of FIGS. 49 to 51, which show three virtual models 8 of dentitions created by the system 1 as described above (FIG. 49: starting dentition—step 00, FIG. 50: intermediary dentition—step 06, FIG. 51: target dentition—step 12), it can be seen that a gap between adjacent teeth can be filled by a virtual placeholder 34 and be taken into account by the system 1 during creation of a treatment plan 9. This virtual placeholder 34 could be provided by an operator of the system 1 or could be chosen by the system 1 itself.

Figure 54A:
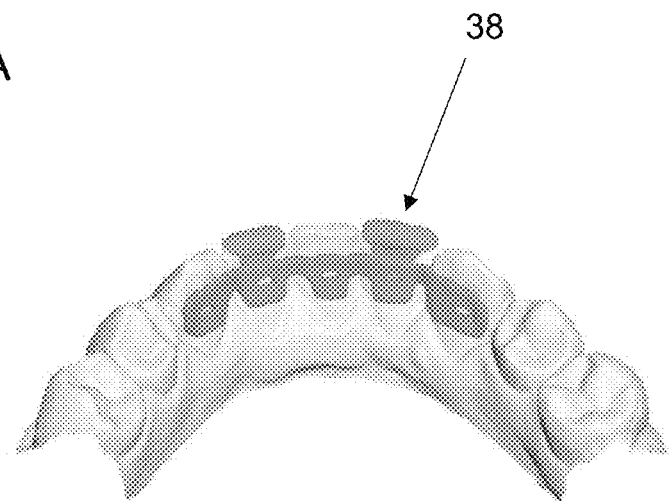
FIG. 54A: an example of a virtual model of appliance created by the system in the form of a fixed lingual retainer
Figure 54B:
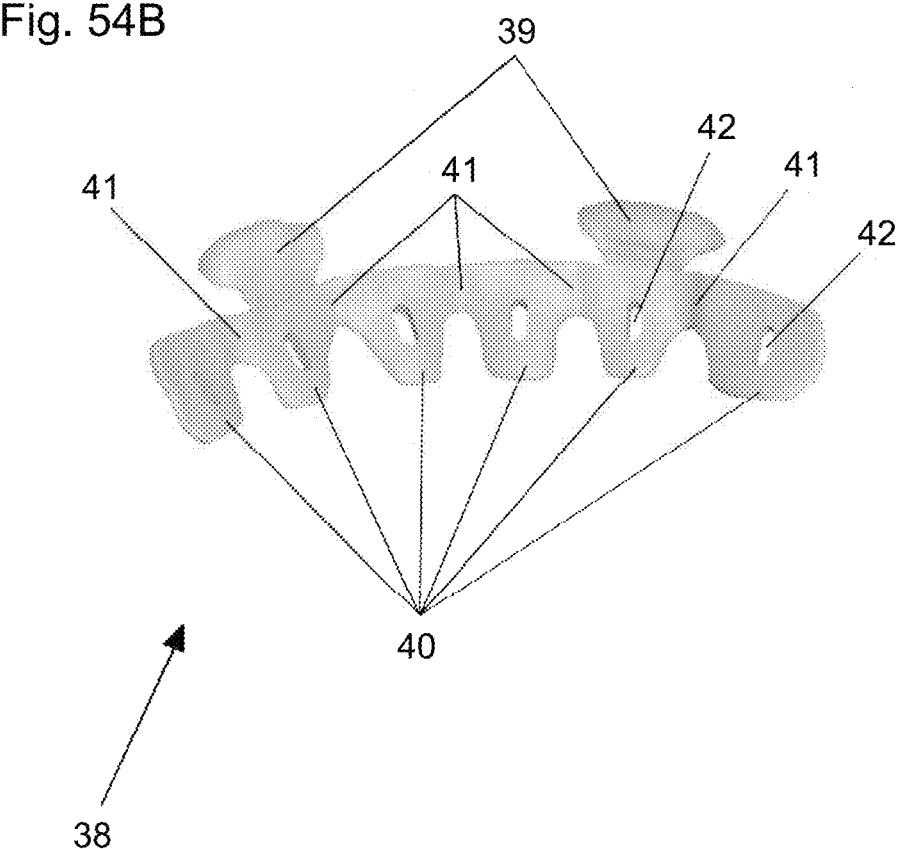
FIG. 54B: an example of a virtual model of an appliance created by the system in the form of a fixed lingual retainer

FIGS. 54A and 54B show an example of a virtual model 8 of an appliance in the form of a fixed lingual retainer 38 created by the system 1. Such a fixed lingual retainer 38 is intended for use after the target dentition has been reached in a treatment plan 9 and is meant to keep the teeth in the positions defined by the target dentition. Although only shown with respect to the mandible, alternatively or in addition, a fixed lingual retainer 38 could also be provided with respect to the maxilla. Instead of a one-piece fixed lingual retainer 38 a two-piece fixed lingual retainer 38 to be arranged on each side of the median palatine suture could be used.

The virtual model 8 of the fixed lingual retainer 38 comprises placement portions 39 to be placed on the top edge of selected teeth (in the example two placement portions 39 are present, the number could be chosen differently). Tooth adhering portions 40 each have a generally fiat to edge and a generally curved bottom edge and are designed to exactly match the shape of the lingual side of the teeth they are placed on. Connection portions 41 are located at a position below the top edge of the tooth-adhering portions 40 and are formed narrower than the tooth-adhering portions 40 to expose as much tooth surface as possible between the tooth-adhering portions. Holes 42 allow the application of a dental adhesive to affix the fixed lingual retainer 38 via bonding surfaces of the tooth-adhering portions 40 to the teeth.

Figure 55A:
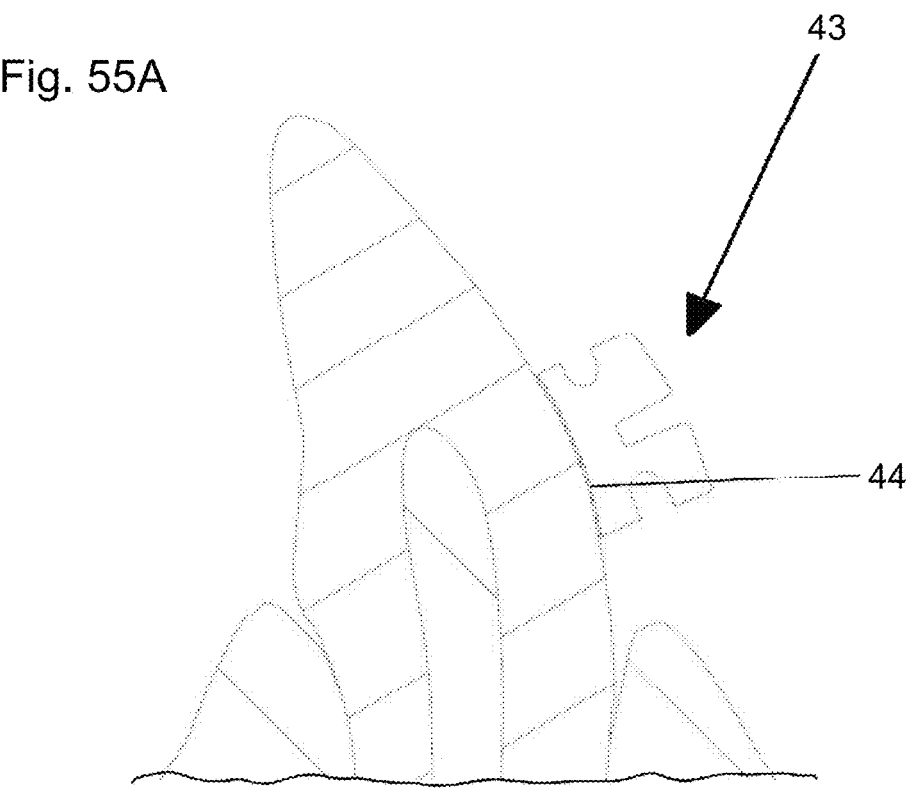
FIG. 55A: an example of a virtual model of appliance created by the system in the form of an orthodontic bracket
Figure 55B:
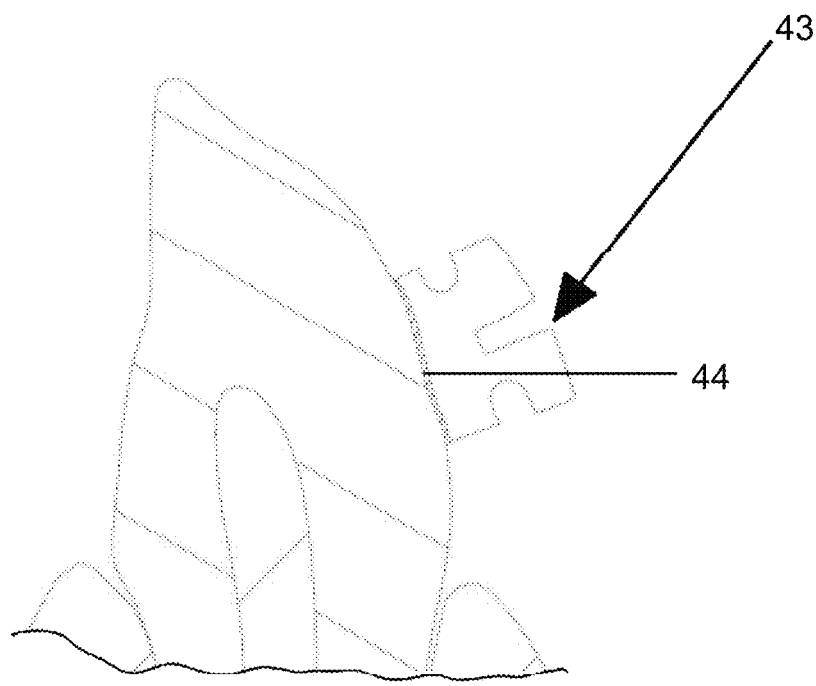
FIG. 55B: an example of a virtual model of an appliance created by the system in the form of an orthodontic bracket It should be noted that the number of components present in the Figures is to be understood exemplary and not limiting. In particular with respect to the computation modules 7 it is to be assumed that in reality there will be many more instantiations than shown in the Figures. Dashed lines show at least some of the interactions between components of the system 1 but, possibly, not all of the interactions. It should also be noted that graphical representations of entities such as computation modules 7 or images of anatomical sub-structures shown in conjunction with such entities (e.g., teeth) are drawn for better understanding of the invention but, with respect to the system 1, are entities encoded in computer code and are instantiated during runtime (technical-point-of-view) or in the form of categorical representations (information-point-of-view)

FIGS. 55A and 55B show an example of a virtual model 8 of an appliance in the form of an orthodontic bracket 43 created by the system 1. An orthodontic bracket 43 is placed onto a tooth and is connected to orthodontic brackets on other teeth by way of an archwire (not shown) to move the teeth to a desired dentition (intermediary dentition or target dentition). By using the information of the virtual model 8 of a dentition (starting dentition or intermediary dentition), the system 1 can create a bonding surface 44 of the orthodontic bracket 43 which perfectly matches the surface of the tooth to which it is bonded.

An orthodontic appliance such as a fixed lingual retainer 38 or an orthodontic bracket 43 can be formed of ceramic, composite, or metal and is preferably translucent, opaque or fully transparent ceramic or composite material (e.g., aluminum oxide or zirconium oxide ceramics). It can be manufactured by any known fabrication method based on the virtual model 8 created by the system 1, e.g., CNC milling, injection molding, 3d printing or any kind of additive technology, composite vacuum forming, . . . .

REFERENCE SIGNS LIST

1 system
2 first interface
3 second interface
4 shared memory device
5 computing device
6 data hub process
61 segmentation sub-process
62 keying sub-process
7 computation module
71 neuronal network
8 virtual model
9 treatment plan
10 layer I
11 layer II
12 layer III
13 layer IV
14 layer V
15 layer VI
16 computational group
17 digital data record
18 supplemental data record
19 supplemented data record
20 file
21 artificial neuron
22 integration function
23 activation function
24 synapse of artificial neuron
25 branching of axon of artificial neuron
26 weight storage
27 random signal generator
28 routing process
29 receptor for random signal
30 server
31 client computer
32 communication network
33 scanner
34 virtual placeholder
35 cutline
36 aligner
37 tooth attachment
38 fixed lingual retainer
39 placement portion of retainer
40 tooth-adhering portion of retainer
41 connection portion of retainer
42 hole of retainer
43 orthodontic bracket
44 bonding surface of orthodontic bracket
ID input data
OD output data
$K_i$ ith key
$S_i$ ith data segment
$KS_i$ ith keyed data segment
$L_i$ ith layer of neuronal network
RANDOM random signal $\underset{\longleftarrow}{\lim} C_i$ projective limit
] pullback
◯ commutative diagram

What is claimed:
1. A system for creating a virtual model representing at least part of a dentition of a patient, comprising:
at least one computing device which is configured to execute in parallel a plurality of processes
at least one shared memory device which can be accessed by the at least one computing device at least one first interface for receiving a digital data record representing a 3d representation of at least part of a dentition of a patient and for storing the digital data record in the at least one shared memory device at least one second interface for outputting data wherein the plurality of parallelly executed processes comprises a plurality of groups of computation modules, each computation module being configured to run at least one neuronal network in order to apply a machine learning technique and each group of computation modules comprising one or more computation modules wherein different groups of computation modules represent different anatomical sub-structures that might be present in a dentition of a patient, each anatomical sub-structure being represented in different configurational states, shapes and sizes, the different anatomical sub-structures being at least: visible parts of teeth and gingiva each group of computation modules is configured to apply the machine learning technique on at least part of the digital data record and to output the result to at least one different group of computation modules or to the shared memory device or to the at least one second interface those anatomical sub-structures which are present in the at least part of a dentition represented by the digital data record are identified by those groups of computation modules which represent these anatomical sub-structures and the virtual model is created based on the identified anatomical sub-structures, said virtual model representing at least the visible parts of teeth, the visible parts of teeth being separated from each other and the gingiva and wherein different groups of computation modules represent at least parts of different dentitions which are cataloged as belonging to a catalog of target dentitions different groups of computation modules represent at least parts of different dentitions which are cataloged as belonging to a catalog of starting dentitions different groups of computation modules represent at least parts of different dentitions which are cataloged as belonging to a catalog of intermediary dentitions for each starting dentition and for each target dentition, there are connections, preferably represented by different groups of computation modules, between a starting dentition, different intermediary dentitions and a target dentition, thereby establishing at least one sequence of intermediary dentitions leading from a starting dentition to a target dentition, wherein the plurality of parallelly executed processes further comprises at least one data hub process, the at least one data hub process being connected to the shared memory device or to the at least one first interface and being configured to segment the digital data record into data segments, if the digital data record is not already provided in form of data segments, and to provide each data segment with a key and wherein said computation modules are configured to:

check whether data segments provided with a specific key are present in the at least one shared memory device or are provided by at least one different group of computation modules;

run idly if no data segment with the specific key is detected or provided; and if a data segment with the specific key is detected in the at least one shared memory device or provided by at least one different group of computation modules, apply the machine learning technique on that data segment and output the result to at least one different group of computation modules or to the shared memory device or to the at least one output device.

2. The system according to claim 1, wherein, based on an inputted digital data record representing a (part of a) dentition showing misalignment, the system is configured:

to identify, in the catalog of starting dentitions, at least one dentition which is identical to or at least similar to the (part of a) dentition showing misalignment, and based on the identified at least one starting dentition, to find at least one established sequence of intermediary dentitions in the catalog of intermediary dentitions, such that an endpoint of the sequence of intermediary dentitions is a target dentition in the catalog of target dentitions.

3. The system according to claim 2, wherein the system is configured to determine a set of transformations necessary to transform the (part of a) dentition showing misalignment into the at least one target dentition via at least one of the sequences of intermediary dentitions.

4. The system according to claim 1, wherein:

a set of possible boundary conditions is provided based on the virtual model the system is configured to check whether at least one of the boundary conditions is applicable if at least one of the boundary conditions is applicable, taking account of said at least one boundary condition when determining the sequence of intermediary dentitions.

5. The system according to claim 1, wherein said sequence of intermediary den-titions is used to create at least one treatment plan, wherein the at least one treatment plan is provided in form of:

at least one CAD file, or at least one human-recognizable file.

6. The system according to claim 5, wherein the at least one treatment plan comprises successive or iterative steps for arriving at the target dentition.

7. A computer implemented method for creating a virtual model representing at least part of a dentition of a patient, comprising running at least one computing device which receives a digital data record representing a 3d representation of at least part of a dentition of a patient and stores the digital data record in at least one shared memory device and which executes in parallel a plurality of processes comprising a plurality of groups of computation modules, wherein each computation module runs at least one neuronal network in order to apply a machine learning technique and each group of computation modules comprises one or more computation modules wherein different groups of computation modules represent different anatomical sub-structures that might be present in a dentition of a patient, each anatomical sub-structure being represented in different configurational states, shapes and sizes, the different anatomical sub-structures being at least: visible parts of teeth and gingiva those anatomical sub-structure which are present in the digital data record are identified by those groups of computation modules which represent these anatomical sub-structures and the virtual model is created based on the identified anatomical sub-structures, said virtual model representing at least the visible parts of teeth, the visible parts of teeth being separated from each other and the gingiva and wherein different groups of computation modules represent at least parts of different dentitions which are cataloged as belonging to a catalog of target dentitions different groups of computation modules represent at least parts of different dentitions which are cataloged as belonging to a catalog of starting dentitions different groups of computation modules represent at least parts of different dentitions which are cataloged as belonging to a catalog of intermediary dentitions for each starting dentition and for each target dentition there are connections, preferably represented by different groups of computation modules, between a starting dentition, different intermediary dentitions and a target dentition, thereby establishing at least one sequence of intermediary dentitions leading from a starting dentition to a target dentition, wherein the plurality of parallelly executed processes further comprises at least one data hub process, the at least one data hub process being connected to the shared memory device or to the at least one first interface and being configured to segment the digital data record into data segments, if the digital data record is not already provided in form of data segments, and to provide each data segment with a key and wherein said computation modules are configured to:

check whether data segments provided with a specific key are present in the at least one shared memory device or are provided by at least one different group of computation modules;

run idly if no data segment with the specific key is detected or provided; and if a data segment with the specific key is detected in the at least one shared memory device or provided by at least one different group of computation modules, apply the machine learning technique on that data segment and output the result to at least one different group of computation modules or to the shared memory device or to the at least one output device.

8. The method of claim 7, wherein, based on an inputted digital data record representing a (part of a) dentition showing misalignment, the method comprises at least the following steps:

identify, in the catalog of starting dentitions, at least one dentition which is identical to or at least similar to the (part of a) dentition showing misalignment, and based on the identified at least one starting dentition, find at least one established sequence of intermediary dentitions in the catalog of intermediary dentitions, such that an endpoint of the sequence of intermediary dentitions is a target dentition in the catalog of target dentitions.

9. The method of claim 8, wherein a set of transformations necessary to transform the (part of a) dentition showing misalignment into the at least one target dentition via at least one of the sequences of intermediary dentitions is determined.

10. The method of claim 9, wherein:

a set of possible boundary conditions is provided based on the virtual model, in particular in case supplemental information is present in the virtual model, the system checks whether at least one of the boundary conditions is applicable if at least one of the boundary conditions is applicable, the method takes account of said at least one boundary condition when determining the sequence of intermediary dentitions.

11. The method of claim 9, wherein said sequence of intermediary dentitions is used to create at least one treatment plan and wherein the at least one treatment plan is provided in form of:

at least one CAD file, or at least one human-readable file.

12. A system for creating a virtual model representing at least part of a dentition of a patient, comprising:

at least one computing device which is configured to execute in parallel a plurality of processes at least one shared memory device which can be accessed by the at least one computing device at least one first interface for receiving a digital data record representing a 3d representation of at least part of a dentition of a patient and for storing the digital data record in the at least one shared memory device at least one second interface for outputting data wherein the plurality of parallelly executed processes comprises a plurality of groups of computation modules, each computation module being configured to run at least one neuronal network in order to apply a machine learning technique and each group of computation modules comprising one or more computation modules wherein different groups of computation modules represent different anatomical sub-structures that might be present in a dentition of a patient, each anatomical sub-structure being represented in different configurational states, shapes and sizes, the different anatomical sub-structures being at least: visible parts of teeth and gingiva each group of computation modules is configured to apply the machine learning technique on at least part of the digital data record and to output the result to at least one different group of computation modules and/or to the shared memory device and/or to the at least one second interface those anatomical sub-structures which are present in the at least part of a dentition represented by the digital data record are identified by those groups of computation modules which represent these anatomical sub-structures and the virtual model is created based on the identified anatomical sub-structures, said virtual model representing at least the visible parts of teeth, the visible parts of teeth being separated from each other and the gingiva and wherein the plurality of parallelly executed processes further comprises at least one data hub process, the at least one data hub process being connected to the shared memory device or to the at least one first interface and being configured to segment the digital data record into data segments, if the digital data record is not already provided in form of data segments, and to provide each data segment with a key and wherein said computation modules are configured to:

check whether data segments provided with a specific key are present in the at least one shared memory device or are provided by at least one different group of computation modules run idly if no data segment with the specific key is detected or provided if a data segment with the specific key is detected in the at least one shared memory device or provided by at least one different group of computation modules, apply the machine learning technique on that data segment and output the result to at least one different group of computation modules or to the shared memory device or to the at least one output device.

* * * * *